(12) United States Patent
Hasegawa et al.

(10) Patent No.: US 7,678,530 B2
(45) Date of Patent: Mar. 16, 2010

(54) LACTONE-CONTAINING COMPOUND, POLYMER, RESIST COMPOSITION, AND PATTERNING PROCESS

(75) Inventors: Koji Hasegawa, Joetsu (JP); Satoshi Watanabe, Joetsu (JP); Jun Hatakeyama, Joetsu (JP); Takeshi Kinsho, Joetsu (JP); Seiichiro Tachibana, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 146 days.

(21) Appl. No.: 11/649,251

(22) Filed: Jan. 4, 2007

(65) Prior Publication Data
US 2007/0160929 A1   Jul. 12, 2007

(30) Foreign Application Priority Data
Jan. 6, 2006   (JP) ............................. 2006-001102

(51) Int. Cl.
G03F 7/038   (2006.01)
G03F 7/039   (2006.01)
G03F 7/20    (2006.01)
G03F 7/30    (2006.01)

(52) U.S. Cl. ................. 430/270.1; 430/325; 430/326; 430/330; 430/907; 430/910; 526/270; 526/266; 526/268; 526/242; 549/300

(58) Field of Classification Search ............ None
See application file for complete search history.

(56) References Cited

U.S. PATENT DOCUMENTS

| | | | |
|---|---|---|---|
| 6,004,724 A | 12/1999 | Yamato et al. | |
| 6,261,738 B1 | 7/2001 | Asakura et al. | |
| 6,312,867 B1 | 11/2001 | Kinsho et al. | |
| 6,830,866 B2 | 12/2004 | Kobayashi et al. | |
| 6,916,591 B2 | 7/2005 | Ohsawa et al. | |
| 2005/0095532 A1* | 5/2005 | Kodama et al. ......... | 430/270.1 |
| 2006/0210922 A1* | 9/2006 | Nishiyama ............... | 430/270.1 |
| 2006/0246377 A1 | 11/2006 | Yamato et al. | |

FOREIGN PATENT DOCUMENTS

| | | |
|---|---|---|
| JP | 9-95479 A | 4/1997 |
| JP | 9-208554 A | 8/1997 |
| JP | 9-230588 A | 9/1997 |
| JP | 9-301948 A | 11/1997 |
| JP | 2906999 B2 | 4/1999 |
| JP | 2000-314956 A | 11/2000 |
| JP | 2000-336121 A | 12/2000 |
| JP | 2003-66612 A | 3/2003 |
| WO | WO-2004/074242 | 9/2004 |

OTHER PUBLICATIONS

Proc. SPIE vol. 4690 xxix.
Proc. SPIE vol. 5040, p. 724. (2003).
The 2nd Immersion Workshop, Jul. 11, 2003, Resist and Cover Material Investigation for Immersion Lithography.
J. Photopolymer Sci. and Technol., vol. 18, No. 5, p. 603, (2005).
J. Photopolym. Sci. and Tech., 8, p. 43-44, p. 45-46, (1995).
J. Photopolym. Sci. and Tech., 9, p. 29-30, (1996).

* cited by examiner

*Primary Examiner*—Sin J. Lee
(74) *Attorney, Agent, or Firm*—Birch, Stewart, Kolasch & Birch LLP

(57) ABSTRACT

Lactone-containing compounds having formula (1) are novel wherein $A^1$ is a polymerizable functional group having a double bond, $R^1$ is a monovalent $C_1$-$C_{10}$ hydrocarbon group in which some or all hydrogen atoms are substituted by fluorine atoms, and W is $CH_2$, O or S. They are useful as monomers to produce polymers for the formulation of radiation-sensitive resist compositions which have high transparency to radiation of up to 500 nm and exhibit good development properties. Radiation-sensitive resist compositions comprising the polymers as base resin exhibit high resolution and prevent dissolution in water and penetration of water when processed by immersion lithography.

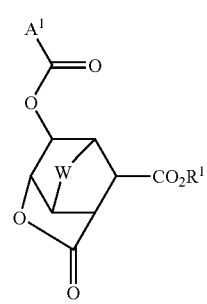

(1)

20 Claims, No Drawings

LACTONE-CONTAINING COMPOUND, POLYMER, RESIST COMPOSITION, AND PATTERNING PROCESS

CROSS-REFERENCE TO RELATED APPLICATION

This non-provisional application claims priority under 35 U.S.C. §119(a) on Patent Application No. 2006-001102 filed in Japan on Jan. 6, 2006, the entire contents of which are hereby incorporated by reference.

TECHNICAL FIELD

This invention relates to (1) novel lactone-containing compounds useful as monomers for the synthesis of polymers to be formulated as base resin in lithographic micropatterning resist materials, (2) polymers comprising recurring units derived from the lactone-containing compounds, (3) resist compositions comprising the polymers, and (4) a patterning process using the resist compositions.

BACKGROUND ART

In the recent drive for higher integration and operating speeds in LSI devices, the pattern rule is made drastically finer. The photolithography which is currently on widespread use in the art is approaching the essential limit of resolution determined by the wavelength of a light source. As the light source used in the lithography for resist pattern formation, g-line (436 nm) or i-line (365 nm) from a mercury lamp was widely used. One means believed effective for further reducing the feature size is to reduce the wavelength of exposure light. For the mass production process of 64 M-bit dynamic random access memory (DRAM, processing feature size 0.25 µm or less), the exposure light source of i-line (365 nm) was replaced by a KrF excimer laser having a shorter wavelength of 248 nm. However, for the fabrication of DRAM with a degree of integration of 256 M and 1 G or more requiring a finer patterning technology (processing feature size 0.2 µm or less), a shorter wavelength light source is required. Over a decade, photolithography using ArF excimer laser light (193 nm) has been under active investigation. It was expected at the initial that the ArF lithography would be applied to the fabrication of 180-nm node devices. However, the KrF excimer lithography survived to the mass-scale fabrication of 130-nm node devices. So, the full application of ArF lithography started from the 90-nm node. The ArF lithography combined with a lens having an increased numerical aperture (NA) of 0.9 is considered to comply with 65-nm node devices. For the next 45-nm node devices which required an advancement to reduce the wavelength of exposure light, the $F_2$ lithography of 157 nm wavelength became a candidate. However, for the reasons that the projection lens uses a large amount of expensive $CaF_2$ single crystal, the scanner thus becomes expensive, hard pellicles are introduced due to the extremely low durability of soft pellicles, the optical system must be accordingly altered, and the etch resistance of resist is low; the postponement of $F_2$ lithography and the early introduction of ArF immersion lithography were advocated (see Proc. SPIE Vol. 4690 xxix).

In the ArF immersion lithography, the space between the projection lens and the wafer is filled with water. Since water has a refractive index of 1.44 at 193 nm, pattern formation is possible even using a lens with NA of 1.0 or greater. Theoretically, it is possible to increase the NA to 1.44. The resolution is improved by an increment of NA. A combination of a lens having NA of at least 1.2 with ultra-high resolution technology suggests a way to the 45-nm node (see Proc. SPIE Vol. 5040, p 724).

Several problems associated with the presence of water on resist were pointed out. For example, projection lens contamination and pattern profile changes occur because the acid once generated from a photoacid generator and the amine compound added to the resist as a quencher can be dissolved in water. Inversely, swelling and circular defects known as water marks occur because water can penetrate into the resist film. For overcoming these problems, it was proposed to provide a protective coating between the resist and water (see the 2nd Immersion Workshop, Jul. 11, 2003, Resist and Cover Material Investigation for Immersion Lithography); and to prevent resist materials from dissolution in water or water penetration by controlling the water repellency of resist materials, typically photoacid generators (PAG) or base resins (see J. Photopolymer Sci. and Technol., Vol. 18, No. 5, p 603 (2005)).

SUMMARY OF THE INVENTION

An object of the present invention is to provide lactone-containing compounds useful as monomers for the synthesis of polymers, polymers comprising recurring units derived from the lactone-containing compounds, and resist compositions comprising the polymers, the resist compositions exhibiting a high resolution and preventing dissolution in immersion media and penetration of immersion media when processed by photolithography using high-energy radiation such as ArF excimer laser radiation as a light source, especially immersion lithography. Another object is to provide a patterning process using the resist compositions.

The inventor has found that a lactone-containing compound of the general formula (1) shown below can be readily prepared in high yields, and that a resist composition comprising a polymer derived from the lactone-containing compound as a base resin exhibits a high resolution and prevents dissolution in water as an immersion medium and penetration of water when processed by photolithography, especially immersion lithography so that the polymer is advantageously used in resist form for precise micropatterning.

Accordingly, the present invention provides a lactone-containing compound, polymer, resist composition, and patterning process, as defined below.

[1] A lactone-containing compound having the general formula (1):

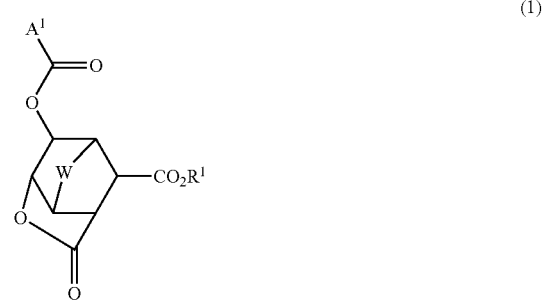

wherein $A^1$ is a polymerizable functional group having a carbon-to-carbon double bond, $R^1$ is a straight, branched or cyclic monovalent hydrocarbon group of 1 to 10 carbon atoms in which some or all hydrogen atoms on constituent carbons are substituted by fluorine atoms, and W is $CH_2$, an oxygen atom or sulfur atom.

[2] The lactone-containing compound of [1], having the general formula (2):

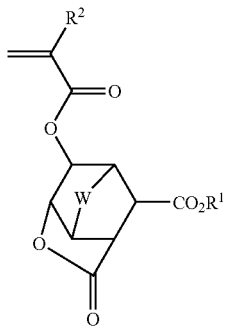
(2)

wherein $R^1$ and W are as defined above, and $R^2$ is hydrogen, fluorine, methyl or trifluoromethyl.

[3] The lactone-containing compound of [1], having the general formula (3):

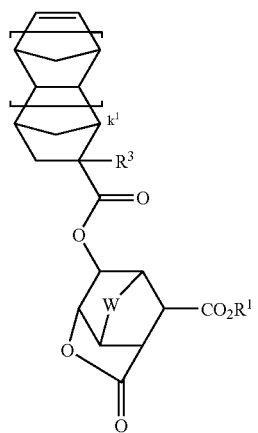
(3)

wherein $R^1$ and W are as defined above, $R^3$ is hydrogen, fluorine, methyl or trifluoromethyl, and $k^1$ is 0 or 1.

[4] A polymer comprising recurring units derived from the lactone-containing compound of [1].

[5] A polymer comprising recurring units having either one of the general formulas (1a) to (1c):

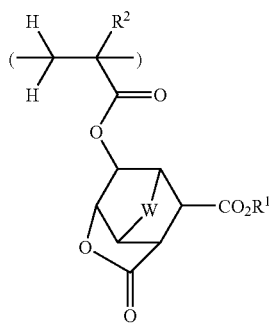
(1a)

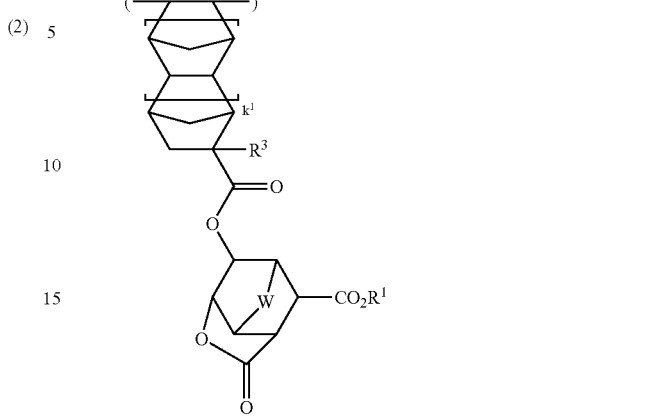
(1b)

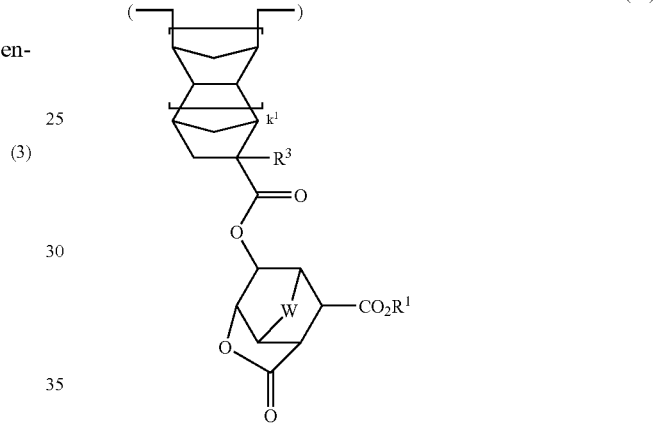
(1c)

wherein $R^1$ is a straight, branched or cyclic monovalent hydrocarbon group of 1 to 10 carbon atoms in which some or all hydrogen atoms on constituent carbons are substituted by fluorine atoms, $R^2$ is hydrogen, fluorine, methyl or trifluoromethyl, $R^3$ is hydrogen, fluorine, methyl or trifluoromethyl, W is $CH_2$, an oxygen atom or sulfur atom, and $k^1$ is 0 or 1.

[6] The polymer of [4] or [5], further comprising recurring units having at least one of the general formulas (4) to (7):

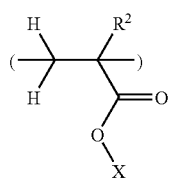
(4)

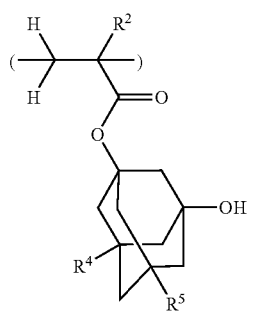
(5)

-continued

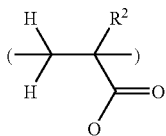
(6)

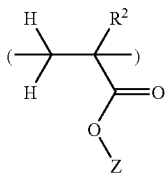
(7)

wherein $R^2$ is as defined above, $R^4$ and $R^5$ are each independently hydrogen or hydroxyl, X is an acid labile group, Y is a substituent group having a lactone structure different from formula (1), and Z is hydrogen, a fluoroalkyl group of 1 to 15 carbon atoms or a fluoroalcohol-containing substituent group of 1 to 15 carbon atoms.

[7] A resist composition comprising the polymer of any one of [4] to [6] as a base resin.

[8] A process for forming a pattern comprising the steps of applying the resist composition of [7] onto a substrate to form a coating, heat treating the coating, exposing the coating to high-energy radiation or electron beam through a photomask, optionally heat treating the exposed coating, and developing it with a developer.

BENEFITS OF THE INVENTION

The lactone-containing compounds of the invention are novel. They are useful as raw materials for the synthesis of polymers, functional materials, pharmaceutical and agricultural chemicals. They are most useful as monomers to produce polymers for the manufacture of radiation-sensitive resist compositions which have high transparency to radiation having a wavelength of up to 500 nm, especially up to 300 nm, and exhibit good development properties. Radiation-sensitive resist compositions comprising the polymers as base resin exhibit high resolution and prevent dissolution in water as an immersion medium and penetration of water when processed by photolithography, especially immersion lithography. The polymers are advantageously used in resist form for precise micropatterning.

DESCRIPTION OF THE PREFERRED EMBODIMENTS

Lactone-Containing Compound

The lactone-containing compounds of the invention have the general formula (1).

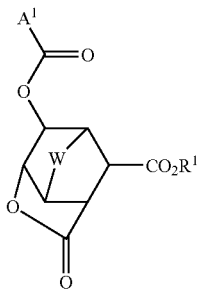
(1)

Herein $A^1$ is a polymerizable functional group having a carbon-to-carbon double bond, $R^1$ is a straight, branched or cyclic monovalent hydrocarbon group of 1 to 10 carbon atoms in which some or all hydrogen atoms on constituent carbons are substituted by fluorine atoms, and W is $CH_2$, an oxygen atom or sulfur atom.

Examples of $A^1$ include vinyl, 2-fluorovinyl, 2-trifluoromethylvinyl, allyl, 1-propenyl, isopropenyl, norbornenyl, 7-oxanorbornenyl, and tetracyclo[4.4.0.1$^{2,5}$.1$^{7,10}$]dodecenyl.

Examples of $R^1$ are given below.

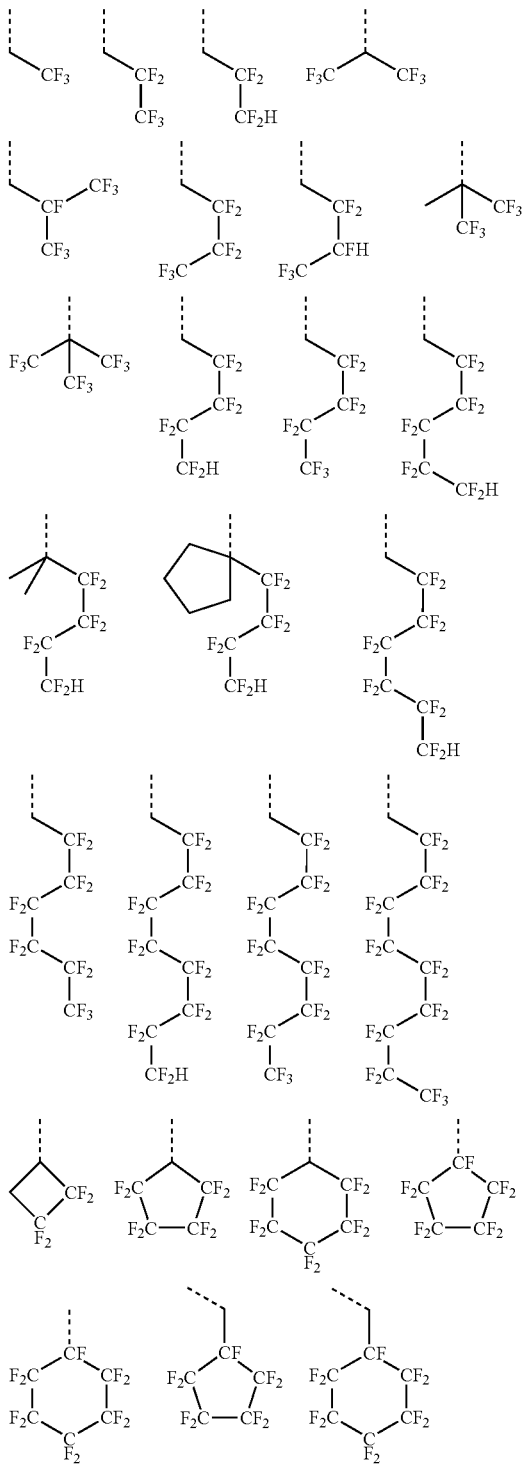

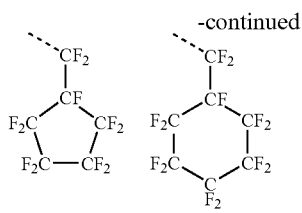

It is noted that the broken line as depicted herein and throughout the specification denotes a valence bond.

Of the compounds of formula (1), compounds having the general formula (2) are preferred.

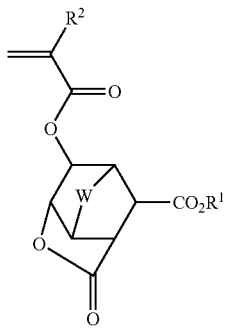
(2)

Herein $R^1$ and W are as defined above, and $R^2$ is a hydrogen atom, fluorine atom, methyl group or trifluoromethyl group.

Of the compounds of formula (1), compounds having the general formula (3) are more preferred.

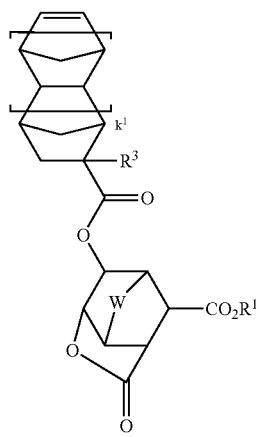
(3)

Herein $R^1$ and W are as defined above, $R^3$ is a hydrogen atom, fluorine atom, methyl group or trifluoromethyl group, and $k^1$ is 0 or 1.

Illustrative, non-limiting examples of the compounds having formulas (1) to (3) are given below.

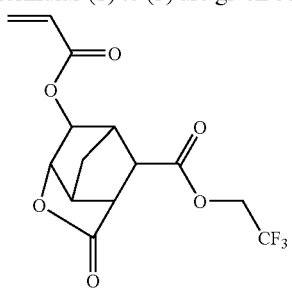

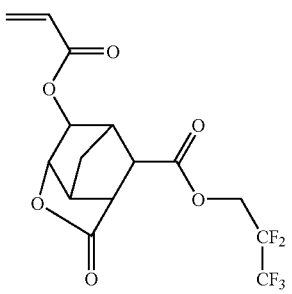

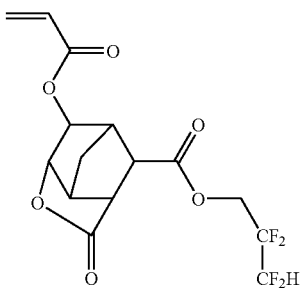

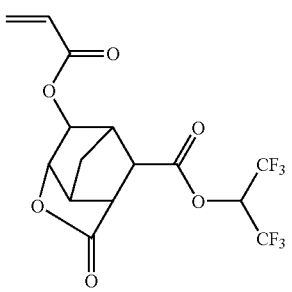

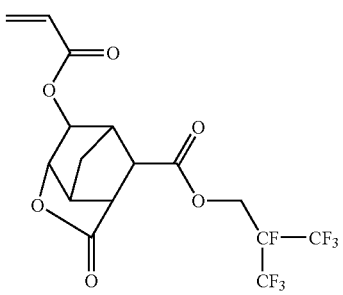

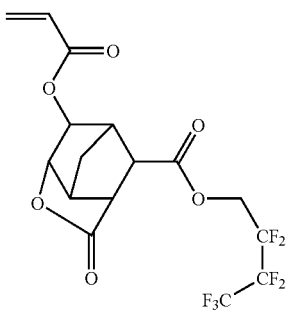

-continued
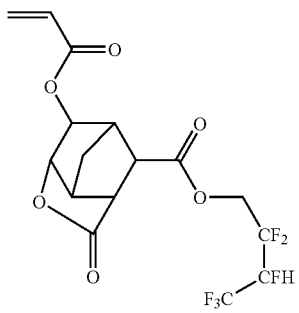
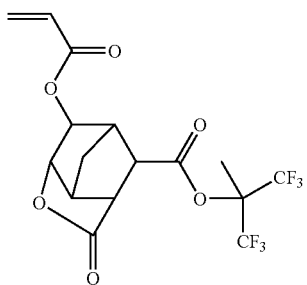
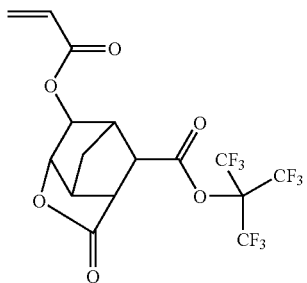
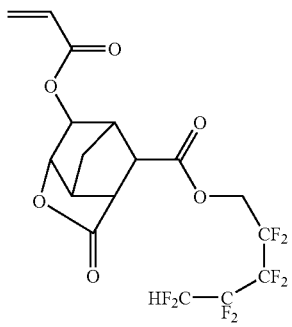
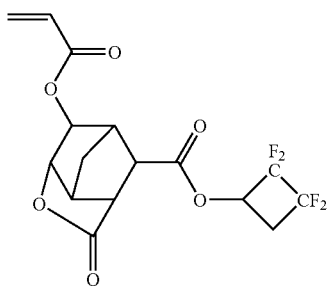
-continued
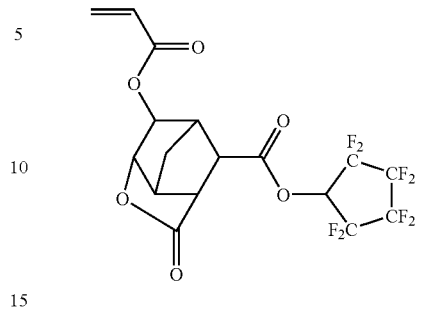
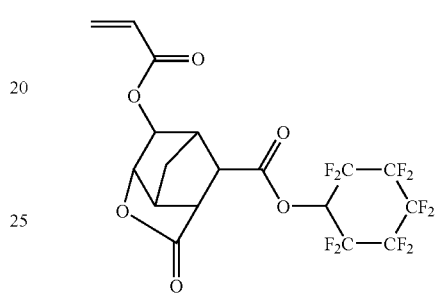
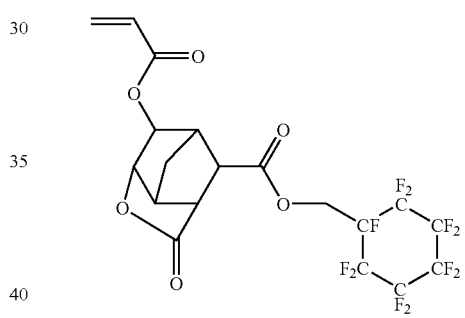
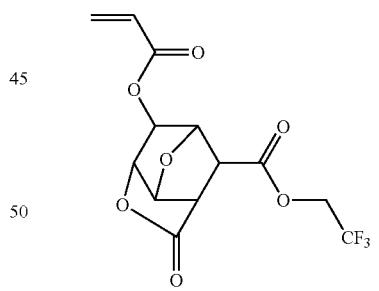
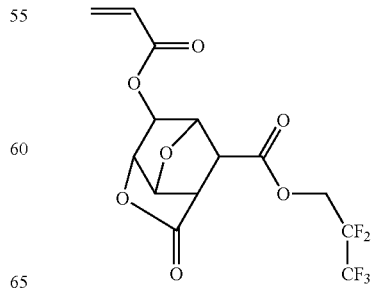

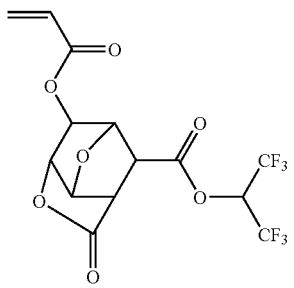
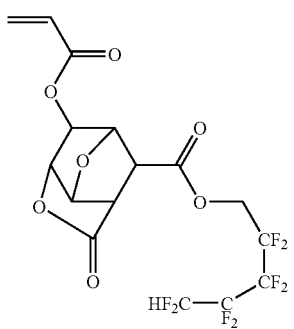
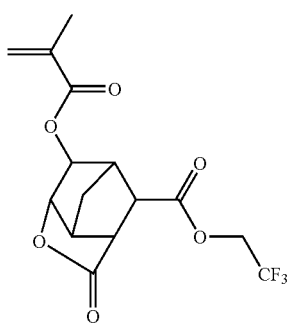
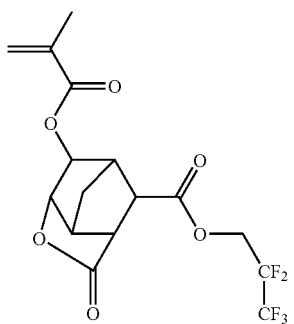
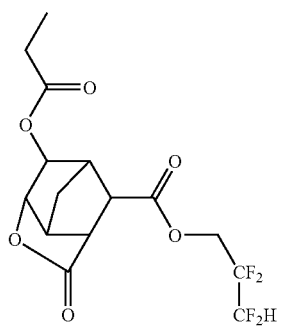
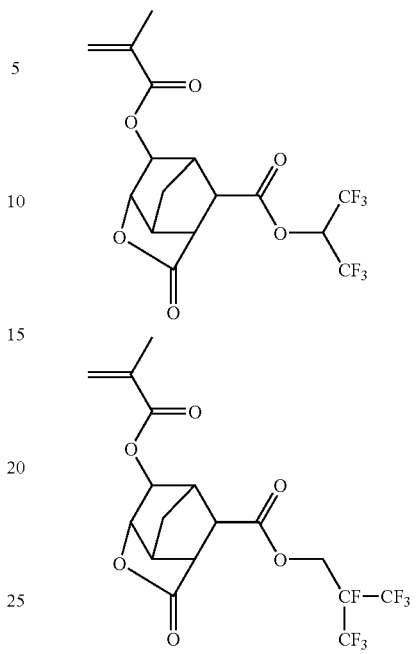
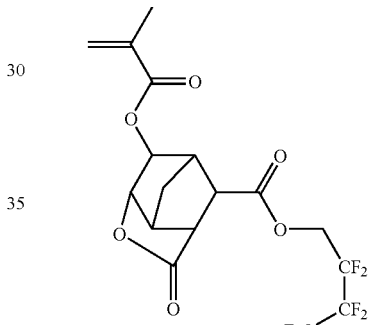
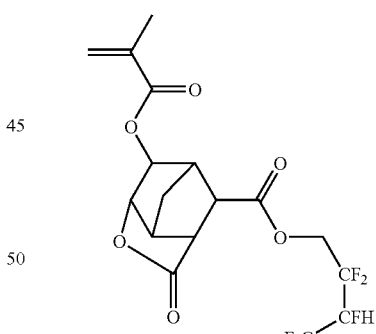
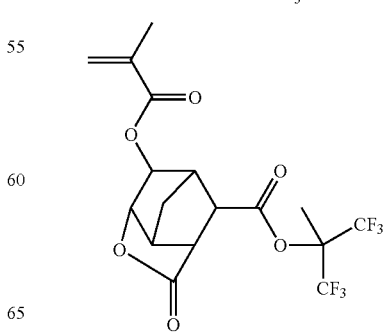

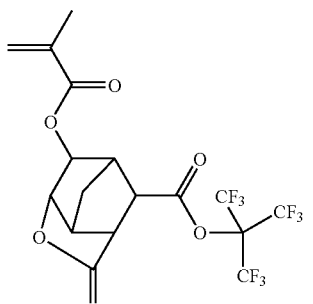
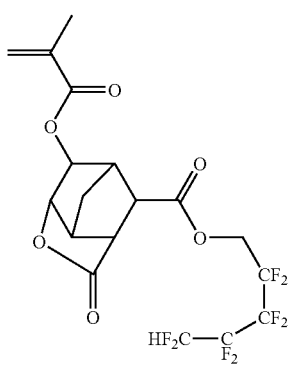
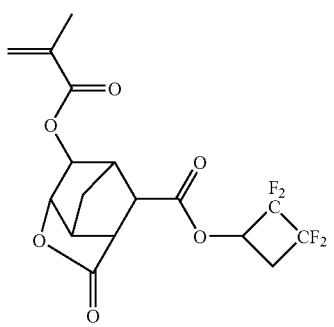
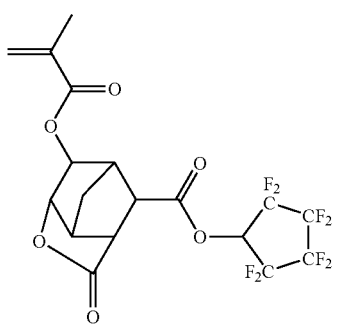
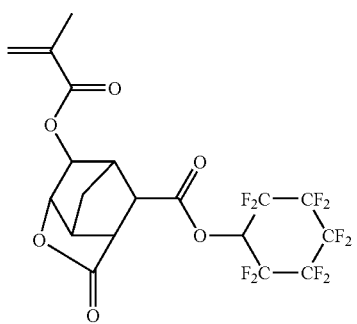
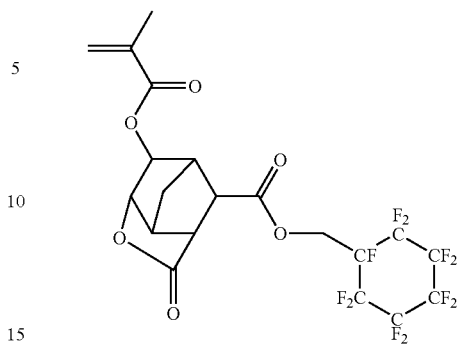
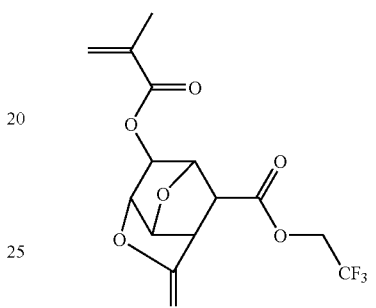
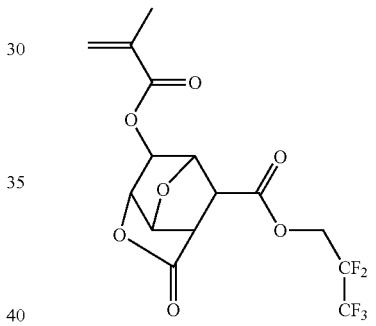
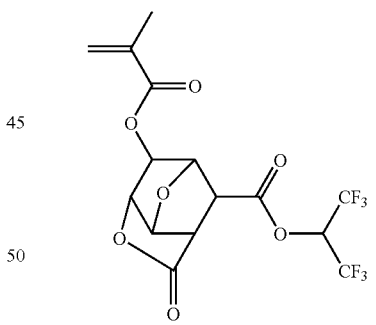
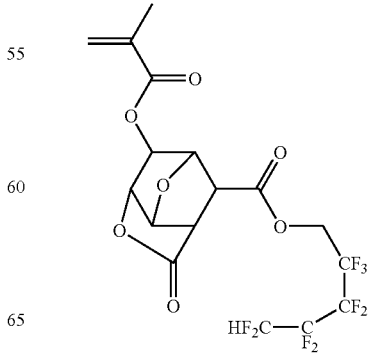

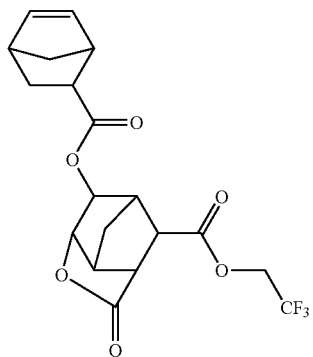
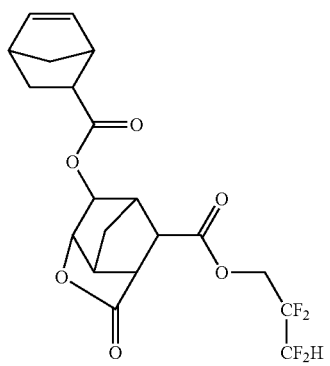
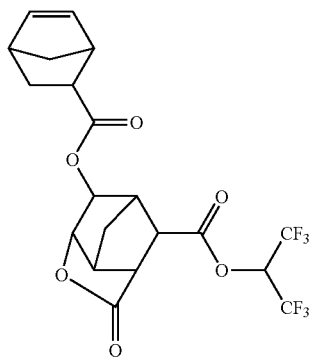
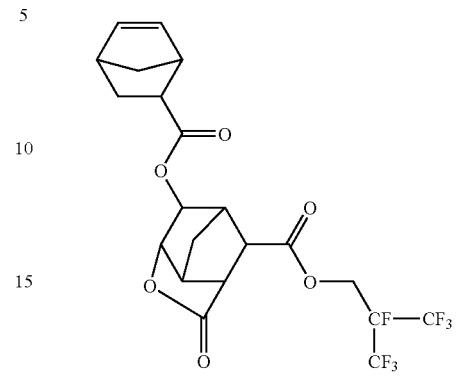
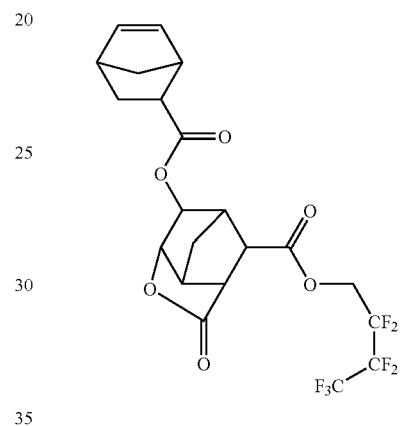
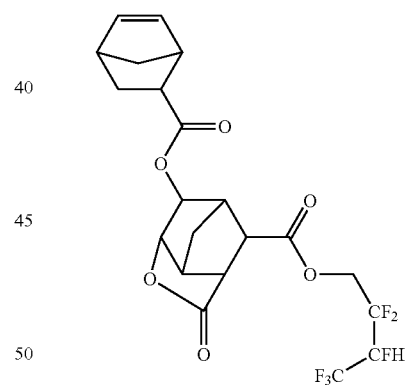
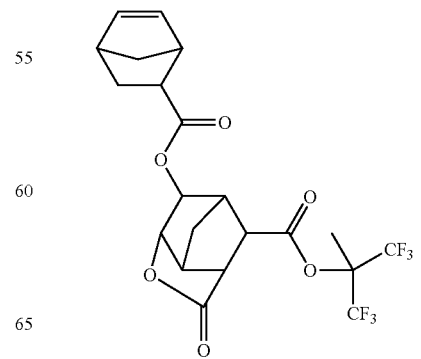

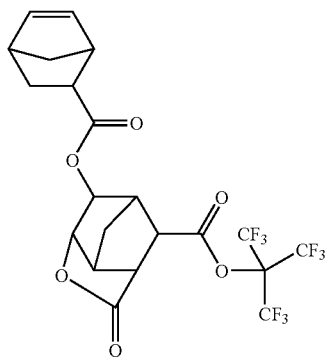
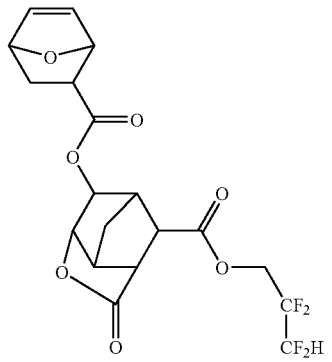
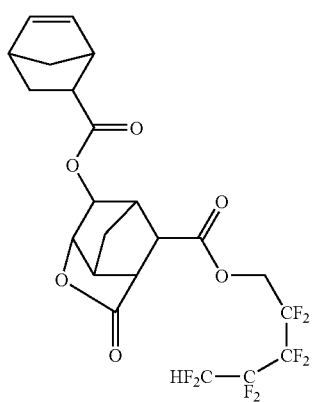
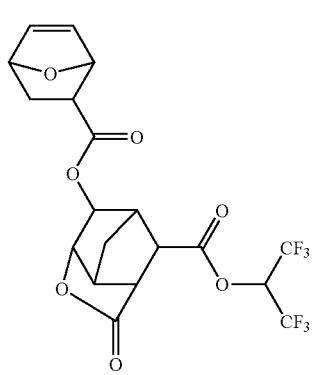
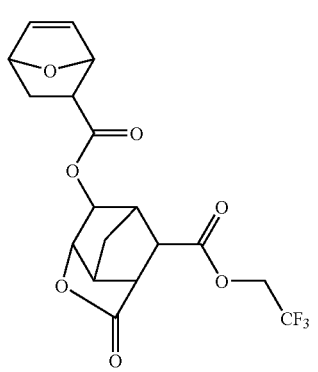
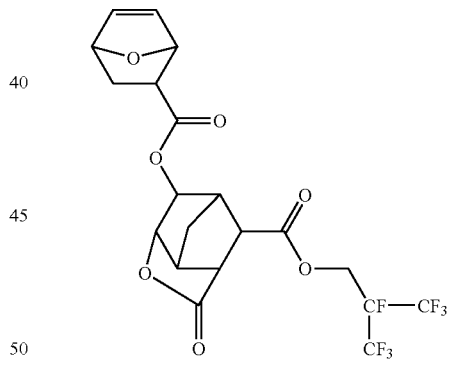
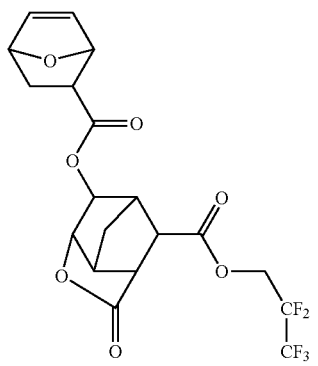
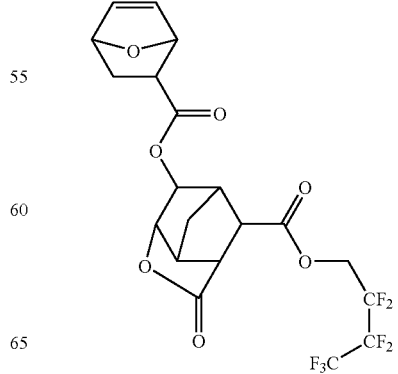

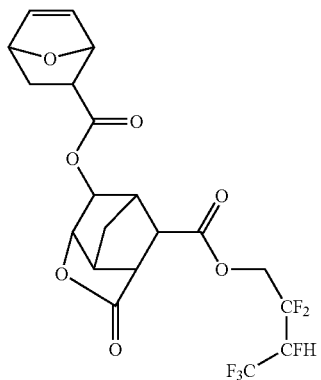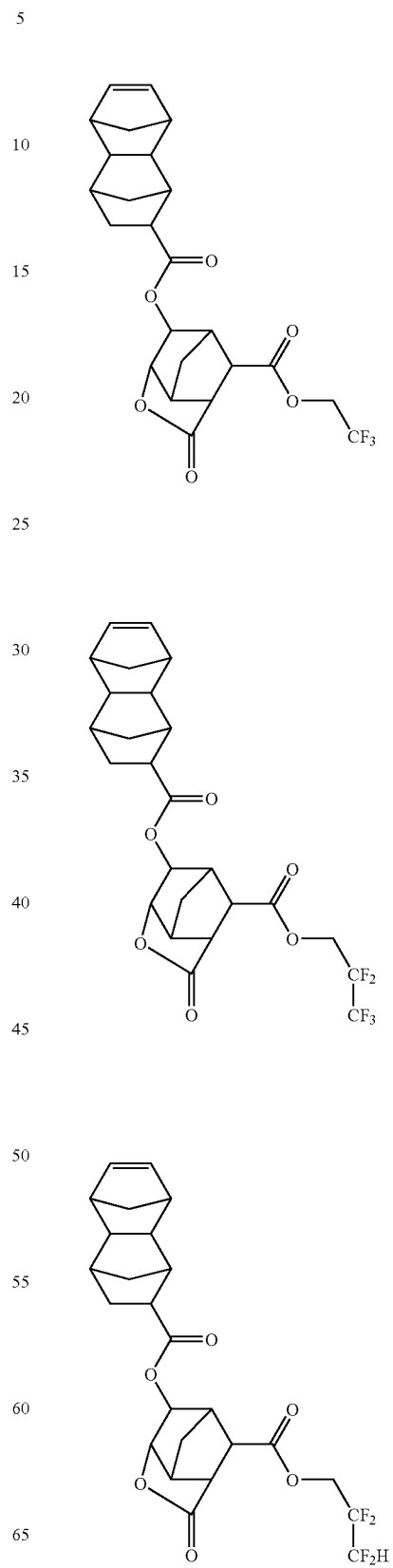

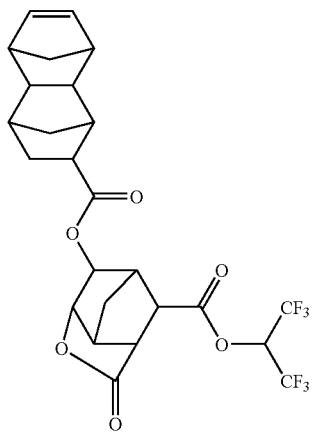
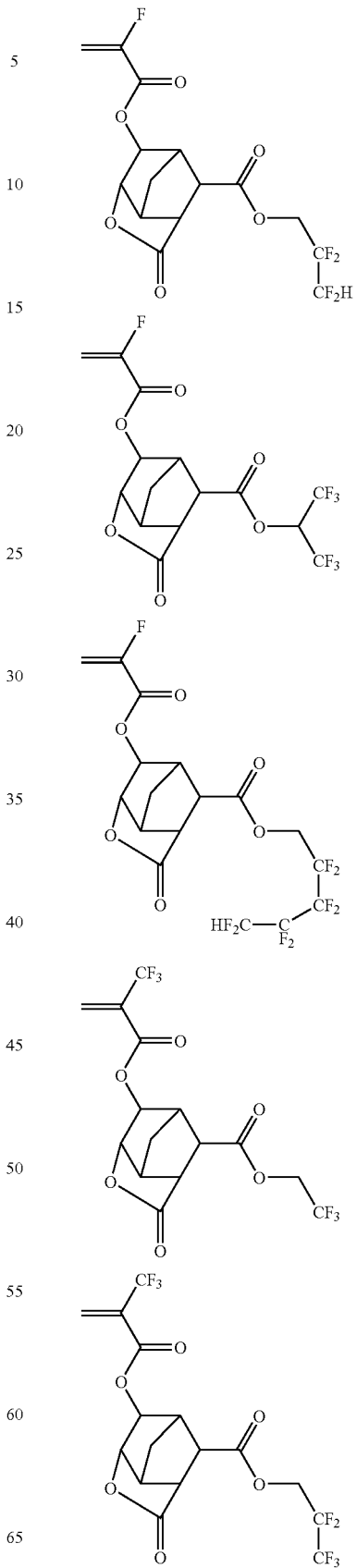

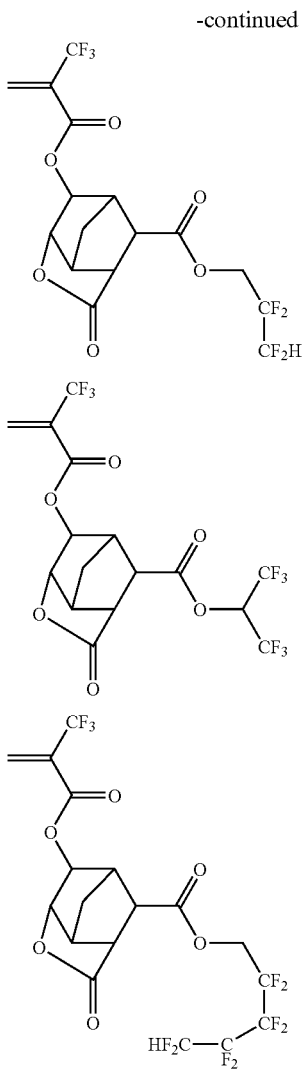

The lactone-containing compounds of formula (1) can be produced by the reaction scheme shown below, for example, but the invention is not limited thereto.

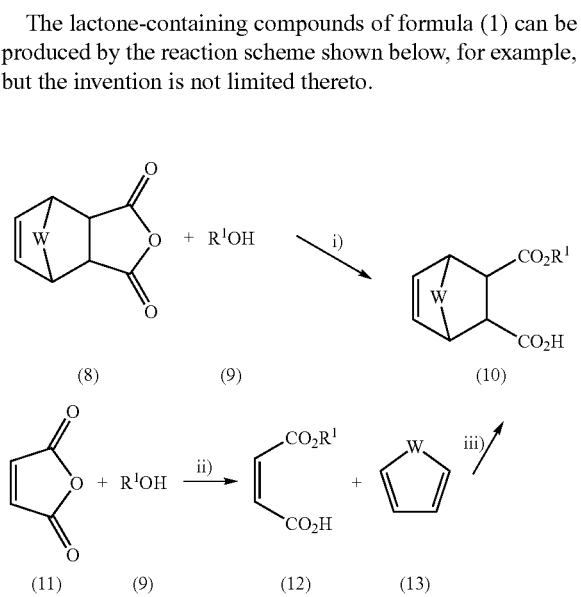

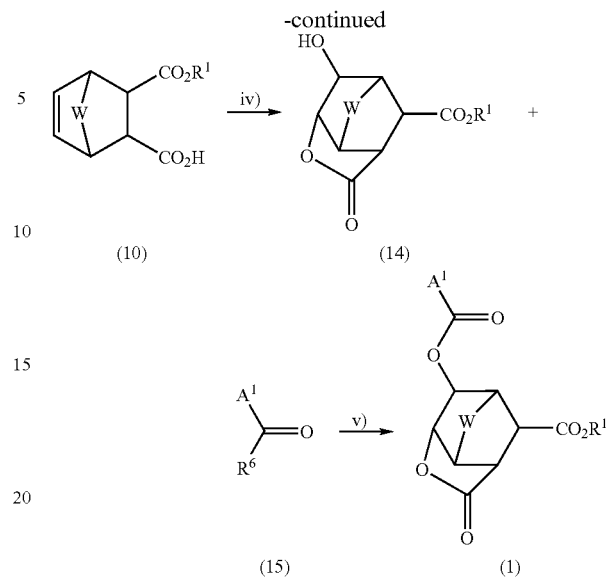

Herein, $A^1$, W, and $R^1$ are as defined above. $R^6$ is a halogen atom or $-OR^7$. $R^7$ is hydrogen, $-C(=O)A^1$, methyl or ethyl.

The first stage is to form an intermediate carboxylic acid (10) through step (i) or steps (ii) and (iii).

In step (i), carboxylic acid (10) can be synthesized through reaction of acid anhydride (8) with alcohol (9). The reaction takes place in a solventless system or in a hydrocarbon solvent such as toluene or xylene by heating at 40 to 150° C. and optionally adding an organic base such as triethylamine, pyridine or 4-dimethylaminopyridine. Carboxylic acid (10) can also be synthesized by reacting alcohol (9) with a metal hydride (e.g., borane, alkylborane, sodium hydride, lithium hydride, potassium hydride or calcium hydride), an alkyl metal compound (e.g., trityllithium, tritylsodium, tritylpotassium, methyllithium, phenyllithium, n-butyllithium, sec-butyllithium, tert-butyllithium or ethylmagnesium bromide), or an alkoxide (e.g., sodium methoxide, sodium ethoxide, lithium methoxide, lithium ethoxide, lithium tert-butoxide or potassium tert-butoxide) to form a corresponding alkoxide, and reacting it with acid anhydride (8).

In steps (ii) and (iii), carboxylic acid (10) can be synthesized by reacting acid anhydride (11) with alcohol (9) to form carboxylic acid (12), followed by Diels-Alder reaction of carboxylic acid (12) with diene (13). Specifically, the synthesis of carboxylic acid (12) is possible by the same method as described for step (i). The Diels-Alder reaction of carboxylic acid (12) with diene (13) takes place under well-known conditions. For example, where diene (13) is cyclopentadiene (corresponding to formula (13) wherein W is $-CH_2-$), the reaction preferably takes place in a solventless system or in a hydrocarbon solvent such as n-hexane, n-heptane, benzene, toluene or xylene while optionally heating at 30 to 100° C.

Where diene (13) is furan (corresponding to formula (13) wherein W is $-O-$), the reaction takes place in a solventless system or in a hydrocarbon solvent such as n-hexane, n-heptane, benzene, toluene or xylene at a temperature of $-30°$ C. to 20° C. while a Lewis acid (e.g., lithium chloride, aluminum chloride, zinc chloride, zinc iodide, titanium tetrachloride, boron trifluoride or borane-tetrahydrofuran complex) is added as a catalyst. This mode of reaction is preferred for higher yields.

The second stage is to form intermediate alcohol (14) through step (iv). In step (iv), alcohol (14) can be synthesized through oxidizing reaction of the double bond on carboxylic acid (10) to induce lactone ring formation.

Examples of the oxidizing agent used herein include m-chloroperbenzoic acid, performic acid, peracetic acid, hydrogen peroxide, and oxygen. The oxidizing agent is desirably used in an amount of 0.5 to 4.0 moles, more desirably 1.0 to 2.5 moles per mole of carboxylic acid (10). A solvent or a mixture of solvents may be used. Preferred examples of the solvent include water, methylene chloride, tetrahydrofuran, ethers such as diethyl ether, di-n-butyl ether and 1,4-dioxane, and hydrocarbons such as n-hexane, n-heptane, benzene, toluene, xylene and cumene. The reaction temperature and time vary widely with other parameters. Where performic acid is used as the oxidizing agent, for example, the reaction temperature is generally 10 to 80° C., preferably 30 to 50° C. The reaction time is desirably determined by monitoring the reaction until the completion by gas chromatography (GC) or silica gel thin-layer chromatography (TLC) because higher yields are expectable. The reaction time is usually about 0.5 to about 15 hours. From the reaction mixture, alcohol (14) is obtained by a conventional aqueous work-up step. If necessary, alcohol (14) is purified by any conventional technique such as distillation, chromatography or recrystallization.

The third stage is to form lactone-containing compound (1) through step (v). In step (v), lactone-containing compound (1) can be synthesized through reaction of alcohol (14) with esterifying agent (15).

The reaction may be readily conducted by a well-known technique. The preferred esterifying agent (15) is an acid chloride (corresponding to formula (15) wherein $R^6$ is chlorine) or a carboxylic acid (corresponding to formula (15) wherein $R^6$ is hydroxyl). When an acid chloride is used as the esterifying agent, the reaction may be conducted in a solventless system or in a solvent such as methylene chloride, toluene or hexane, by sequentially or simultaneously adding the alcohol (14), the acid chloride such as methacrylic acid chloride or norbornenecarboxylic acid chloride, and a base such as triethylamine, pyridine or 4-dimethylaminopyridine, and optionally cooling or heating. When a carboxylic acid is used as the esterifying agent, the reaction may be conducted in a solvent such as toluene or hexane, by adding the alcohol (14), the carboxylic acid such as methacrylic acid or norbornenecarboxylic acid, and an inorganic acid such as hydrochloric acid, sulfuric acid, nitric acid or hydrogen perchloric acid, or an organic acid such as p-toluenesulfonic acid or benzenesulfonic acid, heating, and optionally removing the water of reaction from the system.

Polymer

In the second aspect, the invention provides a polymer comprising recurring units derived from the lactone-containing compound of formula (1).

Specifically, the recurring units derived from the lactone-containing compound of formula (1) include recurring units having the general formulas (1a) to (1c).

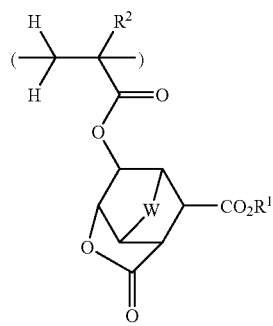
(1a)

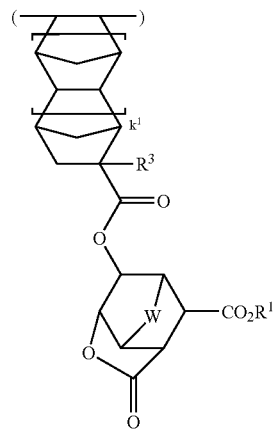
(1b)

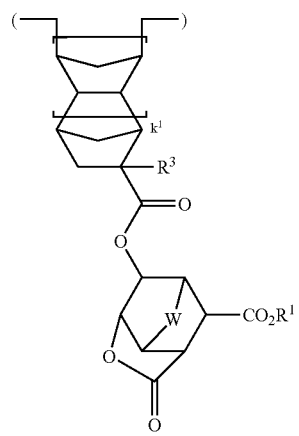
(1c)

Herein $R^1$ to $R^3$, W and $k^1$ are as defined above.

In addition to the recurring units derived from the compounds having formulas (1) to (3), specifically recurring units having formulas (1a) to (1c), the polymers of the invention may further comprise recurring units having at least one of the general formulas (4) to (7).

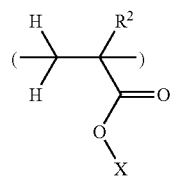
(4)

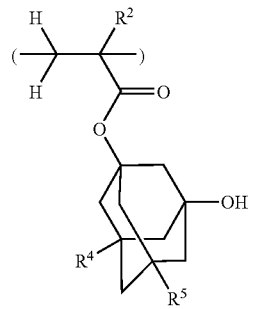
(5)

-continued

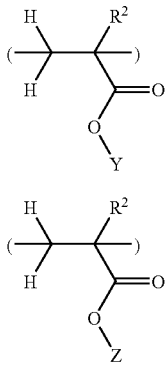

(6)

(7)

Herein $R^2$ is as defined above, $R^4$ and $R^5$ are each independently a hydrogen atom or hydroxyl group, X is an acid labile group, Y is a substituent group having a lactone structure different from formula (1), and Z is a hydrogen atom, a fluoroalkyl group of 1 to 15 carbon atoms or a fluoroalcohol-containing substituent group of 1 to 15 carbon atoms.

Under the action of acid, a polymer comprising recurring units of formula (4) is decomposed to generate carboxylic acid, turning to be an alkali soluble polymer. The acid labile group represented by X may be selected from a variety of such groups. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

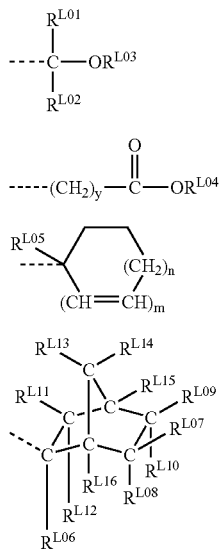

In these formulae, the broken line denotes a valence bond. $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, n-propyl, isopropyl, n-butyl, sec-butyl, tert-butyl, cyclopentyl, cyclohexyl, 2-ethylhexyl, and n-octyl. $R^{L03}$ is a monovalent hydrocarbon group of 1 to 18 carbon atoms, preferably 1 to 10 carbon atoms, which may contain a hetero atom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like. Illustrative examples are the substituted alkyl groups shown below.

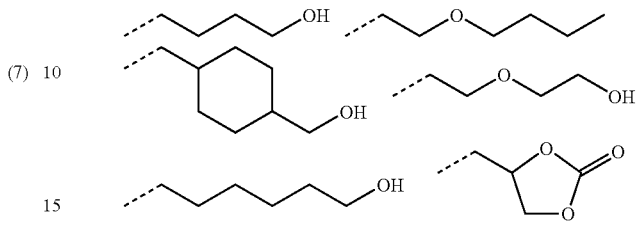

A pair of $R^{L01}$ and $R^{L02}$, $R^{L01}$ and $R^{L03}$, or $R^{L02}$ and $R^{L03}$ may form a ring with carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

$R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter y is an integer of 0 to 6.

In formula (L3), $R^{L05}$ is a substituted or unsubstituted, straight, branched or cyclic alkyl group of 1 to 8 carbon atoms or a substituted or unsubstituted aryl group of 6 to 20 carbon atoms. Examples of the optionally substituted alkyl group include straight, branched or cyclic alkyl groups such as methyl, ethyl, n-propyl, isopropyl, n-butyl, sec-butyl, tert-butyl, tert-amyl, n-pentyl, n-hexyl, cyclopentyl, and cyclohexyl, and substituted forms of such groups in which some hydrogen atoms are substituted with hydroxyl, alkoxy, carboxy, alkoxycarbonyl, oxo, amino, alkylamino, cyano, mercapto, alkylthio, sulfo or other groups. Exemplary aryl groups are phenyl, methylphenyl, naphthyl, anthryl, phenanthryl, and pyrenyl. Letter m is equal to 0 or 1, n is equal to 0, 1, 2 or 3, and 2m+n is equal to 2 or 3.

In formula (L4), $R^{L06}$ is a substituted or unsubstituted, straight, branched or cyclic alkyl group of 1 to 8 carbon atoms or a substituted or unsubstituted aryl group of 6 to 20 carbon atoms. Examples of these groups are the same as exemplified for $R^{L05}$. $R^{L07}$ to $R^{L16}$ independently represent hydrogen or monovalent hydrocarbon groups of 1 to 15 carbon atoms. Exemplary hydrocarbon groups are straight, branched or cyclic alkyl groups such as methyl, ethyl, n-propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxy, alkoxycarbonyl, oxo, amino, alkylamino, cyano, mercapto, alkylthio, sulfo or other groups. Alternatively, $R^{L07}$ to $R^{L16}$, taken together, form a ring (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to adjoining carbon atoms (for example, a pair of $R^{L07}$ and $R^{L09}$, $R^{L09}$ and $R^{L15}$, $R^{L13}$ and $R^{L15}$, or a similar pair) may bond together directly to form a double bond.

Of the acid labile groups of formula (L1), the straight and branched ones are exemplified by the following groups.

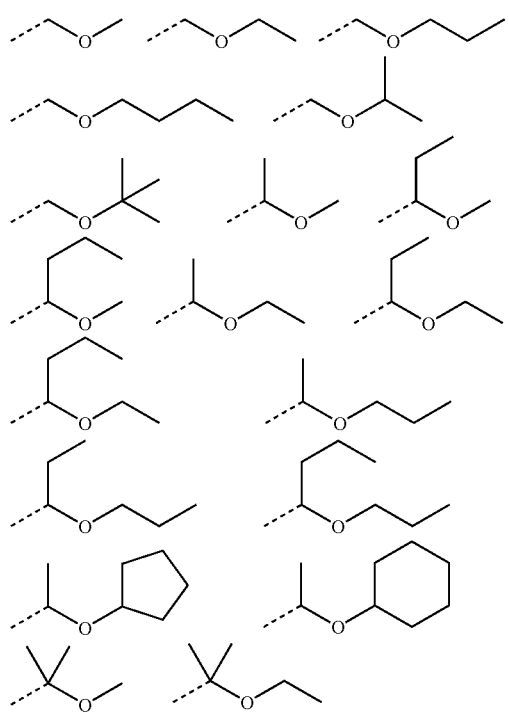

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Of the acid labile groups having formula (L4), groups having the following formulas (L4-1) to (L4-4) are preferred.

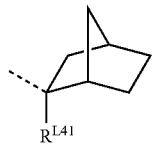
(L4-1)

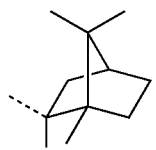
(L4-2)

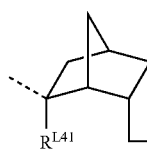
(L4-3)

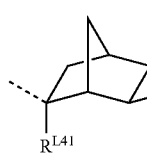
(L4-4)

In formulas (L4-1) to (L4-4), the broken line denotes a bonding site and direction. $R^{L41}$ is each independently a monovalent hydrocarbon group, typically a straight, branched or cyclic alkyl group of 1 to 10 carbon atoms, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two or more selected from groups having the following general formulas (L4-3-1) and (L4-3-2).

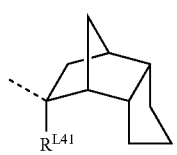
(L4-3-1)

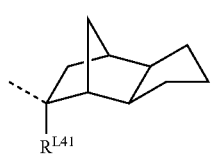
(L4-3-2)

Similarly, the general formula (L4-4) represents one or a mixture of two or more selected from groups having the following general formulas (L4-4-1) to (L4-4-4).

(L4-4-1)
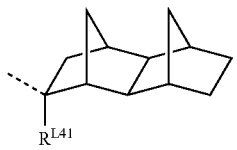

(L4-4-2)
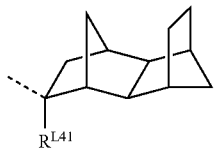

(L4-4-3)
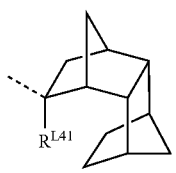

(L4-4-4)
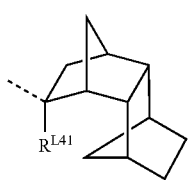

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyclo [2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

(L4-1-endo)
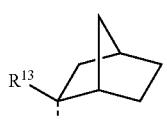

(L4-2-endo)
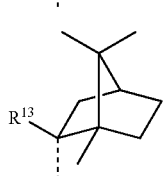

(L4-3-endo)
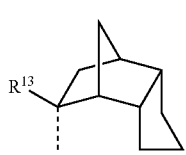

(L4-4-endo)
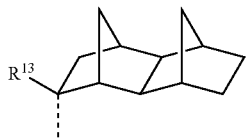

Illustrative examples of the acid labile group of formula (L4) are given below.

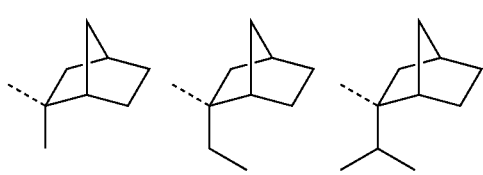

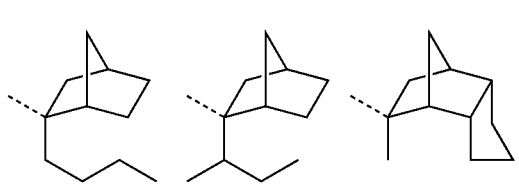

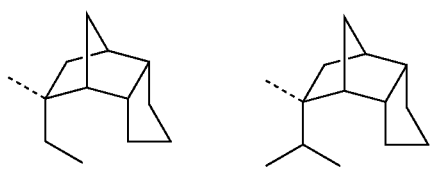

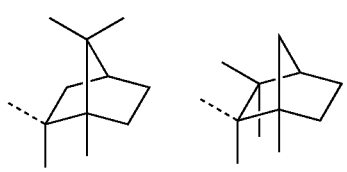

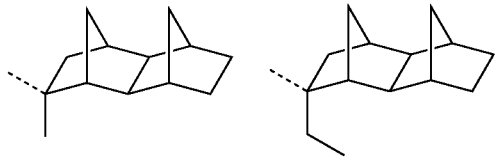

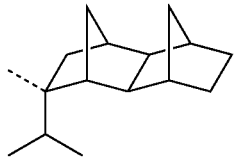

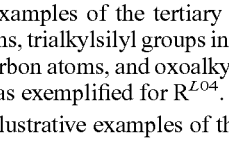

Examples of the tertiary alkyl groups of 4 to 20 carbon atoms, trialkylsilyl groups in which each alkyl moiety has 1 to 6 carbon atoms, and oxoalkyl groups of 4 to 20 carbon atoms are as exemplified for $R^{L04}$.

Illustrative examples of the recurring units of formula (4) are given below although the invention is not limited thereto.

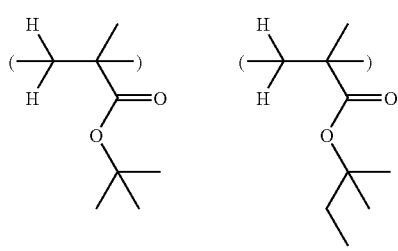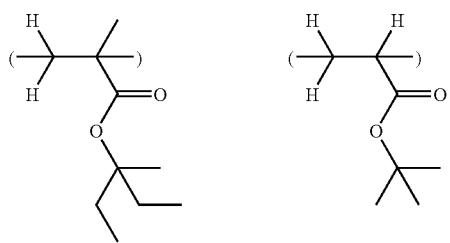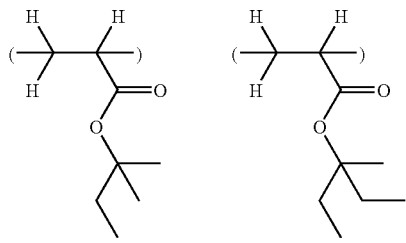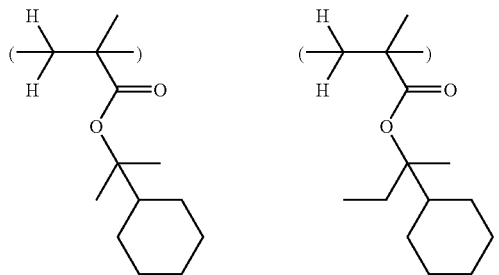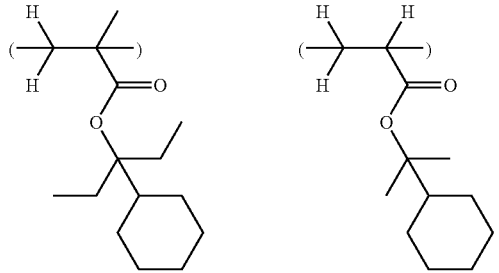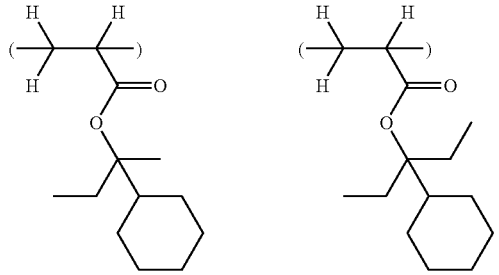
-continued
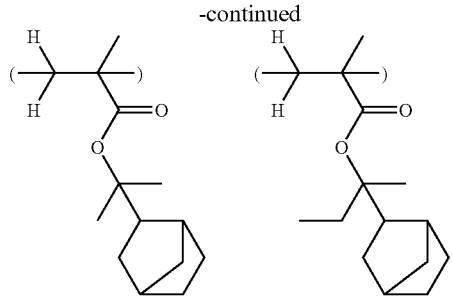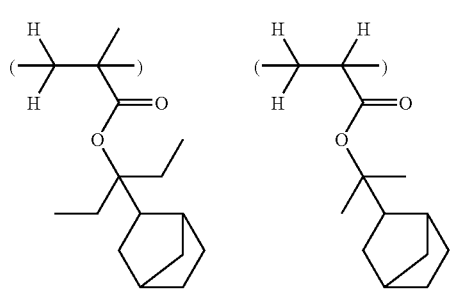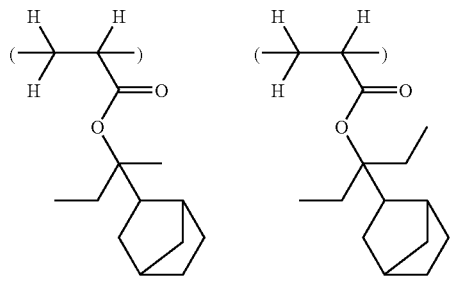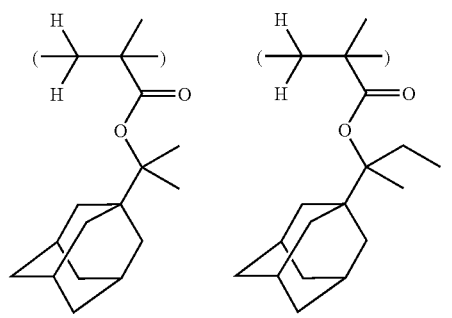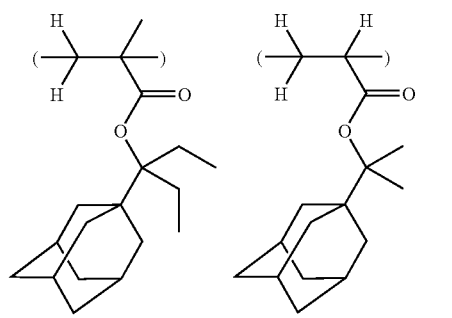

-continued
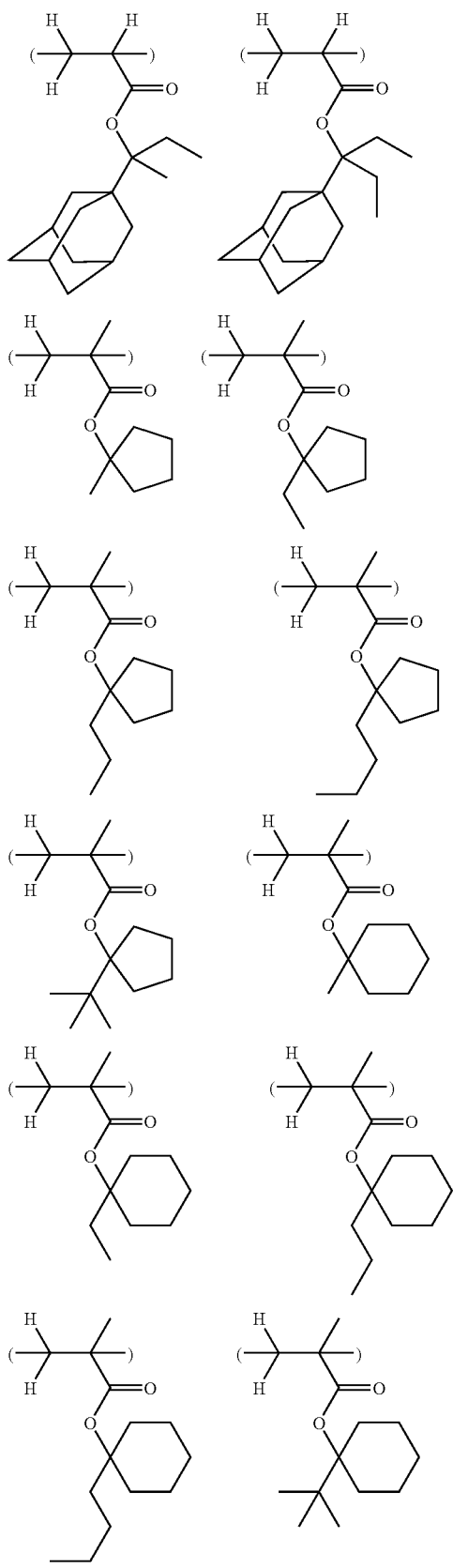
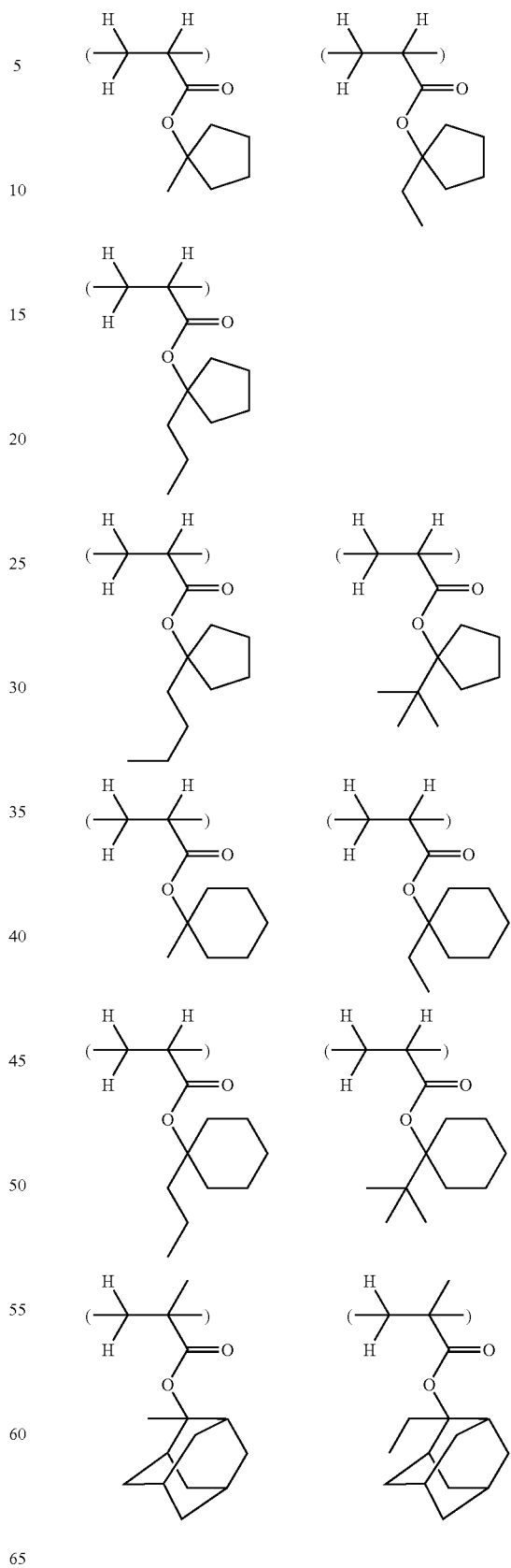

-continued
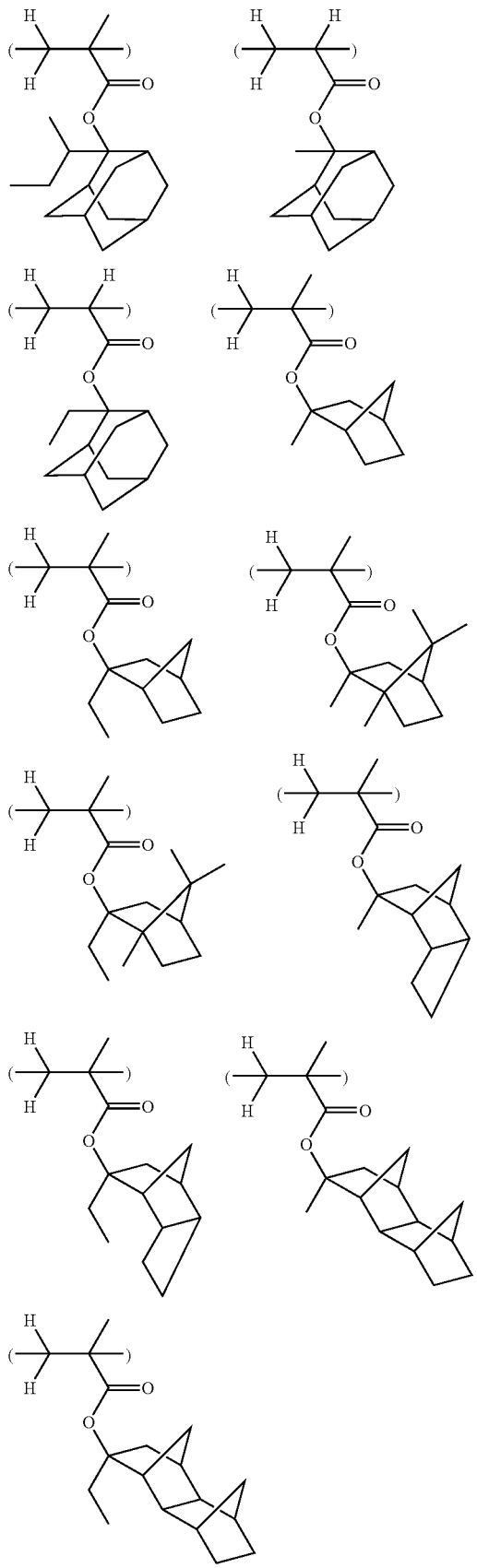
-continued
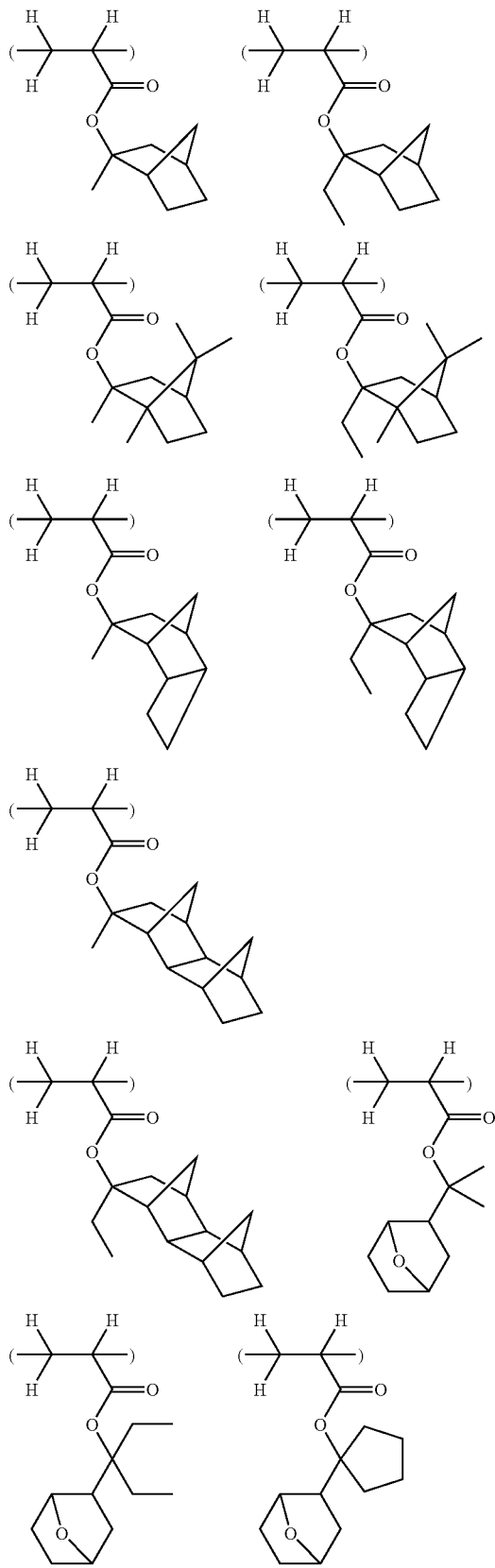

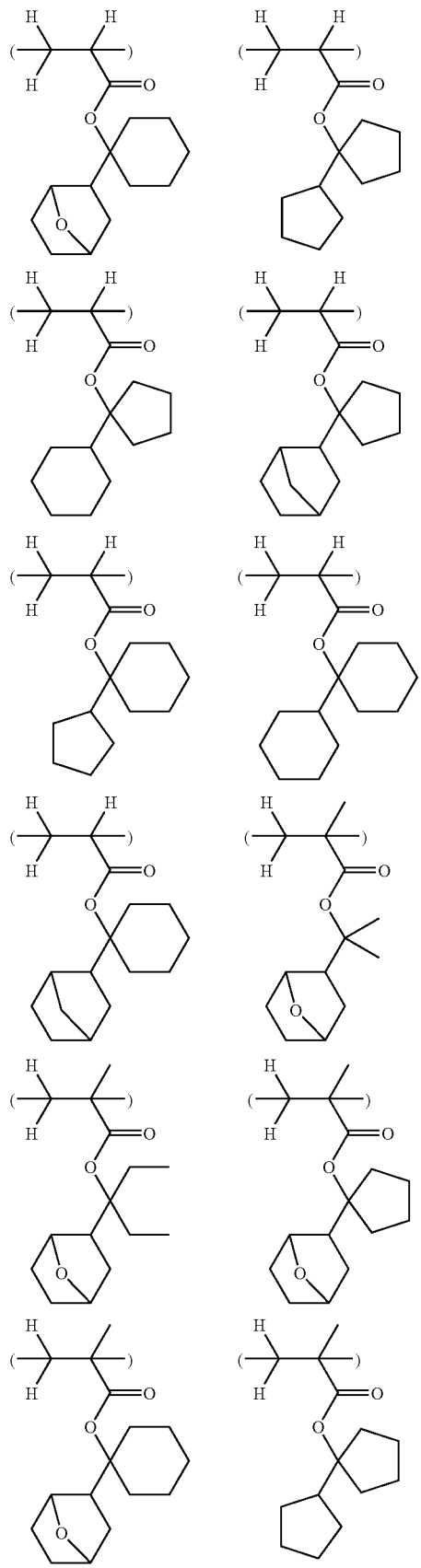
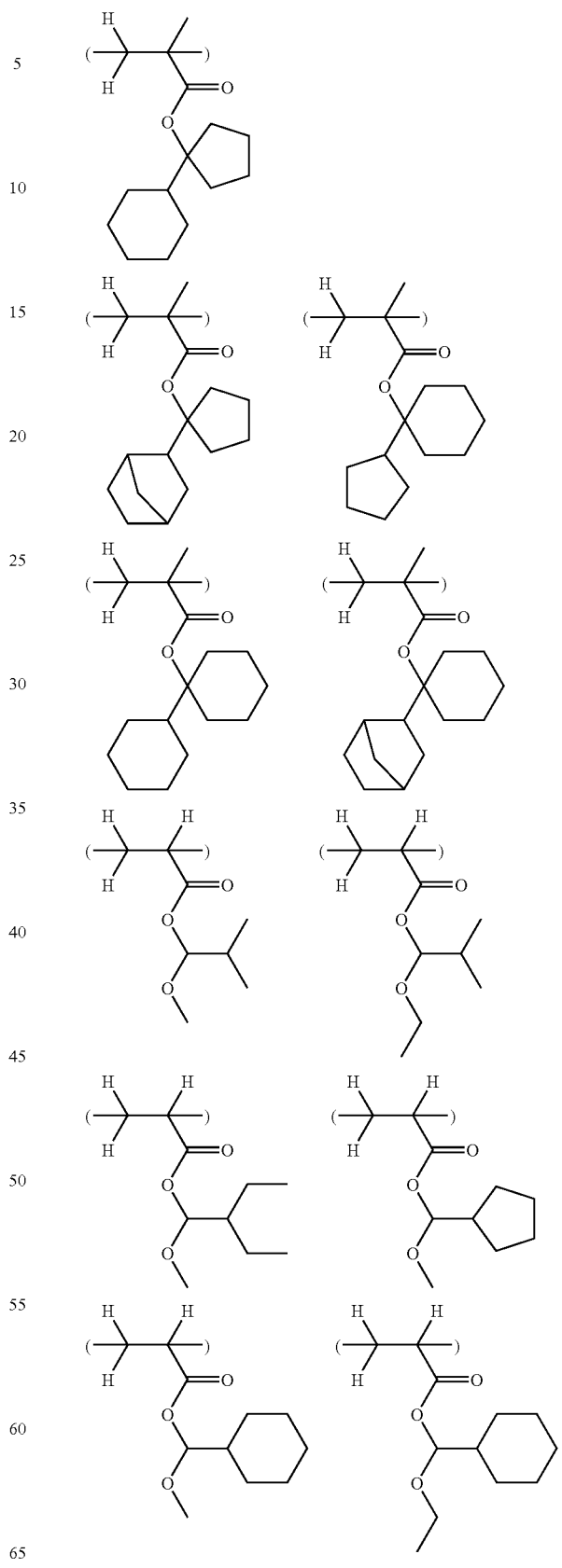

-continued
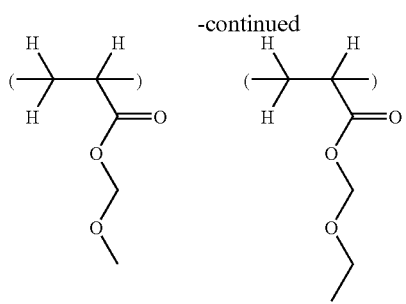
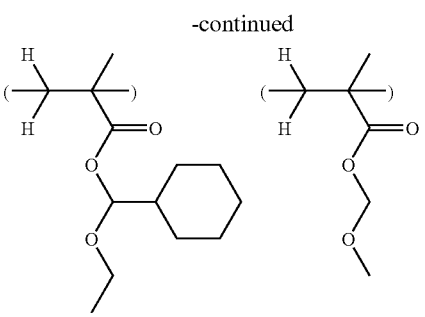
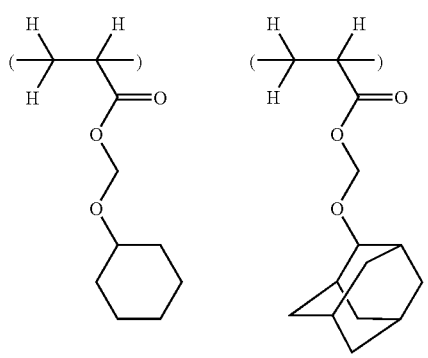
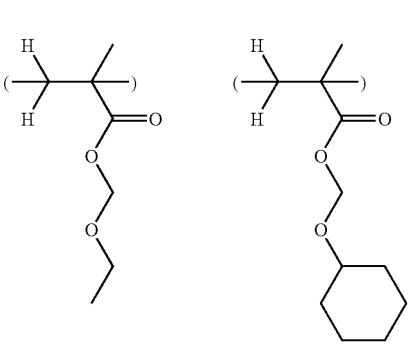
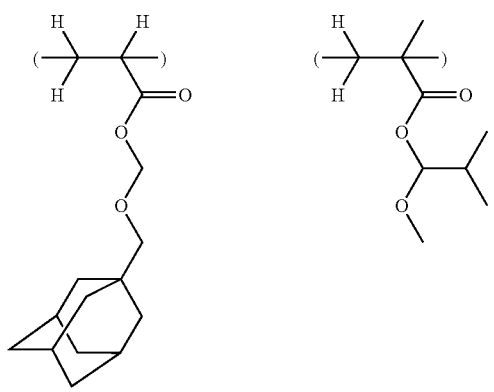
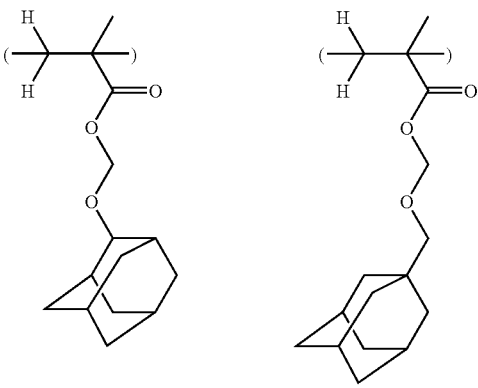
Illustrative examples of the recurring units of formula (5) are given below although the invention is not limited thereto.
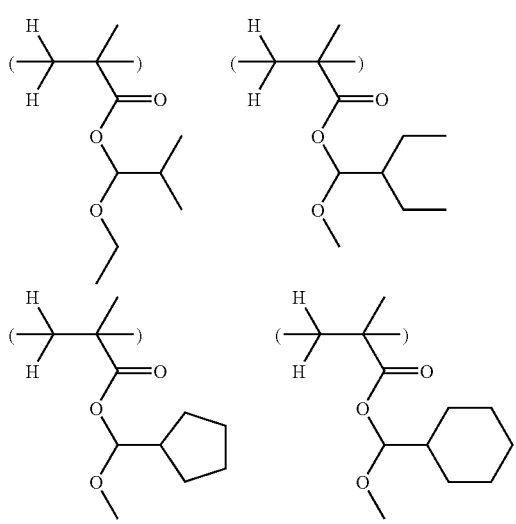
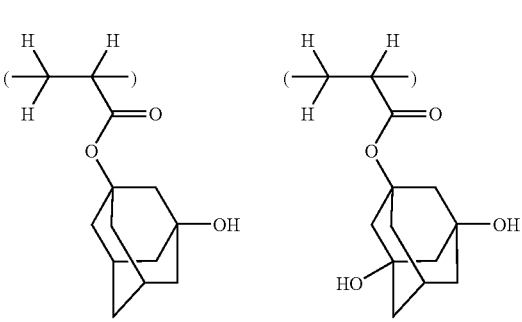

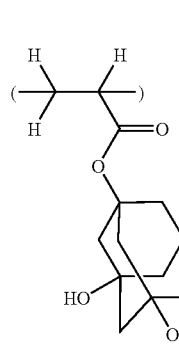 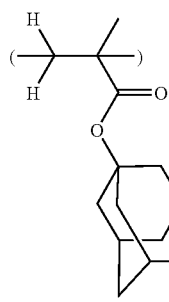 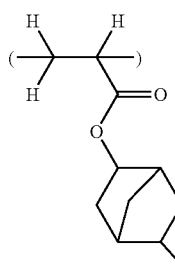 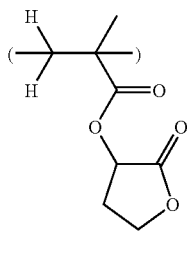
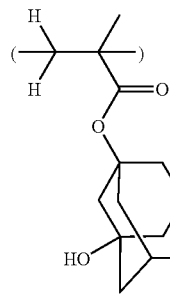 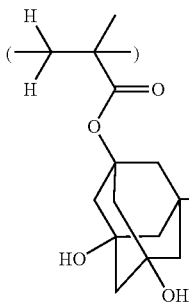 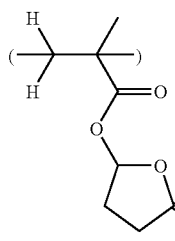
Illustrative examples of the recurring units of formula (6) are given below although the invention is not limited thereto.
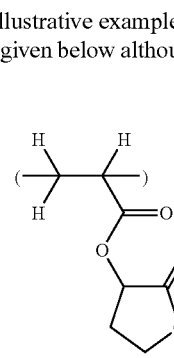 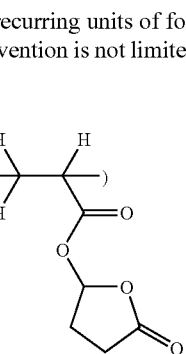 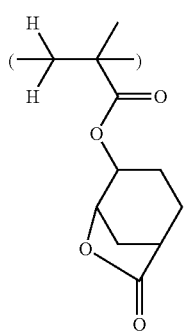 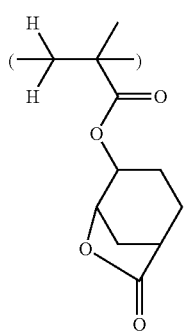
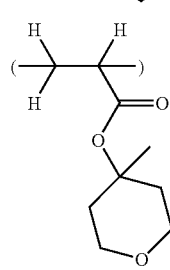 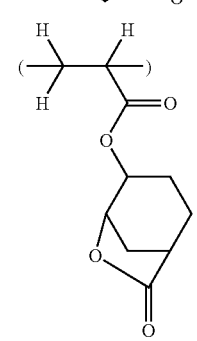 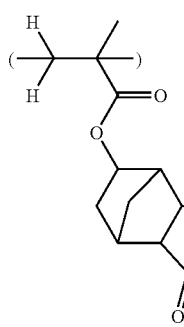 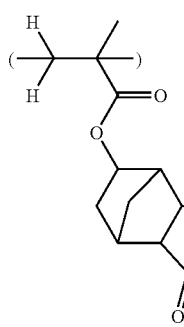
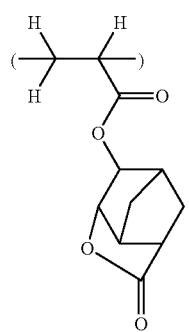 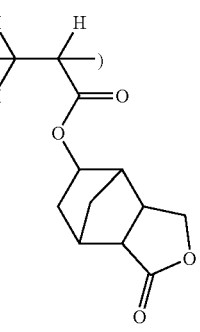 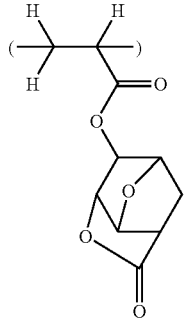 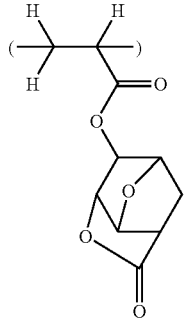

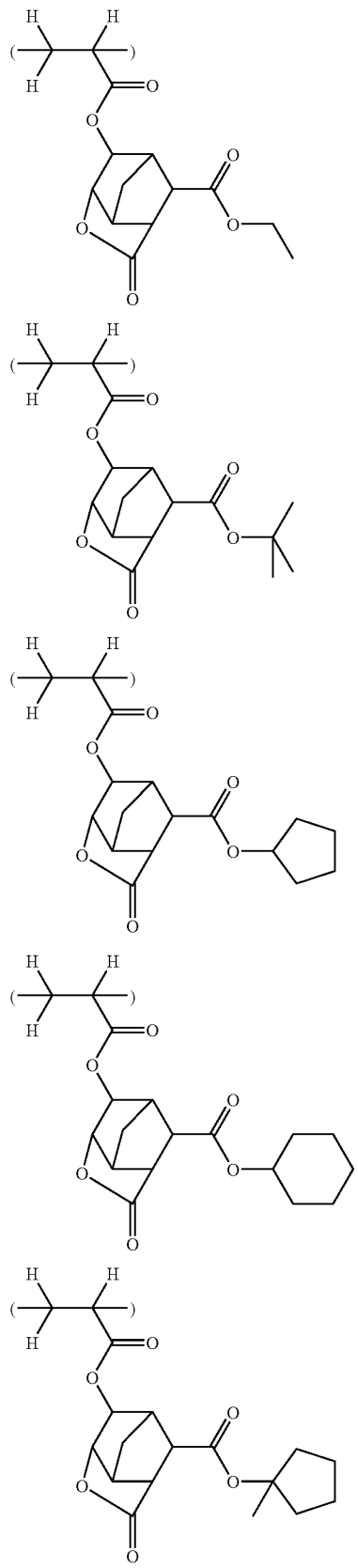
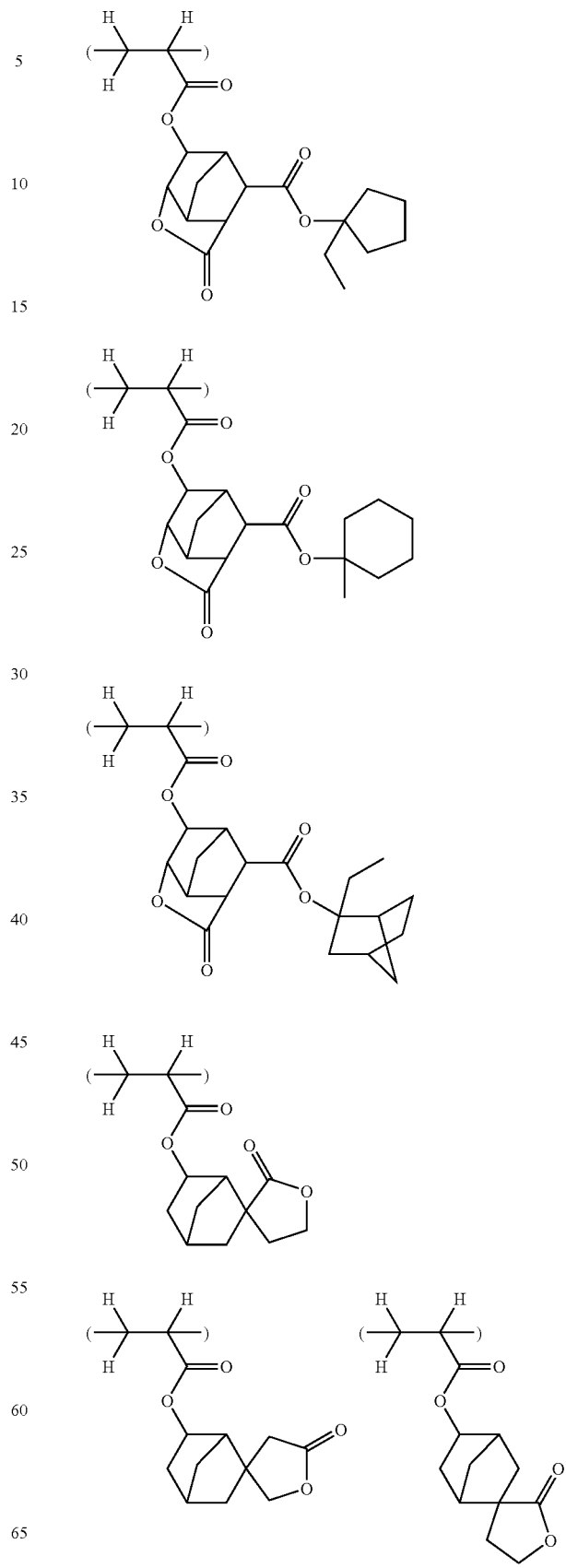

-continued
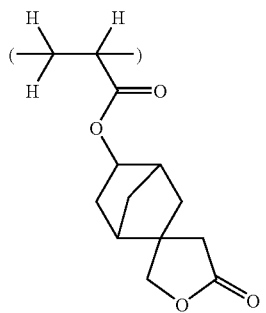 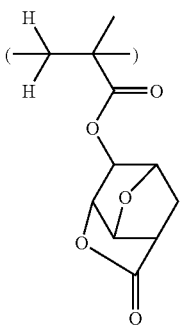
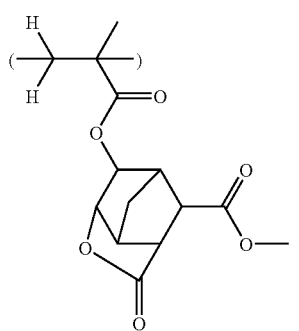
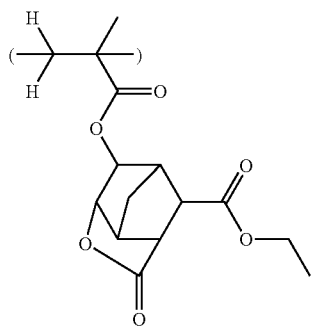
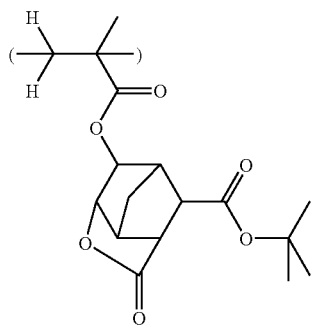
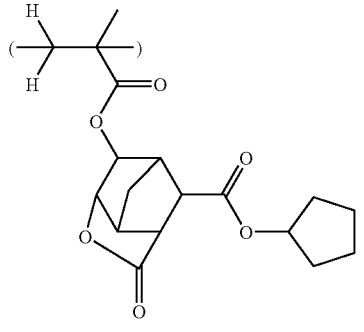
-continued
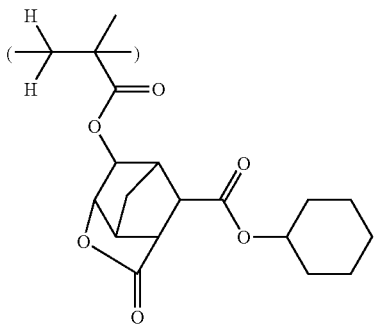
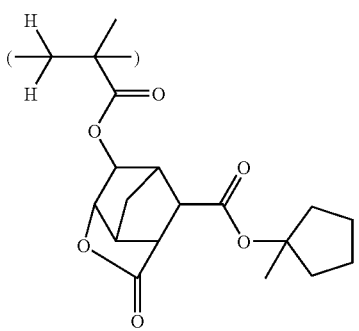
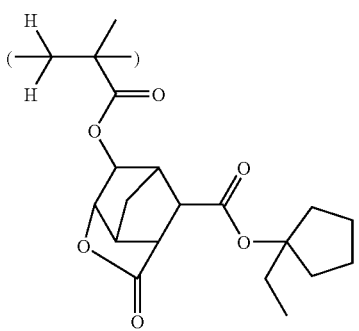
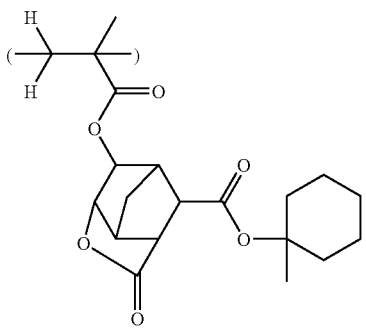
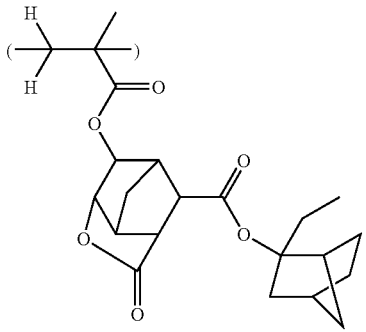

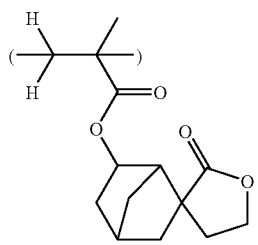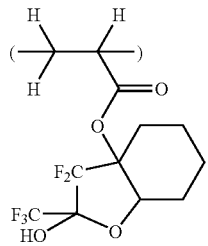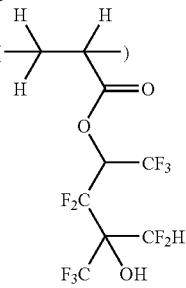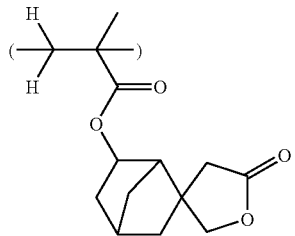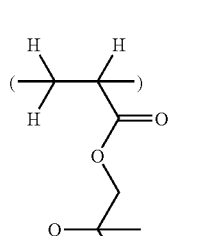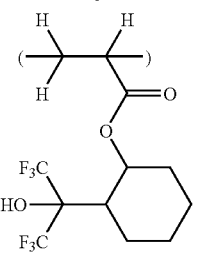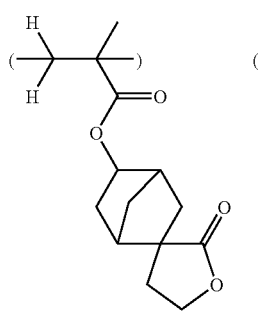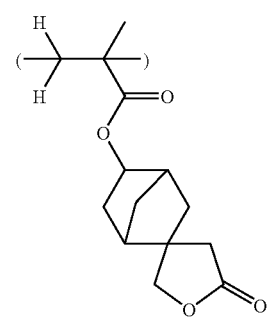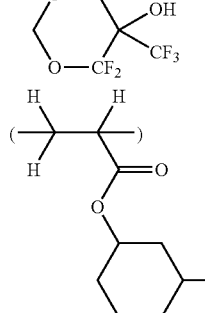
Illustrative examples of the recurring units of formula (7) are given below although the invention is not limited thereto.
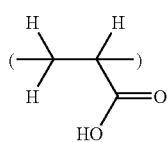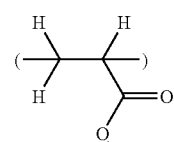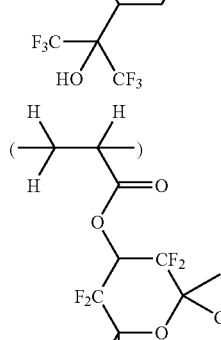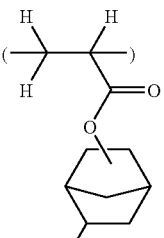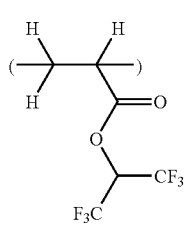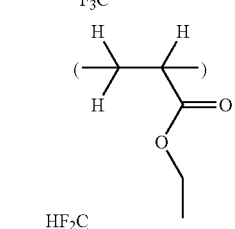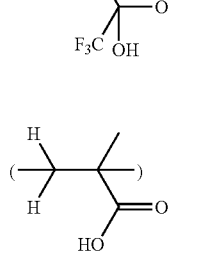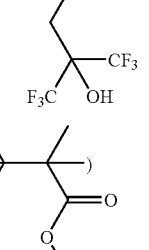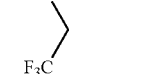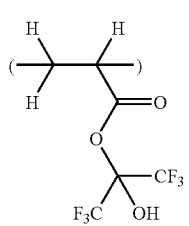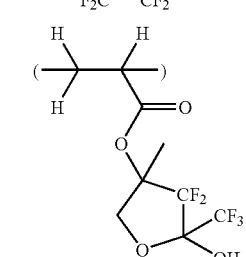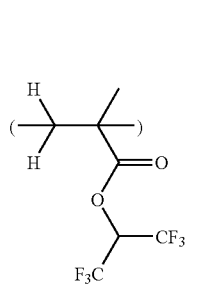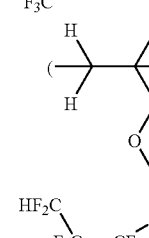

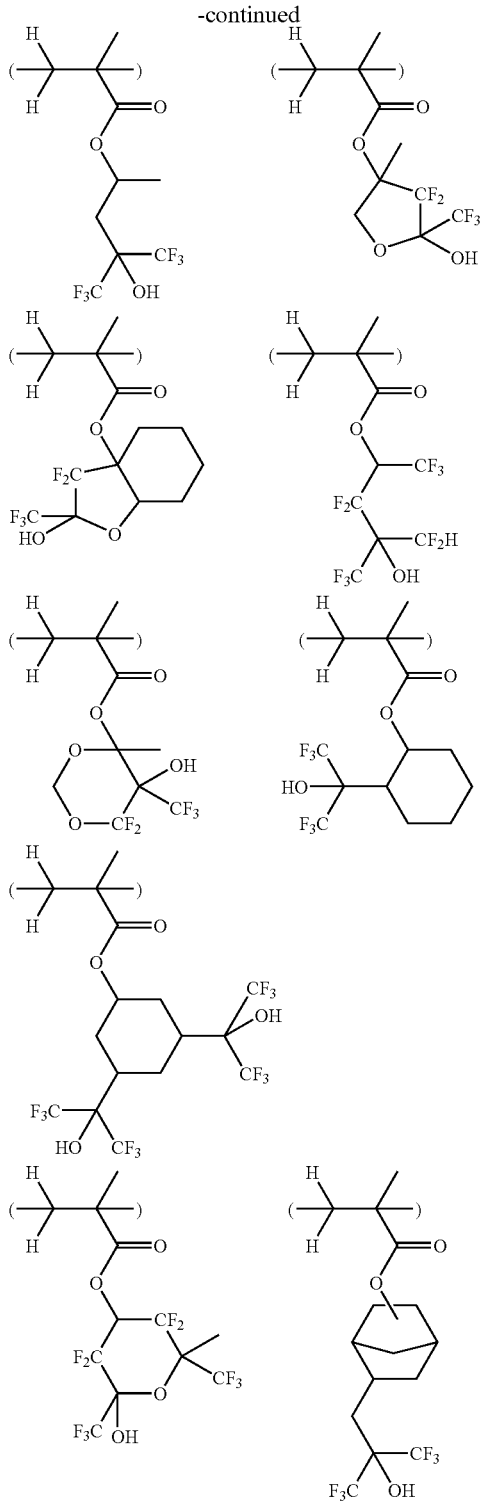

In addition to the foregoing units, the polymers of the invention may further comprise recurring units derived from carbon-to-carbon double bond-bearing monomers other than the above-described ones, for example, substituted acrylic acid esters such as methyl methacrylate, methyl chrotonate, dimethyl maleate and dimethyl itaconate, unsaturated carboxylic acids such as maleic acid, fumaric acid, and itaconic acid, cyclic olefins such as norbornene, norbornene derivatives, and tetracyclo[$4.4.0.1^{2,5}.17^{7,10}$]dodecene derivatives, unsaturated acid anhydrides such as itaconic anhydride, and other monomers.

The polymers of the invention generally have a weight average molecular weight (Mw) of 1,000 to 500,000, and preferably 3,000 to 100,000, as measured by gel permeation chromatography (GPC) using polystyrene standards. Outside the range, there may result an extreme drop of etch resistance, and a drop of resolution due to difficulty to gain a dissolution rate difference before and after exposure.

In the inventive polymers, appropriate proportions of the respective recurring units derived from the monomers are given below although the invention is not limited thereto. The inventive polymers may contain:

(I) constituent units of one or more types having formulas (1a) to (1c) derived from monomers of formulas (1) to (3) in a proportion of more than 0 mol % to 100 mol %, preferably 5 to 70 mol %, and more preferably 10 to 50 mol %, (II) constituent units of one or more types having formulas (4) to (7) in a proportion of 0 mol % to less than 100 mol %, preferably 1 to 95 mol %, and more preferably 20 to 80 mol %, and (III) constituent units of one or more types derived from other monomers in a proportion of 0 to 80 mol %, preferably 0 to 70 mol %, and more preferably 0 to 50 mol %, based on the total moles of constituent units.

The polymers of the invention are prepared by copolymerization reaction using the compound of formula (1) as a first monomer and polymerizable double bond-bearing compounds as second and subsequent monomers.

The copolymerization reaction to produce the inventive polymers may be performed in various modes, preferably radical polymerization, anionic polymerization or coordination polymerization.

For radical polymerization, preferred reaction conditions include (a) a solvent selected from among hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile and peroxides such as benzoyl peroxide and lauroyl peroxide, (c) a temperature of about 0° C. to about 100° C., and (d) a time of about ½ hour to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about ½ hour to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about ½ hour to about 48 hours. Reaction conditions outside the described range may be employed if desired.

Resist Composition Since the polymer of the invention is useful as the base resin of a resist composition, the other aspect of the invention provides a resist composition comprising the polymer and specifically a chemically amplified positive resist composition comprising the polymer. Typically, the resist composition contains (A) the inventive polymer as a base resin, (B) an acid generator, (C) an organic solvent, and optionally (D) an organic nitrogen-containing compound and (E) a surfactant.

In addition to the inventive polymer, the base resin (A) may include another polymer having a dissolution rate in alkaline developer that increases under the action of acid, if necessary. Examples of the other polymer include, but are not limited to, (i) poly(meth)acrylic acid derivatives, (ii) norbornene derivative-maleic anhydride copolymers, (iii) hydrogenated products of ring-opening metathesis polymers, and (iv) vinyl ether-maleic anhydride-(meth)acrylic acid derivative copolymers.

Of these, the hydrogenated products of ring-opening metathesis polymers are synthesized by the method illustrated in JP-A 15-66612. Illustrative examples of such hydrogenated polymers include those polymers having the recurring units shown below, but are not limited thereto.

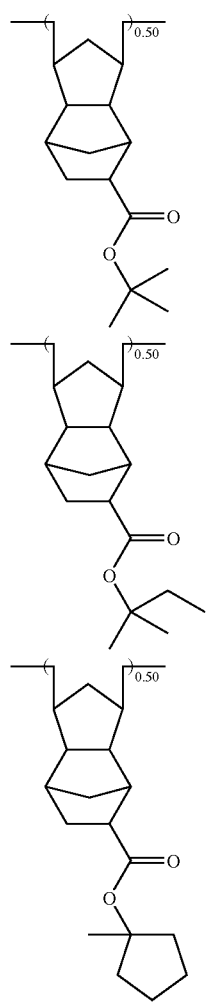

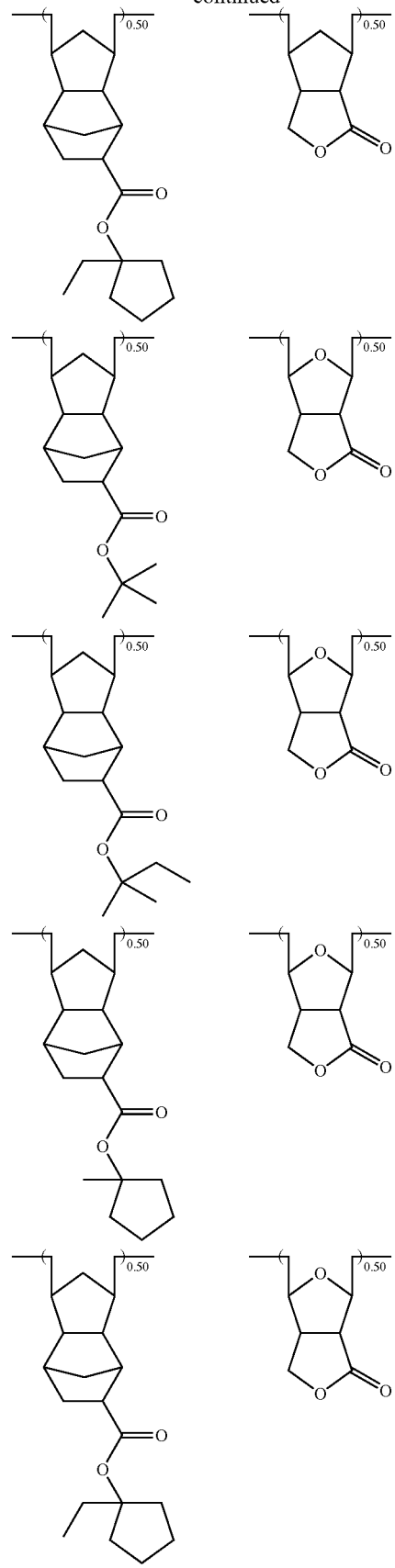

-continued
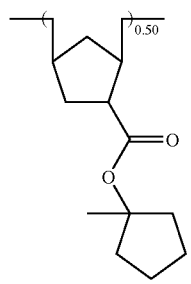 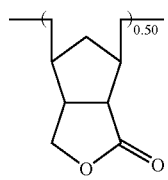
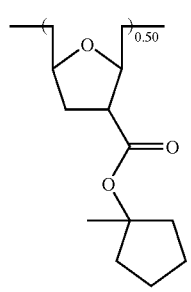 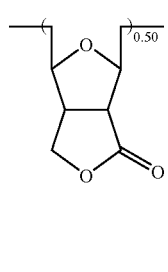
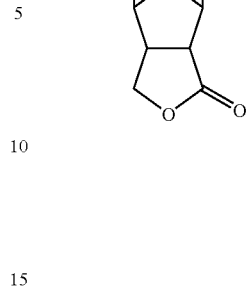
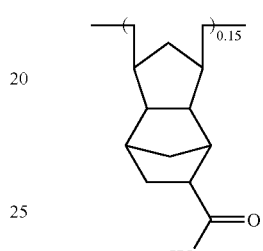 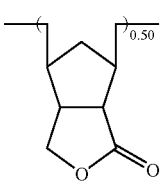
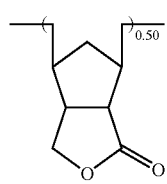
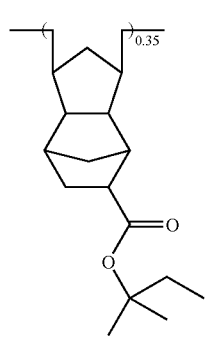
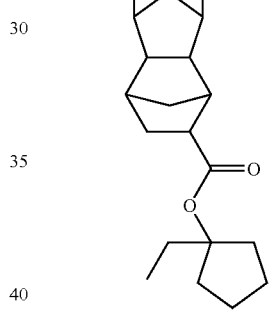 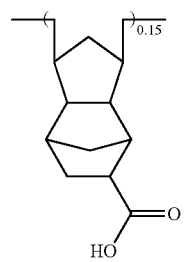
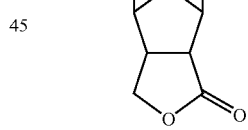
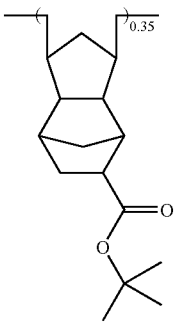
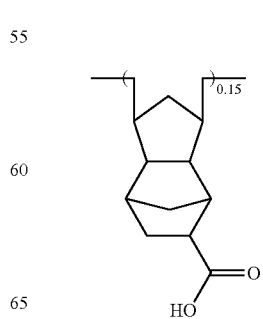 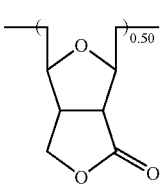

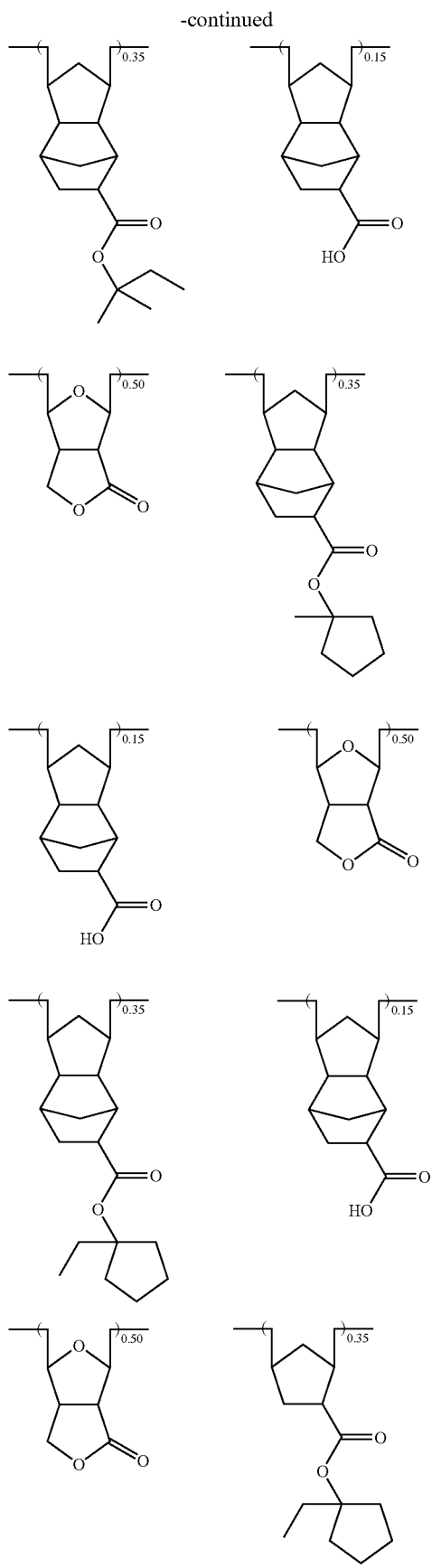
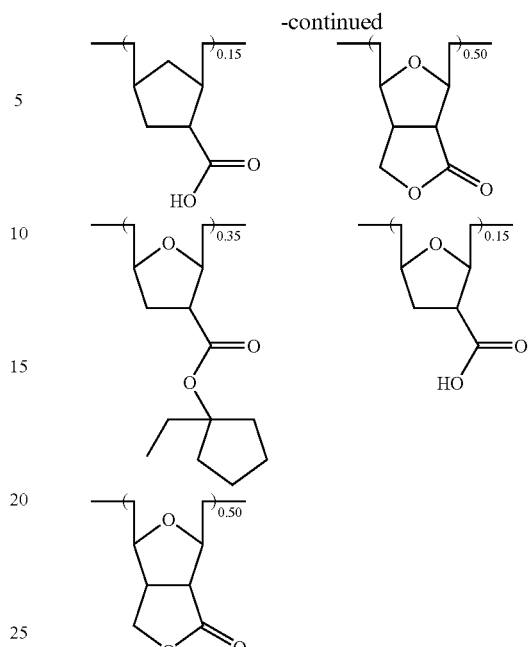

The inventive polymer and the other polymer are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer.

The other polymer is not limited to one type and a mixture of two or more other polymers may be added. The use of plural polymers allows for easy adjustment of resist properties.

Photoacid Generator

As the acid generator (B), a photoacid generator is typically used. It is any compound capable of generating an acid upon exposure to high-energy radiation. Suitable photoacid generators include sulfonium salts, iodonium salts, sulfonyldiazomethane, N-sulfonyloxyimide, and oxime-O-sulfonate acid generators. Exemplary acid generators are given below while they may be used alone or in admixture of two or more.

Sulfonium salts are salts of sulfonium cations with sulfonates, bis(substituted alkylsulfonyl)imides and tris(substituted alkylsulfonyl)methides. Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, dimethyl-2-naphthylsulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxo-2-phenylethylthiacyclopentanium, 4-n-butoxynaphthyl-1-thiacyclopentanium, and 2-n-butoxynaphthyl-1-thiacyclopentanium. Exemplary sulfonates include trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4'-toluenesulfonyloxy)benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl)-ethanesulfonate.

Exemplary bis(substituted alkylsulfonyl)imides include bis-trifluoromethylsulfonylimide, bispentafluoroethylsulfonylimide, bisheptafluoropropylsulfonylimide, and 1,3-propylenebissulfonylimide. A typical tris(substituted alkylsulfonyl)methide is tristrifluoromethylsulfonylmethide. Sulfonium salts based on combination of the foregoing examples are included.

Iodonium salts are salts of iodonium cations with sulfonates, bis(substituted alkylsulfonyl)imides and tris(substituted alkylsulfonyl)methides. Exemplary iodonium cations are aryliodonium cations including diphenyliodinium, bis(4-tert-butylphenyl)iodonium, 4-tert-butoxyphenylphenyliodonium, and 4-methoxyphenylphenyliodonium. Exemplary sulfonates include trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4-toluenesulfonyloxy)benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl)ethanesulfonate.

Exemplary bis(substituted alkylsulfonyl)-imides include bis-trifluoromethylsulfonylimide, bispentafluoroethylsulfonylimide, bisheptafluoropropylsulfonylimide, and 1,3-propylenebissulfonylimide. A typical tris(substituted alkylsulfonyl)methide is tristrifluoromethylsulfonylmethide. Iodonium salts based on combination of the foregoing examples are included.

Exemplary sulfonyldiazomethane compounds include bis-sulfonyldiazomethane compounds and sulfonyl-carbonyldiazomethane compounds such as bis(ethylsulfonyl)diazomethane, bis(1-methylpropylsulfonyl)diazomethane, bis(2-methylpropylsulfonyl)diazomethane, bis(1,1-dimethylethylsulfonyl)diazomethane, bis(cyclohexylsulfonyl)diazomethane, bis(perfluoroisopropylsulfonyl)diazomethane, bis(phenylsulfonyl)diazomethane, bis(4-methylphenylsulfonyl)diazomethane, bis(2,4-dimethylphenylsulfonyl)diazomethane, bis(2-naphthylsulfonyl)diazomethane, bis(4-acetyloxyphenylsulfonyl)diazomethane, bis(4-methanesulfonyloxyphenylsulfonyl)diazomethane, bis(4-(4-toluenesulfonyloxy)phenylsulfonyl)diazomethane, bis(4-(n-hexyloxy)phenylsulfonyl)diazomethane, bis(2-methyl-4-(n-hexyloxy)phenylsulfonyl)diazomethane, bis(2,5-dimethyl-4-(n-hexyloxy)phenylsulfonyl)diazomethane, bis(3,5-dimethyl-4-(n-hexyloxy)phenylsulfonyl)diazomethane, bis(2-methyl-5-isopropyl-4-(n-hexyloxy)phenylsulfonyl)-diazomethane, 4-methylphenylsulfonylbenzoyldiazomethane, tert-butylcarbonyl-4-methylphenylsulfonyldiazomethane, 2-naphthylsulfonylbenzoyldiazomethane, 4-methylphenylsulfonyl-2-naphthoyldiazomethane, methylsulfonylbenzoyldiazomethane, and tert-butoxycarbonyl-4-methylphenylsulfonyldiazomethane.

N-sulfonyloxyimide photoacid generators include combinations of imide skeletons with sulfonates. Exemplary imide skeletons are succinimide, naphthalene dicarboxylic acid imide, phthalimide, cyclohexyldicarboxylic acid imide, 5-norbornene-2,3-dicarboxylic acid imide, and 7-oxabicyclo[2.2.1]-5-heptene-2,3-dicarboxylic acid imide. Exemplary sulfonates include trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl)ethanesulfonate.

Benzoinsulfonate photoacid generators include benzoin tosylate, benzoin mesylate, and benzoin butanesulfonate.

Pyrogallol trisulfonate photoacid generators include pyrogallol, phloroglucinol, catechol, resorcinol, and hydroquinone, in which all the hydroxyl groups are substituted by trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl)ethanesulfonate.

Nitrobenzyl sulfonate photoacid generators include 2,4-dinitrobenzyl sulfonates, 2-nitrobenzyl sulfonates, and 2,6-dinitrobenzyl sulfonates, with exemplary sulfonates including trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl)ethanesulfonate. Also useful are analogous nitrobenzyl sulfonate compounds in which the nitro group on the benzyl side is substituted by a trifluoromethyl group.

Sulfone photoacid generators include bis(phenylsulfonyl)methane, bis(4-methylphenylsulfonyl)methane, bis(2-naphthylsulfonyl)methane, 2,2-bis(phenylsulfonyl)propane, 2,2-bis(4-methylphenylsulfonyl)propane, 2,2-bis(2-naphthylsulfonyl)propane, 2-methyl-2-(p-toluenesulfonyl)propiophenone, 2-cyclohexylcarbonyl-2-(p-toluenesulfonyl)propane, and 2,4-dimethyl-2-(p-toluenesulfonyl)pentan-3-one.

Photoacid generators in the form of glyoxime derivatives are described in Japanese Patent No. 2,906,999 and JP-A 9-301948 and include bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedioneglyoxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-(methanesulfonyl)-α-dimethylglyoxime, bis-O-(trifluoromethanesulfonyl)-α-dimethylglyoxime, bis-O-(2,2,2-trifluoroethanesulfonyl)-α-dimethylglyoxime, bis-O-(10-camphorsulfonyl)-α-dimethylglyoxime, bis-O-(benzenesulfonyl)-α-dimethylglyoxime, bis-O-(p-fluorobenzenesulfonyl)-α-dimethylglyoxime, bis-O-(p-trifluoromethylbenzenesulfonyl)-α-dimethylglyoxime, bis-O-(xylenesulfonyl)-α-dimethylglyoxime, bis-O-(trifluoromethanesulfonyl)-nioxime, bis-O-(2,2,2-trifluoroethanesulfonyl)-nioxime, bis-O-(10-camphorsulfonyl)-nioxime, bis-O-(benzenesulfonyl)-nioxime, bis-O-(p-fluorobenzenesulfonyl)-nioxime, bis-O-(p-trifluoromethylbenzenesulfonyl)-nioxime, and bis-O-(xylenesulfonyl)-nioxime.

Also included are the oxime sulfonates described in U.S. Pat. No. 6,004,724, for example, (5-(4-toluenesulfonyl)oxyimino-5H-thiophen-2-ylidene)phenyl-acetonitrile, (5-(10-camphorsulfonyl)oxyimino-5H-thiophen-2-ylidene)phenyl-acetonitrile, (5-n-octanesulfonyloxyimino-5H-thiophen-2-ylidene)phenyl-acetonitrile, (5-(4-toluenesulfonyl)oxyimino-5H-thiophen-2-ylidene)(2-methylphenyl)acetonitrile, (5-(10-camphorsulfonyl)oxyimino-5H-thiophen-2-ylidene)(2-methylphenyl)acetonitrile, (5-n-octanesulfonyloxyimino-5H-thiophen-2-ylidene)(2-methylphenyl)acetonitrile, etc. Also included are the oxime sulfonates described in U.S. Pat. No. 6,916,591, for example, (5-(4-(4-toluenesulfonyloxy)benzenesulfonyl)oxyimino-5H-thiophen-2-ylidene)phenylacetonitrile and (5-(2,5-bis(4-toluenesulfonyloxy)benzenesulfonyl)oxyimino-5H-thiophen-2-ylidene)phenylacetonitrile.

Also included are the oxime sulfonates described in U.S. Pat. No. 6,261,738 and JP-A 2000-314956, for example, 2,2,2-trifluoro-1-phenyl-ethanone oxime-O-methylsulfonate; 2,2,2-trifluoro-1-phenyl-ethanone oxime-O-(10-camphorylsulfonate); 2,2,2-trifluoro-1-phenyl-ethanone oxime-O-(4-methoxyphenylsulfonate); 2,2,2-trifluoro-1-phenyl-ethanone oxime-O-(1-naphthylsulfonate); 2,2,2-trifluoro-1-phenyl-ethanone oxime-O-(2-naphthylsulfonate); 2,2,2-trifluoro-1-phenyl-ethanone oxime-O-(2,4,6-trimethylphenylsulfonate); 2,2,2-trifluoro-1-(4-methylphenyl)-ethanone oxime-O-(10-camphorylsulfonate); 2,2,2-trifluoro-1-(4-methylphenyl)-ethanone oxime-O-(methylsulfonate); 2,2,2-trifluoro-1-(2-methylphenyl)-ethanone oxime-O-(10-camphorylsulfonate); 2,2,2-trifluoro-1-(2,4-dimethylphenyl)-ethanone oxime-O-(10-camphorylsulfonate); 2,2,2-trifluoro-1-(2,4-dimethylphenyl)-ethanone oxime-O-(1-naphthylsulfonate); 2,2,2-trifluoro-1-(2,4-dimethylphenyl)-ethanone oxime-O-(2-naphthylsulfonate); 2,2,2-trifluoro-1-(2,4,6-trimethylphenyl)-ethanone oxime-O-(10-camphorylsulfonate); 2,2,2-trifluoro-1-(2,4,6-trimethylphenyl)-ethanone oxime-O-(1-naphthylsulfonate); 2,2,2-trifluoro-1-(2,4,6-trimethylphenyl)-ethanone oxime-O-(2-naphthylsulfonate); 2,2,2-trifluoro-1-(4-methoxyphenyl)-ethanone oxime-O-methylsulfonate; 2,2,2-trifluoro-1-(4-methylthiophenyl)-ethanone oxime-O-methylsulfonate; 2,2,2-trifluoro-1-(3,4-dimethoxyphenyl)-ethanone oxime-O-methylsulfonate; 2,2, 3,3,4,4,4-heptafluoro-1-phenyl-butanone oxime-O-(10-camphorylsulfonate); 2,2,2-trifluoro-1-(phenyl)-ethanone oxime-O-methylsulfonate; 2,2,2-trifluoro-1-(phenyl)-ethanone oxime-O-10-camphorylsulfonate; 2,2,2-trifluoro-1-(phenyl)-ethanone oxime-O-(4-methoxyphenyl)sulfonate; 2,2,2-trifluoro-1-(phenyl)-ethanone oxime-O-(1-naphthyl)sulfonate; 2,2,2-trifluoro-1-(phenyl)-ethanone oxime-O-(2-naphthyl)sulfonate; 2,2,2-trifluoro-1-(phenyl)-ethanone oxime-O-(2,4,6-trimethylphenyl)sulfonate; 2,2,2-trifluoro-1-(4-methylphenyl)-ethanone oxime-O-(10-camphoryl)sulfonate; 2,2,2-trifluoro-1-(4-methylphenyl)-ethanone oxime-O-methylsulfonate; 2,2,2-trifluoro-1-(2-methylphenyl)-ethanone oxime-O-(10-camphoryl)sulfonate; 2,2,2-trifluoro-1-(2,4-dimethylphenyl)-ethanone oxime-O-(1-naphthyl)sulfonate; 2,2,2-trifluoro-1-(2,4-dimethylphenyl)-ethanone oxime-O-(2-naphthyl)sulfonate; 2,2,2-trifluoro-1-(2,4,6-trimethylphenyl)-ethanone oxime-O-(10-camphoryl)sulfonate; 2,2,2-trifluoro-1-(2,4,6-trimethylphenyl)-ethanone oxime-O-(1-naphthyl)-sulfonate; 2,2,2-trifluoro-1-(2,4,6-trimethylphenyl)-ethanone oxime-O-(2-naphthyl)sulfonate; 2,2,2-trifluoro-1-(4-methoxyphenyl)-ethanone oxime-O-methylsulfonate; 2,2,2-trifluoro-1-(4-thiomethylphenyl)-ethanone oxime-O-methylsulfonate; 2,2,2-trifluoro-1-(3,4-dimethoxyphenyl)-ethanone oxime-O-methylsulfonate; 2,2,2-trifluoro-1-(4-methoxyphenyl)-ethanone oxime-O-(4-methylphenyl)sulfonate; 2,2,2-trifluoro-1-(4-methoxyphenyl)-ethanone oxime-O-(4-methoxyphenyl)sulfonate; 2,2,2-trifluoro-1-(4-methoxyphenyl)-ethanone oxime-O-(4-dodecylphenyl)sulfonate; 2,2,2-trifluoro-1-(4-methoxyphenyl)-ethanone oxime-O-octylsulfonate; 2,2,2-trifluoro-1-(4-thiomethylphenyl)-ethanone oxime-O-(4-methoxyphenyl)sulfonate; 2,2,2-trifluoro-1-(4-thiomethylphenyl)-ethanone oxime-O-(4-dodecylphenyl)sulfonate; 2,2,2-trifluoro-1-(4-thiomethylphenyl)-ethanone oxime-O-octylsulfonate; 2,2,2-trifluoro-1-(4-thiomethylphenyl)-ethanone oxime-O-(2-naphthyl)sulfonate; 2,2,2-trifluoro-1-(2-methylphenyl)-ethanone oxime-O-methylsulfonate; 2,2,2-trifluoro-1-(4-methylphenyl)ethanone oxime-O-phenylsulfonate; 2,2,2-trifluoro-1-(4-chlorophenyl)-ethanone oxime-O-phenylsulfonate; 2,2,3,3,4,4,4-heptafluoro-1-(phenyl)-butanone oxime-O-(10-camphoryl) sulfonate; 2,2,2-trifluoro-1-naphthyl-ethanone oxime-O-methylsulfonate; 2,2,2-trifluoro-2-naphthyl-ethanone oxime-O-methylsulfonate; 2,2,2-trifluoro-1-[4-benzylphenyl]-ethanone oxime-O-methylsulfonate; 2,2,2-trifluoro-1-[4-(phenyl-1,4-dioxa-but-1-yl)phenyl]-ethanone oxime-O-methylsulfonate; 2,2,2-trifluoro-1-naphthyl-ethanone oxime-O-propylsulfonate; 2,2,2-trifluoro-2-naphthyl-ethanone oxime-O-propylsulfonate; 2,2,2-trifluoro-1-[4-benzylphenyl]-ethanone oxime-O-propylsulfonate; 2,2,2-trifluoro-1-[4-methylsulfonylphenyl]-ethanone oxime-O-propylsulfonate; 1,3-bis[1-(4-phenoxyphenyl)-2,2,2-trifluoro-ethanone oxime-O-sulfonyl]phenyl; 2,2,2-trifluoro-1-[4-methylsulfonyloxyphenyl]-ethanone oxime-O-propylsulfonate; 2,2,2-trifluoro-1-[4-methylcarbonyloxyphenyl]-ethanone oxime-O-propylsulfonate; 2,2,2-trifluoro-1-[6H,7H-5,8-dioxonaphth-2-yl]-ethanone oxime-O-propylsulfonate; 2,2,2-trifluoro-1-[4-methoxycarbonylmethoxyphenyl]-ethanone oxime-O-propyl-sulfonate; 2,2,2-trifluoro-1-[4-(methoxycarbonyl)-(4-amino-1-oxa-pent-1-yl)-phenyl]-ethanone oxime-O-propylsulfonate; 2,2,2-trifluoro-1-[3,5-dimethyl-4-ethoxyphenyl]-ethanone oxime-O-propylsulfonate; 2,2,2-trifluoro-1-[4-benzyloxy-phenyl]-ethanone oxime-O-propylsulfonate; 2,2,2-trifluoro-1-[2-thiophenyl]-ethanone oxime-O-propylsulfonate; 2,2,2-trifluoro-1-[1-dioxa-thiophen-2-yl)]-ethanone oxime-O-propylsulfonate; 2,2,2-trifluoro-1-(4-(3-(4-(2,2,2-trifluoro-1-(trifluoromethane-sulfonyloxyimino)-ethyl)-phenoxy)-propoxy)-phenyl) ethanone oxime(trifluoromethanesulfonate); 2,2,2-trifluoro-1-(4-(3-(4-(2,2,2-trifluoro-1-(1-propanesulfonyloxyimino)-ethyl)-phenoxy)-propoxy)-phenyl)ethanone oxime(1-propanesulfonate); and 2,2,2-trifluoro-1-(4-(3-(4-(2,2,2-trifluoro-1-(1-butanesulfonyloxyimino)-ethyl)-phenoxy)-propoxy)-phenyl)ethanone oxime(1-butanesulfonate). Also included are the oxime sulfonates described in U.S. Pat. No. 6,916,591, for example, 2,2,2-trifluoro-1-(4-(3-(4-(2,2,2-trifluoro-1-(4-(4-methylphenylsulfonyloxy)phenylsulfonyloxyimino)-ethyl)-phenoxy)-propoxy)-phenyl)ethanone oxime(4-(4-methylphenylsulfonyloxy)phenylsulfonate) and 2,2,2-trifluoro-1-(4-(3-(4-(2,2,2-trifluoro-1-(2,5-bis(4-methylphenylsulfonyloxy)benzenesulfonyloxy)-phenylsulfonyloxyimino)-ethyl)-phenoxy)-propoxy)-phenyl)ethanone oxime(2,5-bis(4-methylphenylsulfonyloxy)-benzenesulfonyloxy)phenylsulfonate).

Also included are the oxime sulfonates described in JP-A 9-95479 and JP-A 9-230588 and the references cited therein, for example, α-(p-toluenesulfonyloxyimino)-phenylacetonitrile, α-(p-chlorobenzenesulfonyloxyimino)-phenylacetonitrile, α-(4-nitrobenzenesulfonyloxyimino)-phenylacetonitrile, α-(4-nitro-2-trifluoromethylbenzenesulfonyloxyimino)-phenylacetonitrile, α-(benzenesulfonyloxyimino)-4-chlorophenylacetonitrile, α-(benzenesulfonyloxyimino)-2,4-dichlorophenylacetonitrile, α-(benzenesulfonyloxyimino)-2,6-dichlorophenylacetonitrile, α-(benzenesulfonyloxyimino)-4-methoxyphenylacetonitrile, α-(2-chlorobenzenesulfonyloxyimino)-4-methoxyphenyl-acetonitrile, α-(benzenesulfonyloxyimino)-2-thienylacetonitrile, α-(4-dodecylbenzenesulfonyloxyimino)-phenylacetonitrile, α-[(4-toluenesulfonyloxyimino)-4-methoxyphenyl]acetonitrile, α-[(dodecylbenzenesulfonyloxyimino)-4-methoxyphenyl]-acetonitrile, α-(tosyloxyimino)-3-thienylacetonitrile, α-(methylsulfonyloxyimino)-1-cyclopentenylacetonitrile, α-(ethylsulfonyloxyimino)-1-cyclopentenylacetonitrile, α-(isopropylsulfonyloxyimino)-1-cyclopentenylacetonitrile, α-(n-butylsulfonyloxyimino)-1-cyclopentenylacetonitrile, α-(ethylsulfonyloxyimino)-1-cyclohexenylacetonitrile, α-(isopropylsulfonyloxyimino)-1-cyclohexenylacetonitrile, and α-(n-butylsulfonyloxyimino)-1-cyclohexenylacetonitrile.

Also included are oxime sulfonates having the formula:

$$\begin{array}{c} OR^{s1} \\ | \\ N \\ || \\ Ar^{s1}-C-R^{s2} \end{array}$$

wherein $R^{s1}$ is a substituted or unsubstituted haloalkylsulfonyl or halobenzenesulfonyl group of 1 to 10 carbon atoms, $R^{s2}$ is a haloalkyl group of 1 to 11 carbon atoms, and $Ar^{s1}$ is substituted or unsubstituted aromatic or hetero-aromatic group, as described in WO 2004/074242.

Examples include 2-[2,2,3,3,4,4,5,5-octafluoro-1-(nonafluorobutylsulfonyloxy-imino)-pentyl]-fluorene, 2-[2,2,3,3,4,4-pentafluoro-1-(nonafluorobutylsulfonyloxy-imino)-butyl]-fluorene, 2-[2,2,3,3,4,4,5,5,6,6-decafluoro-1-(nonafluorobutylsulfonyl-oxyimino)-hexyl]-fluorene, 2-[2,2,3,3,4,4,5,5-octafluoro-1-(nonafluorobutylsulfonyloxyimino)-pentyl]-4-biphenyl, 2-[2,2,3,3,4,4-pentafluoro-1-(nonafluorobutylsulfonyloxy-imino)-butyl]-4-biphenyl, and 2-[2,2,3,3,4,4,5,5,6,6-decafluoro-1-(nonafluorobutylsulfonyl-oxyimino)-hexyl]-4-biphenyl.

Suitable bisoxime sulfonates include those described in JP-A 9-208554, for example, bis(α-(4-toluenesulfonyloxy)imino)-p-phenylenediacetonitrile, bis(α-(benzenesulfonyloxy)imino)-p-phenylenediacetonitrile, bis(α-(methanesulfonyloxy)imino)-p-phenylenediacetonitrile, bis(α-(butanesulfonyloxy)imino)-p-phenylenediacetonitrile, bis (α-(10-camphorsulfonyloxy)imino)-p-phenylenediacetonitrile, bis(α-(4-toluenesulfonyloxy) imino)-p-phenylenediacetonitrile, bis(α-(trifluoromethanesulfonyloxy)imino)-p-phenylenediacetonitrile, bis(α-(4-methoxybenzenesulfonyloxy)imino)-p-phenylenediaceto-nitrile, bis(α-(4-toluenesulfonyloxy)imino)-m-phenylenediacetonitrile, bis(α-(benzenesulfonyloxy)imino)-m-phenylenediacetonitrile, bis(α-(methanesulfonyloxy)imino)-m-phenylenediacetonitrile, bis(α-(butanesulfonyloxy)imino)-m-phenylenediacetonitrile, bis(α-(10-camphorsulfonyloxy)imino)-m-phenylenediacetonitrile, bis(α-(4-toluenesulfonyloxy)imino)-m-phenylenediacetonitrile, bis(α-(trifluoromethanesulfonyloxy)imino)-m-phenylenediaceto-nitrile, bis(α-(4-methoxybenzenesulfonyloxy)imino)-m-phenylenediaceto-nitrile, etc.

Of these, preferred photoacid generators are sulfonium salts, bissulfonyldiazomethanes, N-sulfonyloxyimides, oxime-O-sulfonates and glyoxime derivatives. More preferred photoacid generators are sulfonium salts, bissulfonyldiazomethanes, N-sulfonyloxyimides, and oxime-O-sulfonates. Typical examples include triphenylsulfonium p-toluenesulfonate, triphenylsulfonium camphorsulfonate, triphenylsulfonium pentafluorobenzenesulfonate, triphenylsulfonium nonafluorobutanesulfonate, triphenylsulfonium 4-(4'-toluenesulfonyloxy)benzenesulfonate, triphenylsulfonium 2,4,6-triisopropylbenzenesulfonate, 4-tert-butoxyphenyldiphenylsulfonium p-toluenesulfonate, 4-tert-butoxyphenyldiphenylsulfonium camphorsulfonate, 4-tert-butoxyphenyldiphenylsulfonium 4-(4'-toluenesulfonyl-oxy)benzenesulfonate, tris(4-methylphenyl)sulfonium camphorsulfonate, tris(4-tert-butylphenyl)sulfonium camphorsulfonate, 4-tert-butylphenyldiphenylsulfonium camphorsulfonate, 4-tert-butylphenyldiphenylsulfonium nonafluoro-1-butane-sulfonate, 4-tert-butylphenyldiphenylsulfonium pentafluoroethyl-perfluorocyclohexanesulfonate, 4-tert-butylphenyldiphenylsulfonium perfluoro-1-octane-sulfonate, triphenylsulfonium 1,1-difluoro-2-naphthyl-ethanesulfonate, triphenylsulfonium 1,1,2,2-tetrafluoro-2-(norbornan-2-yl)-ethanesulfonate, bis(tert-butylsulfonyl)diazomethane, bis(cyclohexylsulfonyl)diazomethane, bis(2,4-dimethylphenylsulfonyl)diazomethane, bis(4-(n-hexyloxy)phenylsulfonyl)diazomethane, bis(2-methyl-4-(n-hexyloxy)phenylsulfonyl)diazomethane, bis(2,5-dimethyl-4-(n-hexyloxy)phenylsulfonyl)diazomethane, bis(3,5-dimethyl-4-(n-hexyloxy)phenylsulfonyl)diazomethane, bis(2-methyl-5-isopropyl-4-(n-hexyloxy)phenylsulfonyl)-diazomethane, bis(4-tert-butylphenylsulfonyl)diazomethane, N-camphorsulfonyloxy-5-norbornene-2,3-dicarboxylic acid imide, N-p-toluenesulfonyloxy-5-norbornene-2,3-dicarboxylic acid imide, 2-[2,2,3,3,4,4,5,5-octafluoro-1-(nonafluorobutylsulfonyloxy-imino)-pentyl]-fluorene, 2-[2,2,3,3,4,4-pentafluoro-1-(nonafluorobutylsulfonyloxy-imino)-butyl]-fluorene, and 2-[2,2,3,3,4,4,5,5,6,6-decafluoro-1-(nonafluorobutylsulfonyl-oxyimino)-hexyl]-fluorene.

In the resist composition, an appropriate amount of the photoacid generator is, but not limited to, 0.1 to 10 parts, and especially 0.1 to 5 parts by weight per 100 parts by weight of the base resin. Too high a proportion of the photoacid generator may give rise to problems of degraded resolution and foreign matter upon development and resist film peeling. The photoacid generators may be used alone or in admixture of two or more. The transmittance of the resist film can be controlled by using a photoacid generator having a low transmittance at the exposure wavelength and adjusting the amount of the photoacid generator added.

In the resist composition, there may be added a compound which is decomposed with an acid to generate an acid, that is, acid-amplifier compound. For these compounds, reference should be made to J. Photopolym. Sci. and Tech., 8, 43-44, 45-46 (1995), and ibid., 9, 29-30 (1996).

Examples of the acid-amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition, an appropriate amount of the acid-amplifier compound is up to 2 parts, and especially up to 1 part by weight per 100 parts by weight of the base resin. Excessive amounts of the acid-amplifier compound make diffusion control difficult, leading to degradation of resolution and pattern profile.

Organic Solvent

The organic solvent (C) used herein may be any organic solvent in which the base resin, acid generator, and other components are soluble. Illustrative, non-limiting, examples of the organic solvent include ketones such as cyclohexanone and methyl n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, propylene glycol monomethyl ether acetate, and mixtures thereof because the acid generator is most soluble therein.

An appropriate amount of the organic solvent used is about 200 to 1,000 parts, especially about 400 to 800 parts by weight per 100 parts by weight of the solids in the resist composition.

Nitrogen-Containing Compound

In the resist composition, an organic nitrogen-containing compound or compounds (D) may be compounded. The organic nitrogen-containing compound used herein is preferably a compound capable of suppressing the rate of diffusion when the acid generated by the acid generator diffuses within the resist film. The inclusion of this type of organic nitrogen-containing compound holds down the rate of acid diffusion within the resist film, resulting in better resolution. In addition, it suppresses changes in sensitivity following exposure and reduces substrate and environment dependence, as well as improving the exposure latitude and the pattern profile.

Examples of organic nitrogen-containing compounds include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, imide derivatives, and carbamate derivatives.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl) pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds having carboxyl group include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable nitrogen-containing compounds having sulfonyl group include 3-pyridinesulfonic acid and pyridinium p-toluenesulfonate. Examples of suitable nitrogen-containing compounds having hydroxyl group, nitrogen-containing compounds having hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, benzamide, and 1-cyclohexylpyrrolidone. Suitable imide derivatives include phthalimide, succinimide, and maleimide. Suitable carbamate derivatives include N-t-butoxycarbonyl-N,N-dicyclohexylamine, N-t-butoxycarbonylbenzimidazole and oxazolidinone.

In addition, organic nitrogen-containing compounds of the following general formula (B)-1 may also be included alone or in admixture.

$$N(X)_n(Y)_{3-n} \quad \text{(B)-1}$$

In the formula, n is equal to 1, 2 or 3; side chain Y is independently hydrogen or a straight, branched or cyclic alkyl group of 1 to 20 carbon atoms which may contain an ether or hydroxyl group; and side chain X is independently selected from groups of the following general formulas (X)-1 to (X)-3, and two or three X's may bond together to form a ring.

(X1)

(X2)

(X3)

In the formulas, $R^{300}$, $R^{302}$ and $R^{305}$ are independently straight or branched alkylene groups of 1 to 4 carbon atoms; $R^{301}$ and $R^{304}$ are independently hydrogen, straight, branched or cyclic alkyl groups of 1 to 20 carbon atoms, which may contain at least one hydroxyl, ether, ester group or lactone ring; $R^{303}$ is a single bond or a straight or branched alkylene group of 1 to 4 carbon atoms; and $R^{306}$ is a straight, branched or cyclic alkyl group of 1 to 20 carbon atoms, which may contain at least one hydroxyl, ether, ester group or lactone ring.

Illustrative examples of the compounds of formula (B)-1 include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)-ethylamine, N,N-bis(2-hydroxyethyl)-2-[(2-oxotetrahydrofuran-3-yl)oxy-carbonyl]ethylamine, N,N-bis(2-acetoxyethyl)-2-[(2-oxotetrahydrofuran-3-yl)oxy-carbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)-ethylamine, N,N-bis(2-formyloxyethyl)-2-(2-formyloxyethoxycarbonyl)-ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis(2-methoxycarbonyloxyethyl)amine, N-ethyl-bis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis(methoxycarbonylmethyl)amine, and β-(diethylamino)-δ-valerolactone.

Also useful are one or more organic nitrogen-containing compounds having cyclic structure represented by the following general formula (B)-2.

(B)-2

Herein X is as defined above, and $R^{307}$ is a straight or branched alkylene group of 2 to 20 carbon atoms which may contain one or more carbonyl, ether, ester or sulfide groups.

Illustrative examples of the organic nitrogen-containing compounds having formula (B)-2 include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, and 2-methoxyethyl morpholinoacetate.

Also, one or more organic nitrogen-containing compounds having cyano group represented by the following general formulae (B)-3 to (B)-6 may be blended.

(B)-3

(B)-4

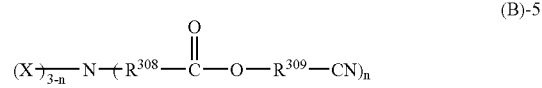

(B)-5

-continued

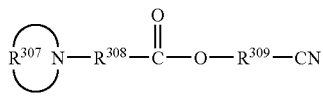
(B)-6

Herein, X, $R^{307}$ and n are as defined above, and $R^{308}$ and $R^{309}$ are each independently a straight or branched alkylene group of 1 to 4 carbon atoms.

Illustrative examples of the organic nitrogen-containing compounds having cyano represented by formulae (B)-3 to (B)-6 include
3-(diethylamino)propiononitrile,
N,N-bis(2-hydroxyethyl)-3-aminopropiononitrile,
N,N-bis(2-acetoxyethyl)-3-aminopropiononitrile,
N,N-bis(2-formyloxyethyl)-3-aminopropiononitrile,
N,N-bis(2-methoxyethyl)-3-aminopropiononitrile,
N,N-bis[2-(methoxymethoxy)ethyl]-3-aminopropiononitrile,
methyl N-(2-cyanoethyl)-N-(2-methoxyethyl)-3-aminopropionate,
methyl N-(2-cyanoethyl)-N-(2-hydroxyethyl)-3-aminopropionate,
methyl N-(2-acetoxyethyl)-N-(2-cyanoethyl)-3-aminopropionate,
N-(2-cyanoethyl)-N-ethyl-3-aminopropiononitrile,
N-(2-cyanoethyl)-N-(2-hydroxyethyl)-3-aminopropiononitrile,
N-(2-acetoxyethyl)-N-(2-cyanoethyl)-3-aminopropiononitrile,
N-(2-cyanoethyl)-N-(2-formyloxyethyl)-3-aminopropiononitrile,
N-(2-cyanoethyl)-N-(2-methoxyethyl)-3-aminopropiononitrile,
N-(2-cyanoethyl)-N-[2-(methoxymethoxy)ethyl]-3-aminopropiono-nitrile,
N-(2-cyanoethyl)-N-(3-hydroxy-1-propyl)-3-aminopropiononitrile,
N-(3-acetoxy-1-propyl)-N-(2-cyanoethyl)-3-aminopropiononitrile,
N-(2-cyanoethyl)-N-(3-formyloxy-1-propyl)-3-aminopropiononitrile,
N-(2-cyanoethyl)-N-tetrahydrofurfuryl-3-aminopropiononitrile,
N,N-bis(2-cyanoethyl)-3-aminopropiononitrile,
diethylaminoacetonitrile,
N,N-bis(2-hydroxyethyl)aminoacetonitrile,
N,N-bis(2-acetoxyethyl)aminoacetonitrile,
N,N-bis(2-formyloxyethyl)aminoacetonitrile,
N,N-bis(2-methoxyethyl)aminoacetonitrile,
N,N-bis[2-(methoxymethoxy)ethyl]aminoacetonitrile,
methyl N-cyanomethyl-N-(2-methoxyethyl)-3-aminopropionate,
methyl N-cyanomethyl-N-(2-hydroxyethyl)-3-aminopropionate,
methyl N-(2-acetoxyethyl)-N-cyanomethyl-3-aminopropionate,
N-cyanomethyl-N-(2-hydroxyethyl)aminoacetonitrile,
N-(2-acetoxyethyl)-N-(cyanomethyl)aminoacetonitrile,
N-cyanomethyl-N-(2-formyloxyethyl)aminoacetonitrile,
N-cyanomethyl-N-(2-methoxyethyl)aminoacetonitrile,
N-cyanomethyl-N-[2-(methoxymethoxy)ethyl]aminoacetonitrile,
N-cyanomethyl-N-(3-hydroxy-1-propyl)aminoacetonitrile,
N-(3-acetoxy-1-propyl)-N-(cyanomethyl)aminoacetonitrile,
N-cyanomethyl-N-(3-formyloxy-1-propyl)aminoacetonitrile,
N,N-bis(cyanomethyl)aminoacetonitrile,
1-pyrrolidinepropiononitrile, 1-piperidinepropiononitrile,
4-morpholinepropiononitrile, 1-pyrrolidineacetonitrile,
1-piperidineacetonitrile, 4-morpholineacetonitrile,
cyanomethyl 3-diethylaminopropionate,
cyanomethyl N,N-bis(2-hydroxyethyl)-3-aminopropionate,
cyanomethyl N,N-bis(2-acetoxyethyl)-3-aminopropionate,
cyanomethyl N,N-bis(2-formyloxyethyl)-3-aminopropionate,
cyanomethyl N,N-bis(2-methoxyethyl)-3-aminopropionate,
cyanomethyl N,N-bis[2-(methoxymethoxy)ethyl]-3-aminopropionate,
2-cyanoethyl 3-diethylaminopropionate,
2-cyanoethyl N,N-bis(2-hydroxyethyl)-3-aminopropionate,
2-cyanoethyl N,N-bis(2-acetoxyethyl)-3-aminopropionate,
2-cyanoethyl N,N-bis(2-formyloxyethyl)-3-aminopropionate,
2-cyanoethyl N,N-bis(2-methoxyethyl)-3-aminopropionate,
2-cyanoethyl N,N-bis[2-(methoxymethoxy)ethyl]-3-aminopropionate,
cyanomethyl 1-pyrrolidinepropionate,
cyanomethyl 1-piperidinepropionate,
cyanomethyl 4-morpholinepropionate,
2-cyanoethyl 1-pyrrolidinepropionate,
2-cyanoethyl 1-piperidinepropionate, and
2-cyanoethyl 4-morpholinepropionate.

Also included are organic nitrogen-containing compounds having an imidazole structure and a polar functional group, represented by the general formula (B)-7.

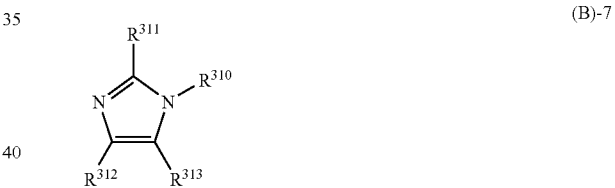
(B)-7

Herein, $R^{310}$ is a straight, branched or cyclic alkyl group of 2 to 20 carbon atoms bearing at least one polar functional group selected from among hydroxyl, carbonyl, ester, ether, sulfide, carbonate, cyano and acetal groups; $R^{311}$, $R^{312}$ and $R^{313}$ are each independently a hydrogen atom, a straight, branched or cyclic alkyl group, aryl group or aralkyl group having 1 to 10 carbon atoms.

Also included are organic nitrogen-containing compounds having a benzimidazole structure and a polar functional group, represented by the general formula (B)-8.

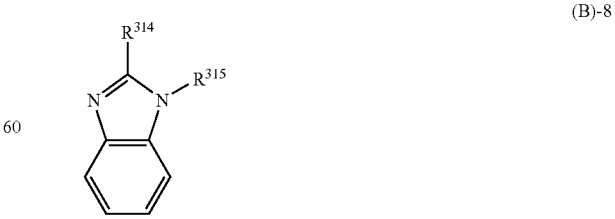
(B)-8

Herein, $R^{314}$ is a hydrogen atom, a straight, branched or cyclic alkyl group, aryl group or aralkyl group having 1 to 10 carbon atoms. $R^{315}$ is a polar functional group-bearing, straight, branched or cyclic alkyl group of 1 to 20 carbon atoms, and the alkyl group contains as the polar functional group at least one group selected from among ester, acetal and cyano groups, and may additionally contain at least one group selected from among hydroxyl, carbonyl, ether, sulfide and carbonate groups.

Further included are heterocyclic nitrogen-containing compounds having a polar functional group, represented by the general formulae (B)-9 and (B)-10.

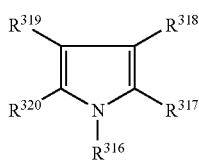

(B)-9

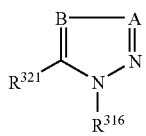

(B)-10

Herein, A is a nitrogen atom or $=C-R^{322}$, B is a nitrogen atom or $=C-R^{323}$, $R^{316}$ is a straight, branched or cyclic alkyl group of 2 to 20 carbon atoms bearing at least one polar functional group selected from among hydroxyl, carbonyl, ester, ether, sulfide, carbonate, cyano and acetal groups; $R^{317}$, $R^{318}$, $R^{319}$ and $R^{320}$ are each independently a hydrogen atom, a straight, branched or cyclic alkyl group or aryl group having 1 to 10 carbon atoms, or a pair of $R^{317}$ and $R^{318}$ and a pair of $R^{319}$ and $R^{320}$, taken together, may form a benzene, naphthalene or pyridine ring; $R^{321}$ is a hydrogen atom, a straight, branched or cyclic alkyl group or aryl group having 1 to 10 carbon atoms; $R^{322}$ and $R^{323}$ each are a hydrogen atom, a straight, branched or cyclic alkyl group or aryl group having 1 to 10 carbon atoms, or a pair of $R^{321}$ and $R^{323}$, taken together, may form a benzene or naphthalene ring.

Also included are organic nitrogen-containing compounds of aromatic carboxylic ester structure having the general formulae (B)-11 to (B)-14.

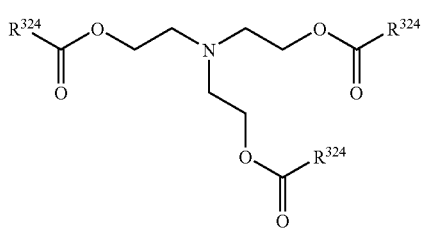

(B)-11

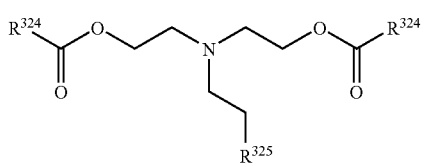

(B)-12

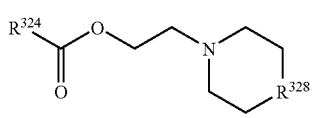

(B)-13

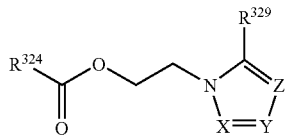

(B)-14

Herein $R^{324}$ is a $C_6$-$C_{20}$ aryl group or $C_4$-$C_{20}$ hetero-aromatic group, in which some or all of hydrogen atoms may be replaced by halogen atoms, straight, branched or cyclic $C_1$-$C_{20}$ alkyl groups, $C_6$-$C_{20}$ aryl groups, $C_1$-$C_{20}$ aralkyl groups, $C_1$-$C_{10}$ alkoxy groups, $C_1$-$C_{10}$ acyloxy groups or $C_1$-$C_{10}$ alkylthio groups. $R^{325}$ is $CO_2R^{326}$, $OR^{327}$ or cyano group. $R^{326}$ is a $C_1$-$C_{10}$ alkyl group, in which some methylene groups may be replaced by oxygen atoms. $R^{327}$ is a $C_1$-$C_{10}$ alkyl or acyl group, in which some methylene groups may be replaced by oxygen atoms. $R^{328}$ is a single bond, methylene, ethylene, sulfur atom or $-O(CH_2CH_2O)_n-$ group wherein n is 0, 1, 2, 3 or 4. $R^{329}$ is hydrogen, methyl, ethyl or phenyl. X is a nitrogen atom or $CR^{330}$. Y is a nitrogen atom or $CR^{331}$. Z is a nitrogen atom or $CR^{332}$. $R^{330}$, $R^{331}$ and $R^{332}$ are each independently hydrogen, methyl or phenyl. Alternatively, a pair of $R^{330}$ and $R^{331}$ or a pair of $R^{331}$ and $R^{332}$ may bond together to form a $C_6$-$C_{20}$ aromatic ring or $C_2$-$C_{20}$ hetero-aromatic ring.

Further included are organic nitrogen-containing compounds of 7-oxanorbornane-2-carboxylic ester structure having the general formula (B)-15.

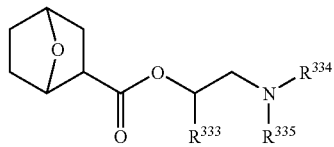

(B)-15

Herein $R^{333}$ is hydrogen or a straight, branched or cyclic $C_1$-$C_{10}$ alkyl group. $R^{334}$ and $R^{335}$ are each independently a $C_1$-$C_{20}$ alkyl group, $C_6$-$C_{20}$ aryl group or $C_7$-$C_{20}$ aralkyl group, which may contain one or more polar functional groups selected from among ether, carbonyl, ester, alcohol, sulfide, nitrile, amine, imine, and amide and in which some hydrogen atoms may be replaced by halogen atoms. $R^{334}$ and $R^{335}$, taken together, may form a heterocyclic or hetero-aromatic ring of 2 to 20 carbon atoms.

The organic nitrogen-containing compounds may be used alone or in admixture of two or more. The organic nitrogen-containing compound is preferably formulated in an amount of 0.001 to 2 parts, and especially 0.01 to 1 part by weight, per 100 parts by weight of the entire base resin. Less than 0.001 part of the nitrogen-containing compound achieves no or little addition effect whereas more than 2 parts would result in too low a sensitivity.

The resist composition of the invention may include optional ingredients, for example, a surfactant which is commonly used for improving the coating characteristics. Optional ingredients may be added in conventional amounts so long as this does not compromise the objects of the invention.

Nonionic surfactants are preferred, examples of which include perfluoroalkylpolyoxyethylene ethanols, fluorinated alkyl esters, perfluoroalkylamine oxides, perfluoroalkyl EO-addition products, and fluorinated organosiloxane compounds. Useful surfactants are commercially available under the trade names Fluorad FC-430 and FC-431 from Sumitomo 3M, Ltd., Surflon S-141, S-145, KH-10, KH-20, KH-30 and KH-40 from Asahi Glass Co., Ltd., Unidyne DS-401, DS-403 and DS-451 from Daikin Industry Co., Ltd., Megaface F-8151 from Dai-Nippon Ink & Chemicals, Inc., and X-70-092 and X-70-093 from Shin-Etsu Chemical Co., Ltd. Preferred surfactants are Fluorad FC-430 from Sumitomo 3M, Ltd., KH-20 and KH-30 from Asahi Glass Co., Ltd., and X-70-093 from Shin-Etsu Chemical Co., Ltd.

While the resist composition of the invention typically comprises a polymer, acid generator, organic solvent and organic nitrogen-containing compound as described above, there may be added optional other ingredients such as dissolution inhibitors, acidic compounds, stabilizers, and dyes. Optional ingredients may be added in conventional amounts so long as this does not compromise the objects of the invention.

Pattern formation using the resist composition of the invention may be carried out by a known lithographic technique. For example, the resist composition is applied onto a substrate such as a silicon wafer by spin coating or the like to form a resist film having a thickness of 0.3 to 2.0 μm, which is then pre-baked on a hot plate at 60 to 150° C. for 1 to 10 minutes, and preferably at 80 to 140° C. for 1 to 5 minutes. A patterning mask having the desired pattern is then placed over the resist film, and the film exposed through the mask to an electron beam or to high-energy radiation such as deep-UV rays, an excimer laser, or x-rays in a dose of about 1 to 200 mJ/cm², and preferably about 10 to 100 mJ/cm². Light exposure may be done by a conventional exposure process or in some cases, by an immersion process of providing liquid (typically water) impregnation between the mask and the resist. The resist film is then post-exposure baked (PEB) on a hot plate at 60 to 150° C. for 1 to 5 minutes, and preferably at 80 to 140° C. for 1 to 3 minutes. Finally, development is carried out using as the developer an aqueous alkali solution, such as a 0.1 to 5 wt % (preferably 2 to 3 wt %) aqueous solution of tetramethylammonium hydroxide (TMAH), this being done by a conventional method such as dip, puddle, or spray development for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV rays having a wavelength of 250 to 190 nm, an excimer laser, x-rays, or an electron beam. The desired pattern may not be obtainable outside the upper and lower limits of the above range.

EXAMPLE

Synthesis Examples and Examples are given below by way of illustration and not by way of limitation. The abbreviation Mw is a weight average molecular weight as measured by GPC using polystyrene standards. PGMEA is propylene glycol monomethyl ether acetate.

Synthesis Example 1

Lactone-containing compounds within the scope of the invention were synthesized according to the following formulation.

Synthesis Example 1-1

Synthesis of Monomer 1

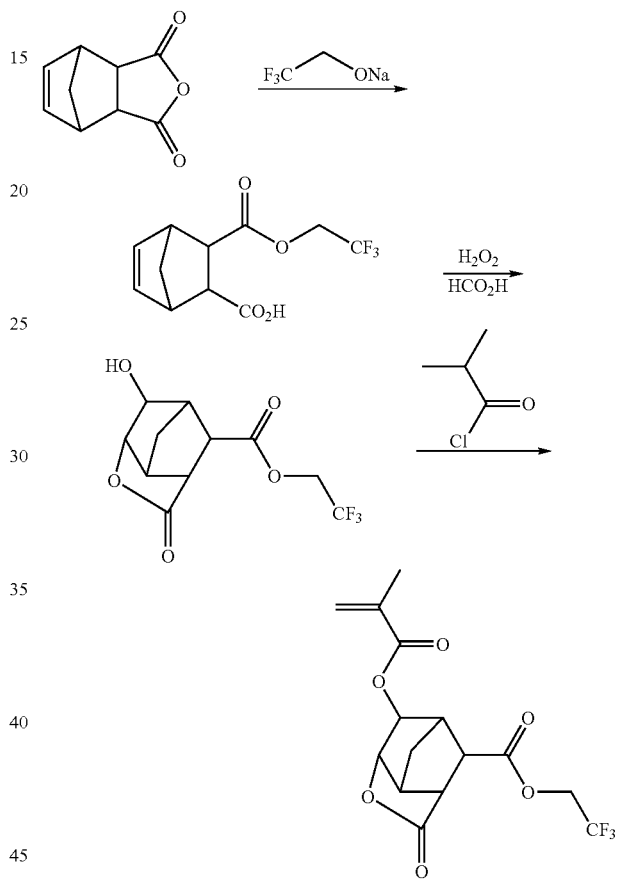

Synthesis Example 1-1-1

Synthesis of 3-(2,2,2-trifluoroethoxycarbonyl)-5-norbornene-2-carboxylic acid

A flask was charged with 13.8 g of sodium hydride (purity 60%) and 80 ml of tetrahydrofuran, to which 33.0 g of 1,1,1-trifluoroethanol was added dropwise at 30° C. After the completion of dropwise addition, the contents were stirred at the temperature for one hour. The flask was cooled at 10° C., and a mixture of 49.2 g of 5-norbornene-2,3-dicarboxylic acid anhydride and 150 ml of tetrahydrofuran was added dropwise. After the completion of dropwise addition, the contents were stirred at the temperature for one hour. Then 150 g of 10% hydrochloric acid was added to quench the reaction. This was followed by ordinary post-treatment and recrystallization from n-hexane, obtaining 69.8 g of the target compound (yield 88%).

$^1$H-NMR (600 MHz in CDCl$_3$): δ=1.51 (1H, dd), 1.61 (1H, d), 2.76 (1H, dd), 3.18 (1H, s), 3.33 (1H, s), 3.45 (1H, t), 4.42-4.48 (1H, m), 4.55-4.62 (1H, m), 6.14-6.17 (1H, m), 6.30-6.33 (1H, m) ppm Synthesis Example 1-1-2

Synthesis of 2,2,2-trifluoroethyl 6-hydroxy-2-oxo-hexahydro-3,5-methano-2H-cyclopenta[b]furan-7-carboxylate A flask was charged with 61.0 g of the half ester obtained in [1-1-1], 120 g of t-butylalcohol, and 20.0 g of formic acid. 42.3 g of 35% aqueous hydrogen peroxide was added dropwise at a temperature of 35 to 50° C. while monitoring the exothermic heat. After the completion of dropwise addition, the contents were stirred at the temperature for 8 hours. The flask was cooled at 10° C., and 30 g of sodium sulfite was added. This was followed by ordinary post-treatment and recrystallization from n-hexane, obtaining 54.4 g of the target compound (yield 84%).
$^1$H-NMR (600 MHz in DMSO-d$_6$): δ=1.45 (1H, dd), 1.92 (1H, d), 2.53 (1H, s), 2.82 (1H, d), 2.98 (1H, s), 3.18 (1H, t), 3.64 (1H, s), 4.31 (1H, d), 4.71-4.89 (2H, m), 5.39 (1H, d) ppm Synthesis Example 1-1-3

Synthesis of 7-(2,2,2-trifluoroethoxycarbonyl)-2-oxohexahydro-3,5-methano-2H-cyclopenta[b]furan-6-yl methacrylate In 200 ml of toluene were dissolved 40.0 g of the alcohol obtained in [1-1-2] and 20.3 g of triethylamine. To the solution at 10° C., 18.7 g of methacrylic acid chloride was added. The solution was stirred at the temperature for one hour. 100 ml of water was added below 30° C. This was followed by ordinary post-treatment and recrystallization from diisopropyl ether, obtaining 38.8 g of the target compound (yield 78%).
IR (thin film): ν=3018, 2985, 2962, 2939, 1791, 1756, 1722, 1417, 1324, 1301, 1286, 1160, 1108, 1074, 1043, 1020, 985 cm$^{-1}$
$^1$H-NMR (600 MHz in CDCl$_3$): δ=1.79 (1H, d), 1.94 (3H, s), 2.00 (1H, d), 2.92 (2H, d), 3.10 (1H, d-like), 3.28 (1H, t-like), 4.42-4.50 (1H, m), 4.55-4.65 (2H, m), 4.72 (1H, s), 5.64 (1H, t-like), 6.11 (1H, s) ppm
$^{19}$F-NMR (565 MHz in CDCl$_3$): δ=−74.5 (3F, dd) ppm Synthesis Example 1-2

Synthesis of Monomer 2

The procedure of Synthesis Example 1-1-3 was repeated aside from using acrylic acid chloride instead of methacrylic acid chloride. There was obtained 7-(2,2,2-trifluoroethoxy-carbonyl)-2-oxohexahydro-3,5-methano-2H-cyclopenta[b]furan-6-yl acrylate (yield 74%).

Synthesis Example 1-3

Synthesis of Monomer 3

The procedure of Synthesis Example 1-1-3 was repeated aside from using α-trifluoromethylacrylic acid chloride instead of methacrylic acid chloride. There was obtained 7-(2,2,2-trifluoroethoxycarbonyl)-2-oxohexahydro-3,5-methano-2H-cyclopenta[b]furan-6-yl α-trifluoromethylacrylate (yield 70%).

Synthesis Example 1-4

Synthesis of Monomer 4

The procedure of Synthesis Example 1-1-3 was repeated aside from using 5-norbornene-2-carboxylic acid chloride instead of methacrylic acid chloride. There was obtained 7-(2,2,2-trifluoroethoxycarbonyl)-2-oxohexahydro-3,5-methano-2H-cyclopenta[b]furan-6-yl 5-norbornene-2-carboxylate (yield 80%).

Synthesis Example 1-5

Synthesis of Monomer 5

The procedures of Synthesis Examples 1-1-1 to 1-1-3 were repeated aside from using 7-oxa-5-norbornene-2,3-dicarboxylic acid anhydride instead of 5-norbornene-2,3-dicarboxylic acid anhydride. There was obtained 7-(2,2,2-trifluoroethoxy-carbonyl)-2-oxo-4-oxahexahydro-3,5-methano-2H-cyclopenta[b]furan-6-yl methacrylate (three step yield 42%).

Synthesis Example 1-6

Synthesis of Monomer 6

The procedures of Synthesis Examples 1-1-1 to 1-1-3 were repeated aside from using 1,1,2,2-tetrafluoropropyl alcohol instead of 1,1,1-trifluoroethanol. There was obtained 7-(2,2,3,3-tetrafluoropropoxycarbonyl)-2-oxohexahydro-3,5-methano-2H-cyclopenta[b]furan-6-yl methacrylate (three step yield 51%).

Synthesis Example 1-7

Synthesis of Monomer 7

The procedures of Synthesis Examples 1-1-1 to 1-1-3 were repeated aside from using 1,1,2,2-tetrafluoropropyl alcohol instead of 1,1,1-trifluoroethanol and acrylic acid chloride instead of methacrylic acid chloride. There was obtained 7-(2,2,3,3-tetrafluoropropoxycarbonyl)-2-oxohexahydro-3,5-methano-2H-cyclopenta[b]furan-6-yl acrylate (three step yield 54%).

Synthesis Example 1-8

Synthesis of Monomer 8

The procedures of Synthesis Examples 1-1-1 to 1-1-3 were repeated aside from using 1,1,2,2-tetrafluoropropyl alcohol instead of 1,1,1-trifluoroethanol and α-trifluoromethylacrylic acid chloride instead of methacrylic acid chloride. There was obtained 7-(2,2,3,3-tetrafluoropropoxycarbonyl)-2-oxo-hexa-hydro-3,5-methano-2H-cyclopenta[b]furan-6-yl α-trifluoro-methylacrylate (three step yield 48%).

Synthesis Example 1-9

Synthesis of Monomer 9

The procedures of Synthesis Examples 1-1-1 to 1-1-3 were repeated aside from using 1,1,2,2-tetrafluoropropyl alcohol instead of 1,1,1-trifluoroethanol and 7-oxa-5-norbornene-2,3-dicarboxylic acid anhydride instead of 5-norbornene-2,3-dicarboxylic acid anhydride. There was obtained 7-(2,2,3,3-tetrafluoropropoxycarbonyl)-2-oxo-4-oxahexahydro-3,5-methano-2H-cyclopenta[b]furan-6-yl methacrylate (three step yield 47%).

Synthesis Example 1-10

Synthesis of Monomer 10

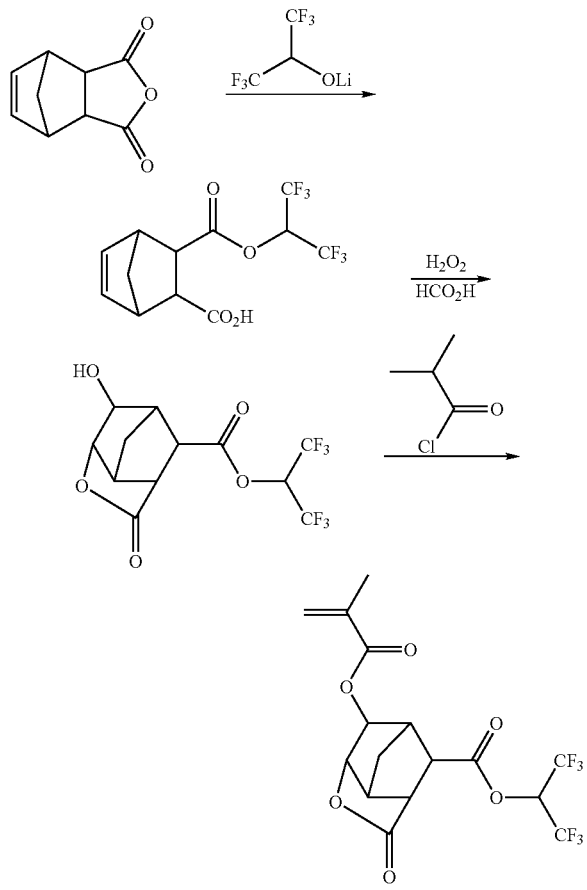

Synthesis Example 1-10-1

Synthesis of 3-(1,1,1,3,3,3-hexafluoroisopropoxycarbonyl)-5-norbornene-2-carboxylic acid A flask was charged with 223.5 g of 1,1,1,3,3,3-hexafluoroisopropyl alcohol and 500 ml of tetrahydrofuran, to which 500 ml of n-butyllithium in n-hexane (2.6 moles/L) was added dropwise at −10° C. After the completion of dropwise addition, the contents were stirred at room temperature for one hour. The flask was cooled at 10° C., and a mixture of 198.5 g of 5-norbornene-2,3-dicarboxylic acid anhydride and 600 ml of tetrahydrofuran was added dropwise. After the completion of dropwise addition, the contents were stirred at 60° C. for 10 hours. Then 500 g of 10% hydrochloric acid was added to quench the reaction. This was followed by ordinary post-treatment and recrystallization from n-hexane, obtaining 345.5 g of the target compound (yield 86%).

$^1$H-NMR (600 MHz in CDCl$_3$): δ=1.56 (2H, dt), 2.86 (1H, dd), 3.21 (1H, d-like), 3.37 (1H, d-like), 3.47 (1H, dd), 5.78 (1H, sept), 6.19 (1H, dd), 6.34 (1H, dd) ppm Synthesis Example 1-10-2

Synthesis of 1,1,1,3,3,3-hexafluoroisopropyl 6-hydroxy-2-oxohexahydro-3,5-methano-2H-cyclopenta[b]furan-7-carboxylate A flask was charged with 300.0 g of the half ester obtained in [1-10-1], 600 g of t-butylalcohol, and 103.9 g of formic acid. 263.2 g of 35% aqueous hydrogen peroxide was added dropwise at a temperature of 35 to 50° C. while monitoring the exothermic heat. After the completion of dropwise addition, the contents were stirred at the temperature for 8 hours. The flask was cooled at 10° C., and 200 g of sodium sulfite was added. This was followed by ordinary post-treatment and recrystallization from n-hexane, obtaining 235.8 g of the target compound (yield 75%).

$^1$H-NMR (600 MHz in DMSO-d$_6$): δ=1.38 (1H, dd), 1.96 (1H, d), 2.54 (1H, s), 2.83 (1H, dd), 3.23 (1H, dt), 3.28 (1H, s), 3.69 (1H, s), 4.34 (1H, d), 5.45 (1H, d), 6.88 (1H, sept) ppm Synthesis Example 1-10-3

Synthesis of 7-(1,1,1,3,3,3-hexafluoroisopropoxycarbonyl)-2-oxohexahydro-3,5-methano-2H-cyclopenta[b]furan-6-yl methacrylate In 300 ml of toluene and 200 ml of acetonitrile were dissolved 80.0 g of the alcohol obtained in [1-10-2] and 32.6 g of triethylamine. To the solution at 10° C., 30.0 g of methacrylic acid chloride was added. The solution was stirred at the temperature for one hour. 150 ml of water was added below 30° C. This was followed by ordinary post-treatment and recrystallization from diisopropyl ether, obtaining 66.0 g of the target compound (yield 69%).

IR (thin film): ν=2973, 2933, 1793, 1722, 1639, 1469, 1390, 1361, 1322, 1297, 1238, 1203, 1157, 1110, 1093, 1018, 946, 908 cm$^{-1}$ $^1$H-NMR (600 MHz in CDCl$_3$): δ=1.75 (1H, dd), 1.95 (3H, s), 2.04 (1H, dd), 2.92 (1H, s), 3.02 (1H, s), 3.13 (1H, d-like), 3.32 (1H, dt-like), 4.63 (1H, d), 4.76 (1H, d), 5.65 (1H, t-like), 5.76 (1H, sept), 6.12 (1H, s) ppm $^{19}$F-NMR (565 MHz in CDCl$_3$): δ=−73.8 to −73.9 (3F, m), −73.8 to −73.7 (3F, m) ppm Synthesis Example 1-11

Synthesis of Monomer 11

The procedure of Synthesis Example 1-10-3 was repeated aside from using acrylic acid chloride instead of methacrylic acid chloride. There was obtained 7-(1,1,1,3,3,3-hexafluoroisopropoxycarbonyl)-2-oxohexahydro-3,5-methano-2H-cyclopenta[b]furan-6-yl acrylate (yield 65%).

Synthesis Example 1-12

Synthesis of Monomer 12

The procedure of Synthesis Example 1-10-3 was repeated aside from using α-trifluoromethylacrylic acid chloride instead of methacrylic acid chloride. There was obtained 7-(1,1,1,3,3,3-hexafluoroisopropoxycarbonyl)-2-oxohexahydro-3,5-methano-2H-cyclopenta[b]furan-6-yl α-trifluoromethyl-acrylate (yield 65%).

Synthesis Example 1-13

Synthesis of Monomer 13

The procedures of Synthesis Examples 1-10-1 to 1-10-3 were repeated aside from using 7-oxa-5-norbornene-2,3-dicarboxylic acid anhydride instead of 5-norbornene-2,3-dicarboxylic acid anhydride. There was obtained 7-(1,1,1,3,3,3-hexafluoroisopropoxycarbonyl)-2-oxo-4-oxahexahydro-3,5-methano-2H-cyclopenta[b]furan-6-yl methacrylate (three step yield 41%).

Synthesis Example 1-14

Synthesis of Monomer 14

The procedures of Synthesis Examples 1-1-1 to 1-1-3 were repeated aside from using 2,2,3,3,4,4,5,5-octafluoro-1-pentanol instead of 1,1,1-trifluoroethanol. There was obtained 7-(2,2,3,3,4,4,5,5-octafluoro-1-pentyloxycarbonyl)-2-oxo-hexahydro-3,5-methano-2H-cyclopenta[b]furan-6-yl methacrylate (three step yield 49%).

IR (thin film): ν=2983, 2933, 1791, 1758, 1724, 1639, 1456, 1405, 1340, 1321, 1299, 1253, 1172, 1114, 1076, 1043, 1018, 946 cm$^{-1}$ $^{1}$H-NMR (600 MHz in CDCl$_3$): δ=1.12 (1H, d), 1.79 (1H, dd), 1.94 (3H, t), 2.00 (1H, dd), 2.91 (2H, d), 3.11 (1H, d-like), 3.28 (1H, dt-like), 4.54-4.62 (2H, m), 4.71-4.77 (2H, m), 5.63-5.64 (1H, m), 6.11 (1H, d-like) ppm $^{19}$F-NMR (565 MHz in CDCl$_3$): δ=−137.9 to −137.9 (2F, m), −130.5 to −130.4 (2F, m), −126.0 (2F, t-like), −120.5 to −120.3 (2F, m) ppm

Synthesis Example 1-15

Synthesis of Monomer 15

The procedures of Synthesis Examples 1-1-1 to 1-1-3 were repeated aside from using 2,2,3,3,4,4,5,5-octafluoro-1-pentanol instead of 1,1,1-trifluoroethanol and α-fluoroacrylic acid chloride instead of methacrylic acid chloride. There was obtained 7-(2,2,3,3,4,4,5,5-octafluoro-1-pentyloxycarbonyl)-2-oxohexahydro-3,5-methano-2H-cyclopenta[b]furan-6-yl α-fluoroacrylate (three step yield 42%).

Monomer 1

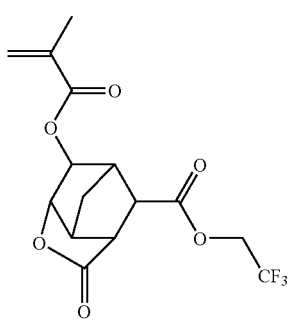

Monomer 2

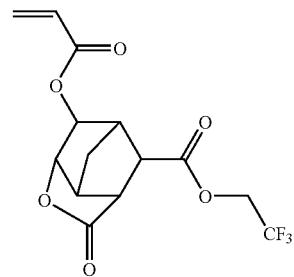

Monomer 3

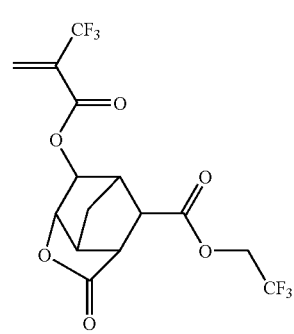

Monomer 4

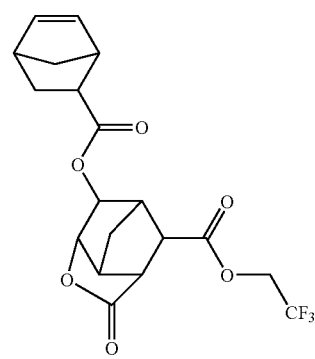

Monomer 5

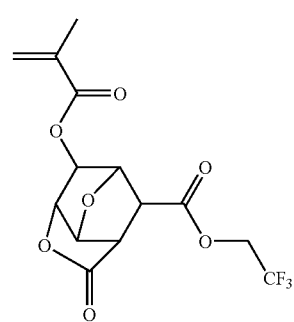

Monomer 6

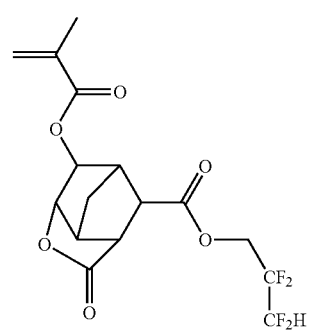

-continued
Monomer 7
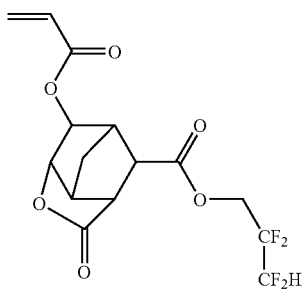
Monomer 8
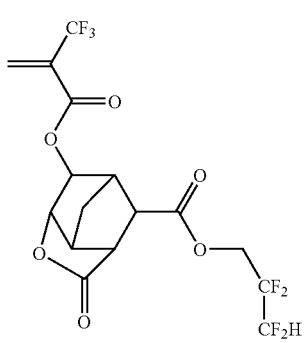
Monomer 9
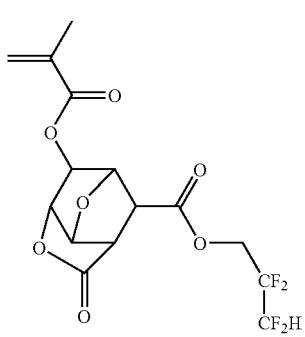
Monomer 10
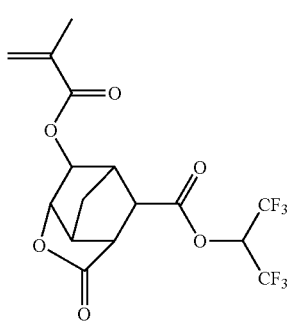
Monomer 11
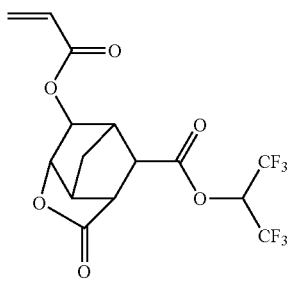
-continued
Monomer 12
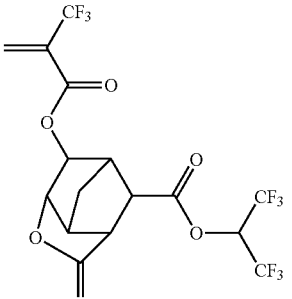
Monomer 13
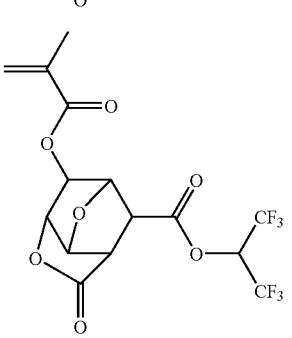
Monomer 14
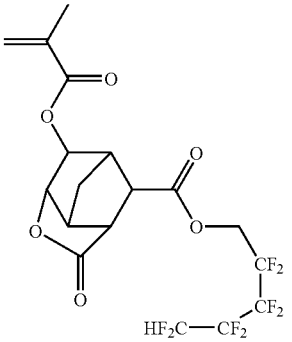
Monomer 15
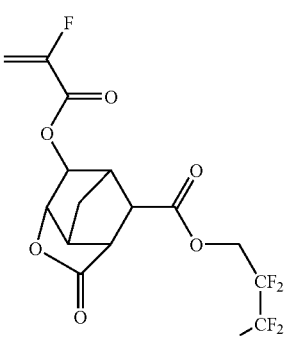
Synthesis Example 2
Polymers within the scope of the invention were synthesized according to the following formulation.
Synthesis Example 2-1
Synthesis of Polymer 1
In 87.5 g of PGMEA were dissolved 28.0 g of Monomer 1, 22.0 g of 3-ethyl-3-exo-tetracyclo[$4.4.0.1^{2,5}.1^{7,10}$]dodecanyl methacrylate, 1055 mg of 2,2'-azobisisobutyronitrile, and 126 mg of 2-mercaptoethanol. In a nitrogen atmosphere, with stirring, this solution was added dropwise over 4 hours to 29.2 g of PGMEA which was heated at 80° C. The solution was stirred at 80° C. for a further 2 hours. The reaction solution was cooled to room temperature, and with vigorous stirring, added dropwise to 1,000 ml of n-hexane. The resulting solids were collected by filtration and dried in vacuum at 50° C. for 15 hours, obtaining 43.5 g (yield 87%) of a white powder solid designated Polymer 1. Polymer 1 had the compositional proportion and Mw shown in Table 1.

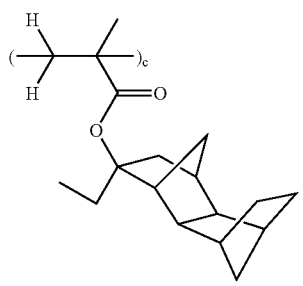

Polymer 1

-continued

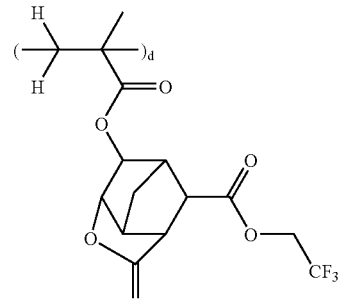

(c = 0.50, d = 0.50, Mw = 7,300)

Synthesis Examples 2-2 to 2-94 and Comparative Synthesis Examples 1-1 to 1-3

Synthesis of Polymers 2-97

Polymers 2 to 97 were synthesized by the same procedure as Synthesis Examples 2-1 except that the type and proportion of monomers were changed, with their compositional proportion and Mw being shown in Tables 1 and 2. The structure of the units is shown in Tables 3 to 6.

TABLE 1

| Synthesis Example | | Resin | Unit 1 (ratio) | Unit 2 (ratio) | Unit 3 (ratio) | Unit 4 (ratio) | Unit 5 (ratio) | Mw |
|---|---|---|---|---|---|---|---|---|
| | 2-1 | Polymer 1 | F-1M(0.50) | A-1M(0.50) | — | — | — | 7,300 |
| | 2-2 | Polymer 2 | F-2M(0.50) | A-1M(0.50) | — | — | — | 7,300 |
| | 2-3 | Polymer 3 | F-3M(0.50) | A-1M(0.50) | — | — | — | 6,700 |
| | 2-4 | Polymer 4 | F-4M(0.50) | A-1M(0.50) | — | — | — | 7,000 |
| | 2-5 | Polymer 5 | F-1M(0.40) | A-1M(0.35) | B-1M(0.25) | — | — | 7,100 |
| | 2-6 | Polymer 6 | F-1M(0.35) | A-2M(0.40) | B-1M(0.25) | — | — | 7,400 |
| | 2-7 | Polymer 7 | F-1M(0.40) | A-3M(0.35) | B-1M(0.25) | — | — | 6,900 |
| | 2-8 | Polymer 8 | F-1M(0.40) | A-4M(0.35) | B-1M(0.25) | — | — | 7,300 |
| | 2-9 | Polymer 9 | F-1M(0.35) | A-5M(0.40) | B-1M(0.25) | — | — | 6,500 |
| | 2-10 | Polymer 10 | F-1M(0.35) | A-6M(0.40) | B-1M(0.25) | — | — | 7,000 |
| | 2-11 | Polymer 11 | F-3M(0.40) | A-1M(0.35) | B-1M(0.25) | — | — | 7,300 |
| | 2-12 | Polymer 13 | F-3M(0.35) | A-2M(0.40) | B-1M(0.25) | — | — | 7,500 |
| | 2-13 | Polymer 13 | F-3M(0.40) | A-3M(0.35) | B-1M(0.25) | — | — | 7,000 |
| | 2-14 | Polymer 14 | F-3M(0.40) | A-4M(0.35) | B-1M(0.25) | — | — | 7,400 |
| | 2-15 | Polymer 15 | F-3M(0.35) | A-5M(0.40) | B-1M(0.25) | — | — | 6,600 |
| | 2-16 | Polymer 16 | F-3M(0.35) | A-6M(0.40) | B-1M(0.25) | — | — | 7,100 |
| | 2-17 | Polymer 17 | F-3M(0.40) | A-1M(0.35) | B-2M(0.25) | — | — | 6,700 |
| | 2-18 | Polymer 18 | F-3M(0.40) | A-3M(0.35) | B-2M(0.25) | — | — | 6,800 |
| | 2-19 | Polymer 19 | F-1A(0.40) | A-1M(0.35) | B-1M(0.25) | — | — | 6,800 |
| | 2-20 | Polymer 20 | F-1A(0.40) | A-1M(0.35) | B-1A(0.25) | — | — | 6,700 |
| | 2-21 | Polymer 21 | F-1M(0.20) | A-1M(0.35) | B-1M(0.25) | B-3M(0.20) | — | 6,600 |
| | 2-22 | Polymer 22 | F-1M(0.20) | A-2M(0.40) | B-1M(0.25) | B-3M(0.15) | — | 6,700 |
| | 2-23 | Polymer 23 | F-1M(0.20) | A-3M(0.35) | B-1M(0.25) | B-3M(0.20) | — | 6,500 |
| | 2-24 | Polymer 24 | F-1M(0.20) | A-4M(0.35) | B-1M(0.25) | B-3M(0.20) | — | 6,900 |
| | 2-25 | Polymer 25 | F-1M(0.20) | A-5M(0.40) | B-1M(0.25) | B-3M(0.15) | — | 7,000 |
| | 2-26 | Polymer 26 | F-1M(0.20) | A-6M(0.40) | B-1M(0.25) | B-3M(0.15) | — | 7,300 |
| | 2-27 | Polymer 27 | F-1M(0.20) | A-1M(0.35) | B-1M(0.25) | B-4M(0.20) | — | 6,900 |
| | 2-28 | Polymer 28 | F-1M(0.20) | A-1M(0.35) | B-1M(0.25) | B-5M(0.20) | — | 6,800 |
| | 2-29 | Polymer 29 | F-1M(0.20) | A-1M(0.35) | B-1M(0.25) | B-6M(0.20) | — | 6,700 |
| | 2-30 | Polymer 30 | F-1M(0.20) | A-1M(0.35) | B-1A(0.25) | B-3M(0.20) | — | 6,800 |
| | 2-31 | Polymer 31 | F-3M(0.20) | A-1M(0.35) | B-1M(0.25) | B-3M(0.20) | — | 7,300 |
| | 2-32 | Polymer 33 | F-3M(0.20) | A-2M(0.40) | B-1M(0.25) | B-3M(0.15) | — | 7,500 |
| | 2-33 | Polymer 33 | F-3M(0.20) | A-3M(0.35) | B-1M(0.25) | B-3M(0.20) | — | 7,100 |
| | 2-34 | Polymer 34 | F-3M(0.20) | A-4M(0.35) | B-1M(0.25) | B-3M(0.20) | — | 7,400 |
| | 2-35 | Polymer 35 | F-3M(0.20) | A-5M(0.40) | B-1M(0.25) | B-3M(0.15) | — | 6,700 |
| | 2-36 | Polymer 36 | F-3M(0.20) | A-6M(0.40) | B-1M(0.25) | B-3M(0.15) | — | 7,300 |
| | 2-37 | Polymer 37 | F-3M(0.20) | A-1M(0.35) | B-1M(0.25) | B-4M(0.20) | — | 7,000 |
| | 2-38 | Polymer 38 | F-3M(0.20) | A-1M(0.35) | B-1M(0.25) | B-5M(0.20) | — | 6,900 |
| | 2-39 | Polymer 39 | F-3M(0.20) | A-1M(0.35) | B-1M(0.25) | B-6M(0.20) | — | 6,800 |
| | 2-40 | Polymer 40 | F-3M(0.20) | A-1M(0.35) | B-1A(0.25) | B-3M(0.20) | — | 6,900 |
| | 2-41 | Polymer 41 | F-1M(0.40) | A-1M(0.25) | B-1M(0.25) | C-1M(0.10) | — | 6,500 |

TABLE 1-continued

|  | Resin | Unit 1 (ratio) | Unit 2 (ratio) | Unit 3 (ratio) | Unit 4 (ratio) | Unit 5 (ratio) | Mw |
|---|---|---|---|---|---|---|---|
| 2-42 | Polymer 42 | F-1M(0.30) | A-1M(0.35) | B-1M(0.25) | C-2M(0.10) | — | 6,700 |
| 2-43 | Polymer 43 | F-1M(0.30) | A-1M(0.35) | B-1M(0.25) | C-3M(0.10) | — | 6,900 |
| 2-44 | Polymer 44 | F-1M(0.40) | A-1M(0.25) | B-1M(0.25) | C-4M(0.10) | — | 6,800 |
| 2-45 | Polymer 45 | F-1M(0.40) | A-1M(0.25) | B-1M(0.25) | C-5M(0.10) | — | 6,800 |
| 2-46 | Polymer 46 | F-1M(0.40) | A-1M(0.25) | B-1M(0.25) | C-6M(0.10) | — | 7,000 |
| 2-47 | Polymer 47 | F-1M(0.35) | A-2M(0.30) | B-1M(0.25) | C-1M(0.10) | — | 6,800 |
| 2-48 | Polymer 48 | F-1M(0.35) | A-3M(0.25) | B-1M(0.25) | C-1M(0.10) | — | 7,100 |
| 2-49 | Polymer 49 | F-1M(0.40) | A-4M(0.25) | B-1M(0.25) | C-1M(0.10) | — | 6,900 |
| 2-50 | Polymer 50 | F-1M(0.35) | A-5M(0.30) | B-1M(0.25) | C-1M(0.10) | — | 7,000 |
| 2-51 | Polymer 51 | F-1M(0.35) | A-6M(0.30) | B-1M(0.25) | C-1M(0.10) | — | 7,300 |

TABLE 2

|  |  | Resin | Unit 1 (ratio) | Unit 2 (ratio) | Unit 3 (ratio) | Unit 4 (ratio) | Unit 5 (ratio) | Mw |
|---|---|---|---|---|---|---|---|---|
| Synthesis Example | 2-52 | Polymer 52 | F-1M(0.35) | A-2M(0.30) | B-1M(0.25) | C-4M(0.10) | — | 7,000 |
|  | 2-53 | Polymer 53 | F-1M(0.40) | A-3M(0.25) | B-1M(0.25) | C-4M(0.10) | — | 6,600 |
|  | 2-54 | Polymer 54 | F-1M(0.40) | A-4M(0.25) | B-1M(0.25) | C-4M(0.10) | — | 6,500 |
|  | 2-55 | Polymer 55 | F-1M(0.35) | A-5M(0.30) | B-1M(0.25) | C-4M(0.10) | — | 6,800 |
|  | 2-56 | Polymer 56 | F-1M(0.35) | A-6M(0.30) | B-1M(0.25) | C-4M(0.10) | — | 6,900 |
|  | 2-57 | Polymer 57 | F-1M(0.35) | A-2M(0.30) | B-1M(0.25) | C-6M(0.10) | — | 6,900 |
|  | 2-58 | Polymer 58 | F-1M(0.40) | A-3M(0.25) | B-1M(0.25) | C-6M(0.10) | — | 7,000 |
|  | 2-59 | Polymer 59 | F-1M(0.40) | A-4M(0.25) | B-1M(0.25) | C-6M(0.10) | — | 7,300 |
|  | 2-60 | Polymer 60 | F-1M(0.35) | A-5M(0.30) | B-1M(0.25) | C-6M(0.10) | — | 7,300 |
|  | 2-61 | Polymer 61 | F-1M(0.35) | A-6M(0.30) | B-1M(0.25) | C-6M(0.10) | — | 7,400 |
|  | 2-62 | Polymer 62 | F-3M(0.40) | A-1M(0.25) | B-1M(0.25) | C-1M(0.10) | — | 6,600 |
|  | 2-63 | Polymer 63 | F-3M(0.30) | A-1M(0.35) | B-1M(0.25) | C-2M(0.10) | — | 6,500 |
|  | 2-64 | Polymer 64 | F-3M(0.30) | A-1M(0.35) | B-1M(0.25) | C-3M(0.10) | — | 6,600 |
|  | 2-65 | Polymer 65 | F-3M(0.40) | A-1M(0.25) | B-1M(0.25) | C-4M(0.10) | — | 6,600 |
|  | 2-66 | Polymer 66 | F-3M(0.40) | A-1M(0.25) | B-1M(0.25) | C-5M(0.10) | — | 6,800 |
|  | 2-67 | Polymer 67 | F-3M(0.40) | A-1M(0.25) | B-1M(0.25) | C-6M(0.10) | — | 6,900 |
|  | 2-68 | Polymer 68 | F-3M(0.35) | A-2M(0.30) | B-1M(0.25) | C-1M(0.10) | — | 7,000 |
|  | 2-69 | Polymer 69 | F-3M(0.40) | A-3M(0.25) | B-1M(0.25) | C-1M(0.10) | — | 7,300 |
|  | 2-70 | Polymer 70 | F-3M(0.40) | A-4M(0.25) | B-1M(0.25) | C-1M(0.10) | — | 7,100 |
|  | 2-71 | Polymer 71 | F-3M(0.35) | A-5M(0.30) | B-1M(0.25) | C-1M(0.10) | — | 7,300 |
|  | 2-72 | Polymer 72 | F-3M(0.35) | A-6M(0.30) | B-1M(0.25) | C-1M(0.10) | — | 7,000 |
|  | 2-73 | Polymer 73 | F-3M(0.35) | A-2M(0.30) | B-1M(0.25) | C-4M(0.10) | — | 6,500 |
|  | 2-74 | Polymer 74 | F-3M(0.40) | A-3M(0.25) | B-1M(0.25) | C-4M(0.10) | — | 6,800 |
|  | 2-75 | Polymer 75 | F-3M(0.40) | A-4M(0.25) | B-1M(0.25) | C-4M(0.10) | — | 6,700 |
|  | 2-76 | Polymer 76 | F-3M(0.35) | A-5M(0.30) | B-1M(0.25) | C-4M(0.10) | — | 6,900 |
|  | 2-77 | Polymer 77 | F-3M(0.35) | A-6M(0.30) | B-1M(0.25) | C-4M(0.10) | — | 7,000 |
|  | 2-78 | Polymer 78 | F-3M(0.35) | A-2M(0.30) | B-1M(0.25) | C-6M(0.10) | — | 7,100 |
|  | 2-79 | Polymer 79 | F-3M(0.40) | A-3M(0.25) | B-1M(0.25) | C-6M(0.10) | — | 7,300 |
|  | 2-80 | Polymer 80 | F-3M(0.40) | A-4M(0.25) | B-1M(0.25) | C-6M(0.10) | — | 7,400 |
|  | 2-81 | Polymer 81 | F-3M(0.35) | A-5M(0.30) | B-1M(0.25) | C-6M(0.10) | — | 6,900 |
|  | 2-82 | Polymer 82 | F-3M(0.35) | A-6M(0.30) | B-1M(0.25) | C-6M(0.10) | — | 7,300 |
|  | 2-83 | Polymer 83 | F-1M(0.20) | A-1M(0.25) | B-1M(0.25) | B-3M(0.20) | C-1M(0.10) | 6,500 |
|  | 2-84 | Polymer 84 | F-1M(0.15) | A-1M(0.35) | B-1M(0.15) | B-3M(0.15) | C-2M(0.10) | 6,600 |
|  | 2-85 | Polymer 85 | F-1M(0.15) | A-1M(0.35) | B-1M(0.15) | B-3M(0.15) | C-3M(0.10) | 6,800 |
|  | 2-86 | Polymer 86 | F-1M(0.20) | A-1M(0.25) | B-1M(0.25) | B-3M(0.20) | C-4M(0.10) | 6,700 |
|  | 2-87 | Polymer 87 | F-1M(0.20) | A-1M(0.25) | B-1M(0.25) | B-3M(0.20) | C-5M(0.10) | 6,700 |
|  | 2-88 | Polymer 88 | F-1M(0.20) | A-1M(0.25) | B-1M(0.25) | B-3M(0.20) | C-6M(0.10) | 7,000 |
|  | 2-89 | Polymer 89 | F-3M(0.20) | A-1M(0.25) | B-1M(0.25) | B-3M(0.20) | C-1M(0.10) | 6,700 |
|  | 2-90 | Polymer 90 | F-3M(0.15) | A-1M(0.35) | B-1M(0.15) | B-3M(0.15) | C-2M(0.10) | 6,700 |
|  | 2-91 | Polymer 91 | F-3M(0.15) | A-1M(0.35) | B-1M(0.15) | B-3M(0.15) | C-3M(0.10) | 6,900 |
|  | 2-92 | Polymer 92 | F-3M(0.20) | A-1M(0.25) | B-1M(0.25) | B-3M(0.20) | C-4M(0.10) | 6,900 |
|  | 2-93 | Polymer 93 | F-3M(0.20) | A-1M(0.25) | B-1M(0.25) | B-3M(0.20) | C-5M(0.10) | 6,800 |
|  | 2-94 | Polymer 94 | F-3M(0.20) | A-1M(0.25) | B-1M(0.25) | B-3M(0.20) | C-6M(0.10) | 7,300 |
| Comparative Synthesis Example | 1-1 | Polymer 95 | — | A-1M(0.35) | B-1M(0.25) | B-3M(0.40) | — | 6,900 |
|  | 1-2 | Polymer 96 | — | A-3M(0.35) | B-1M(0.25) | B-4M(0.40) | — | 6,700 |
|  | 1-3 | Polymer 97 | — | A-1M(0.25) | B-1M(0.25) | B-3M(0.40) | C-6M(0.10) | 7,100 |

TABLE 3

F-1M (R = CH₃)   F-2M (R = CH₃)   F-3M (R = CH₃)   F-4M (R = CH₃)
F-1A (R = H)     F-2A (R = H)     F-3A (R = H)     F-4A (R = H)

TABLE 4

A-1M (R = CH₃)  A-2M (R = CH₃)  A-3M (R = CH₃)  A-4M (R = CH₃)  A-5M (R = CH₃)  A-6M (R = CH₃)
A-1A (R = H)    A-2A (R = H)    A-3A (R = H)    A-4A (R = H)    A-5A (R = H)    A-6A (R = H)

TABLE 5

B-1M (R = CH₃)  B-2M (R = CH₃)  B-3M (R = CH₃)  B-4M (R = CH₃)  B-5M (R = CH₃)  B-6M (R = CH₃)
B-1A (R = H)    B-2A (R = H)    B-3A (R = H)    B-4A (R = H)    B-5A (R = H)    B-6A (R = H)

TABLE 6

C-1M (R = CH₃)  C-2M (R = CH₃)  C-3M (R = CH₃)  C-4M (R = CH₃)  C-5M (R = CH₃)  C-6M (R = CH₃)
C-1A (R = H)    C-2A (R = H)    C-3A (R = H)    C-4A (R = H)    C-5A (R = H)    C-6A (R = H)

TABLE 6-continued

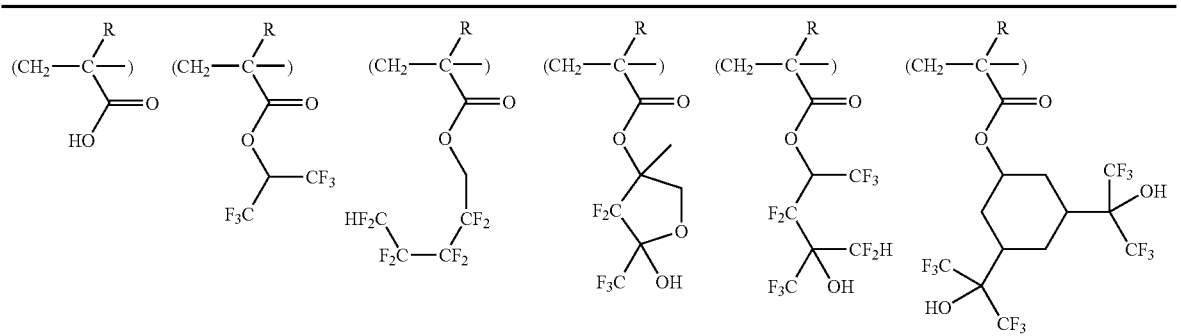

Preparation of Resist Compositions

Examples 1-1 to 1-31 & Comparative Examples 1-1 to 1-3

Resist compositions were prepared by using inventive Polymers or comparative Polymers 95 to 97 as the base resin, and dissolving the polymer, a photoacid generator (PAG), and a basic compound (Base) in a solvent mixture (PGMEA and CyHO) containing 0.01 wt % of surfactant KH-20 (Asahi Glass Co., Ltd.) in accordance with the recipe shown in Table 7. These compositions were each filtered through a Teflon® filter having a pore diameter 0.2 μm, thereby giving resist solutions.

TABLE 7

| | Resist | Resin (pbw) | PAG (pbw) | Base (pbw) | Solvent 1 (pbw) | Solvent 2 (pbw) |
|---|---|---|---|---|---|---|
| Example 1-1 | R-01 | Polymer 1 (80) | PAG-1 (4.4) | Base-1 (0.94) | PGMEA (560) | CyHO (240) |
| Example 1-2 | R-02 | Polymer 3 (80) | PAG-1 (4.4) | Base-1 (0.94) | PGMEA (560) | CyHO (240) |
| Example 1-3 | R-03 | Polymer 5 (80) | PAG-1 (4.4) | Base-1 (0.94) | PGMEA (560) | CyHO (240) |
| Example 1-4 | R-04 | Polymer 6 (80) | PAG-1 (4.4) | Base-1 (0.94) | PGMEA (560) | CyHO (240) |
| Example 1-5 | R-05 | Polymer 11 (80) | PAG-1 (4.4) | Base-1 (0.94) | PGMEA (560) | CyHO (240) |
| Example 1-6 | R-06 | Polymer 12 (80) | PAG-1 (4.4) | Base-1 (0.94) | PGMEA (560) | CyHO (240) |
| Example 1-7 | R-07 | Polymer 13 (80) | PAG-1 (4.4) | Base-1 (0.94) | PGMEA (560) | CyHO (240) |
| Example 1-8 | R-08 | Polymer 14 (80) | PAG-1 (4.4) | Base-1 (0.94) | PGMEA (560) | CyHO (240) |
| Example 1-9 | R-09 | Polymer 15 (80) | PAG-1 (4.4) | Base-1 (0.94) | PGMEA (560) | CyHO (240) |
| Example 1-10 | R-10 | Polymer 16 (80) | PAG-1 (4.4) | Base-1 (0.94) | PGMEA (560) | CyHO (240) |
| Example 1-11 | R-11 | Polymer 19 (80) | PAG-1 (4.4) | Base-1 (0.94) | PGMEA (560) | CyHO (240) |
| Example 1-12 | R-12 | Polymer 20 (80) | PAG-1 (4.4) | Base-1 (0.94) | PGMEA (560) | CyHO (240) |
| Example 1-13 | R-13 | Polymer 21 (80) | PAG-1 (4.4) | Base-1 (0.94) | PGMEA (560) | CyHO (240) |
| Example 1-14 | R-14 | Polymer 31 (80) | PAG-1 (4.4) | Base-1 (0.94) | PGMEA (560) | CyHO (240) |
| Example 1-15 | R-15 | Polymer 31 (80) | PAG-2 (4.9) | Base-1 (0.94) | PGMEA (560) | CyHO (240) |
| Example 1-16 | R-16 | Polymer 31 (80) | PAG-3 (4.6) | Base-1 (0.94) | PGMEA (560) | CyHO (240) |
| Example 1-17 | R-17 | Polymer 31 (80) | PAG-1 (4.4) | Base-2 (0.74) | PGMEA (560) | CyHO (240) |
| Example 1-18 | R-18 | Polymer 31 (80) | PAG-1 (4.4) | Base-3 (0.64) | PGMEA (560) | CyHO (240) |
| Example 1-19 | R-19 | Polymer 37 (80) | PAG-1 (4.4) | Base-1 (0.94) | PGMEA (560) | CyHO (240) |
| Example 1-20 | R-20 | Polymer 38 (80) | PAG-1 (4.4) | Base-1 (0.94) | PGMEA (560) | CyHO (240) |
| Example 1-21 | R-21 | Polymer 39 (80) | PAG-1 (4.4) | Base-1 (0.94) | PGMEA (560) | CyHO (240) |
| Example 1-22 | R-22 | Polymer 44 (80) | PAG-1 (4.4) | Base-1 (0.94) | PGMEA (560) | CyHO (240) |
| Example 1-23 | R-23 | Polymer 45 (80) | PAG-1 (4.4) | Base-1 (0.94) | PGMEA (560) | CyHO (240) |
| Example 1-24 | R-24 | Polymer 46 (80) | PAG-1 (4.4) | Base-1 (0.94) | PGMEA (560) | CyHO (240) |
| Example 1-25 | R-25 | Polymer 65 (80) | PAG-1 (4.4) | Base-1 (0.94) | PGMEA (560) | CyHO (240) |
| Example 1-26 | R-26 | Polymer 66 (80) | PAG-1 (4.4) | Base-1 (0.94) | PGMEA (560) | CyHO (240) |
| Example 1-27 | R-27 | Polymer 67 (80) | PAG-1 (4.4) | Base-1 (0.94) | PGMEA (560) | CyHO (240) |
| Example 1-28 | R-28 | Polymer 86 (80) | PAG-1 (4.4) | Base-1 (0.94) | PGMEA (560) | CyHO (240) |
| Example 1-29 | R-29 | Polymer 92 (80) | PAG-1 (4.4) | Base-1 (0.94) | PGMEA (560) | CyHO (240) |
| Example 1-30 | R-30 | Polymer 93 (80) | PAG-1 (4.4) | Base-1 (0.94) | PGMEA (560) | CyHO (240) |
| Example 1-31 | R-31 | Polymer 94 (80) | PAG-1 (4.4) | Base-1 (0.94) | PGMEA (560) | CyHO (240) |
| Comparative Example 1-1 | R-32 | Polymer 95 (80) | PAG-1 (4.4) | Base-1 (0.94) | PGMEA (560) | CyHO (240) |
| Comparative Example 1-2 | R-33 | Polymer 96 (80) | PAG-1 (4.4) | Base-1 (0.94) | PGMEA (560) | CyHO (240) |
| Comparative Example 1-3 | R-34 | Polymer 97 (80) | PAG-1 (4.4) | Base-1 (0.94) | PGMEA (560) | CyHO (240) |

The photoacid generator, base and solvent shown in Table 7 have the following meanings.
PAG-1: triphenylsulfonium nonafluorobutanesulfonate
PAG-2: 4-t-butoxyphenyldiphenylsulfonium nonafluorobutane-sulfonate
PAG-3: triphenylsulfonium 1,1,3,3,3-pentafluoro-2-cyclohexyl-carboxypropanesulfonate
Base-1: tri(2-methoxymethoxyethyl)amine
Base-2: 2-(2-methoxyethoxymethoxy)ethylmorpholine
Base-3: N-(2-acetoxyethyl)benzimidazole
PGMEA: 1-methoxyisopropyl acetate
CyHO: cyclohexanone Evaluation of Immersion Liquid Penetration Preventing Effect Examples 2-1 to 2-31 & Comparative Examples 2-1 to 2-3

A resist composition comprising the inventive polymer as a base resin was evaluated for the effect of preventing immersion liquid (water) from penetrating into a resist film. Specifically, the resist solution of Example 1 was coated onto a silicon wafer treated with hexamethyl disilazane (HMDS) and baked at 100° C. for 60 seconds to form a resist film of 50 nm thick. While the resist-coated wafer was kept horizontal, 50 microliters (μl) of deionized water was dropped thereon to form a droplet. The wafer was gradually inclined and the angle at which the droplet started sliding down was determined. The results are shown in Table 8.

TABLE 8

|  | Resist | Sliding angle (°) |
|---|---|---|
| Example 2-1 | R-01 | 24 |
| Example 2-2 | R-02 | 22 |
| Example 2-3 | R-03 | 25 |
| Example 2-4 | R-04 | 25 |
| Example 2-5 | R-05 | 23 |
| Example 2-6 | R-06 | 22 |
| Example 2-7 | R-07 | 24 |
| Example 2-8 | R-08 | 25 |
| Example 2-9 | R-09 | 25 |
| Example 2-10 | R-10 | 27 |
| Example 2-11 | R-11 | 28 |
| Example 2-12 | R-12 | 26 |
| Example 2-13 | R-13 | 24 |
| Example 2-14 | R-14 | 22 |
| Example 2-15 | R-15 | 23 |
| Example 2-16 | R-16 | 24 |
| Example 2-17 | R-17 | 24 |
| Example 2-18 | R-18 | 23 |
| Example 2-19 | R-19 | 23 |
| Example 2-20 | R-20 | 24 |
| Example 2-21 | R-21 | 26 |
| Example 2-22 | R-22 | 24 |
| Example 2-23 | R-23 | 22 |
| Example 2-24 | R-24 | 22 |
| Example 2-25 | R-25 | 23 |
| Example 2-26 | R-26 | 22 |
| Example 2-27 | R-27 | 21 |
| Example 2-28 | R-28 | 23 |
| Example 2-29 | R-29 | 22 |
| Example 2-30 | R-30 | 21 |
| Example 2-31 | R-31 | 20 |
| Comparative Example 2-1 | R-32 | 32 |
| Comparative Example 2-2 | R-33 | 34 |
| Comparative Example 2-3 | R-34 | 30 |

As seen from Table 8, the resist compositions comprising the inventive polymers as the base resin have a smaller sliding angle, indicating that the resist films are effective for preventing penetration of immersion liquid (water). A smaller sliding angle also indicates an easier flow of water on the film, advantageously allowing for a higher scanning speed during scan exposure.

Evaluation of Resist Composition

Examples 3-1 to 3-31 & Comparative Examples 3-1 to 3-3

Each of inventive resist compositions (R-01 to 31) and comparative resist compositions (R-32 to 34) was spin coated on a silicon wafer having an antireflective coating (ARC-29A, Nissan Chemical Co., Ltd.) of 78 nm thick and baked at 110° C. for 60 seconds, forming a resist film of 170 nm thick. The wafer was exposed by means of an ArF excimer laser stepper (Nikon Corp., NA 0.68), post-exposure baked (PEB) for 60 seconds, and puddle developed with a 2.38 wt % tetramethylammonium hydroxide aqueous solution for 30 seconds, forming a 1:1 line-and-space pattern. During the PEB, an optimum temperature for each resist composition was employed. The wafer as developed was observed under a top-down SEM. The optimum exposure (Eop, mJ/cm$^2$) was defined as the exposure dose which provided a 1:1 resolution at the top and bottom of a 0.11-μm 1:1 line-and-space pattern. The maximum resolution of the resist was defined as the minimum line width (in increments of 0.01 μm) of the lines and spaces that separated at the optimum exposure, with smaller values indicating better resolution.

The evaluation results (Eop and maximum resolution) of the resist compositions are shown in Table 9.

TABLE 9

|  | Resist | PEB temperature | Eop | Maximum resolution |
|---|---|---|---|---|
| Example 3-1 | R-01 | 105° C. | 40.0 mJ/cm$^2$ | 0.10 μm |
| Example 3-2 | R-02 | 105° C. | 40.0 mJ/cm$^2$ | 0.10 μm |
| Example 3-3 | R-03 | 110° C. | 41.0 mJ/cm$^2$ | 0.09 μm |
| Example 3-4 | R-04 | 125° C. | 44.0 mJ/cm$^2$ | 0.09 μm |
| Example 3-5 | R-05 | 110° C. | 41.0 mJ/cm$^2$ | 0.09 μm |
| Example 3-6 | R-06 | 110° C. | 40.0 mJ/cm$^2$ | 0.09 μm |
| Example 3-7 | R-07 | 125° C. | 46.0 mJ/cm$^2$ | 0.09 μm |
| Example 3-8 | R-08 | 115° C. | 44.0 mJ/cm$^2$ | 0.09 μm |
| Example 3-9 | R-09 | 120° C. | 42.0 mJ/cm$^2$ | 0.09 μm |
| Example 3-10 | R-10 | 115° C. | 43.0 mJ/cm$^2$ | 0.09 μm |
| Example 3-11 | R-11 | 105° C. | 39.0 mJ/cm$^2$ | 0.10 μm |
| Example 3-12 | R-12 | 100° C. | 38.0 mJ/cm$^2$ | 0.10 μm |
| Example 3-13 | R-13 | 110° C. | 42.0 mJ/cm$^2$ | 0.09 μm |
| Example 3-14 | R-14 | 110° C. | 42.0 mJ/cm$^2$ | 0.09 μm |
| Example 3-15 | R-15 | 110° C. | 44.0 mJ/cm$^2$ | 0.09 μm |
| Example 3-16 | R-16 | 110° C. | 42.0 mJ/cm$^2$ | 0.09 μm |
| Example 3-17 | R-17 | 110° C. | 41.0 mJ/cm$^2$ | 0.09 μm |
| Example 3-18 | R-18 | 110° C. | 42.0 mJ/cm$^2$ | 0.09 μm |
| Example 3-19 | R-19 | 110° C. | 41.0 mJ/cm$^2$ | 0.10 μm |
| Example 3-20 | R-20 | 110° C. | 41.0 mJ/cm$^2$ | 0.10 μm |
| Example 3-21 | R-21 | 110° C. | 40.0 mJ/cm$^2$ | 0.09 μm |
| Example 3-22 | R-22 | 110° C. | 41.0 mJ/cm$^2$ | 0.09 μm |
| Example 3-23 | R-23 | 110° C. | 41.0 mJ/cm$^2$ | 0.09 μm |
| Example 3-24 | R-24 | 110° C. | 40.0 mJ/cm$^2$ | 0.09 μm |
| Example 3-25 | R-25 | 110° C. | 41.0 mJ/cm$^2$ | 0.09 μm |
| Example 3-26 | R-26 | 110° C. | 40.0 mJ/cm$^2$ | 0.09 μm |
| Example 3-27 | R-27 | 110° C. | 40.0 mJ/cm$^2$ | 0.10 μm |
| Example 3-28 | R-28 | 110° C. | 41.0 mJ/cm$^2$ | 0.09 μm |
| Example 3-29 | R-29 | 110° C. | 41.0 mJ/cm$^2$ | 0.09 μm |
| Example 3-30 | R-30 | 110° C. | 41.0 mJ/cm$^2$ | 0.09 μm |
| Example 3-31 | R-31 | 110° C. | 39.0 mJ/cm$^2$ | 0.09 μm |
| Comparative Example 3-1 | R-32 | 110° C. | 42.0 mJ/cm$^2$ | 0.12 μm |
| Comparative Example 3-2 | R-33 | 115° C. | 45.0 mJ/cm$^2$ | 0.13 μm |
| Comparative Example 3-3 | R-34 | 110° C. | 43.0 mJ/cm$^2$ | 0.11 μm |

It is evident from Table 9 that the resist compositions within the scope of the invention are improved in resolution and dissolution when processed by ArF excimer laser lithography.

All the aforementioned patent publications are incorporated herein by reference.

Japanese Patent Application No. 2006-001102 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A lactone-containing compound having the general formula (1):

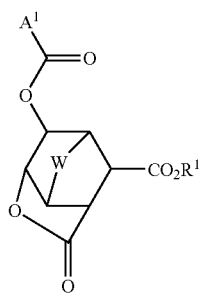

wherein $A^1$ is a polymerizable functional group having a carbon-to-carbon double bond, $R^1$ is a straight, branched or cyclic monovalent hydrocarbon group of 2 to 10 carbon atoms in which some or all hydrogen atoms on constituent carbons are substituted by fluorine atoms, and W is $CH_2$, an oxygen atom or a sulfur atom.

2. The lactone-containing compound of claim 1, having the general formula (2):

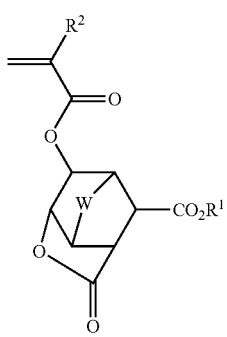

wherein $R^1$ and W are as defined above, and $R^2$ is hydrogen, fluorine, methyl or trifluoromethyl.

3. The lactone-containing compound of claim 2, wherein $R^1$ is one selected from the group consisting of the following formulae:

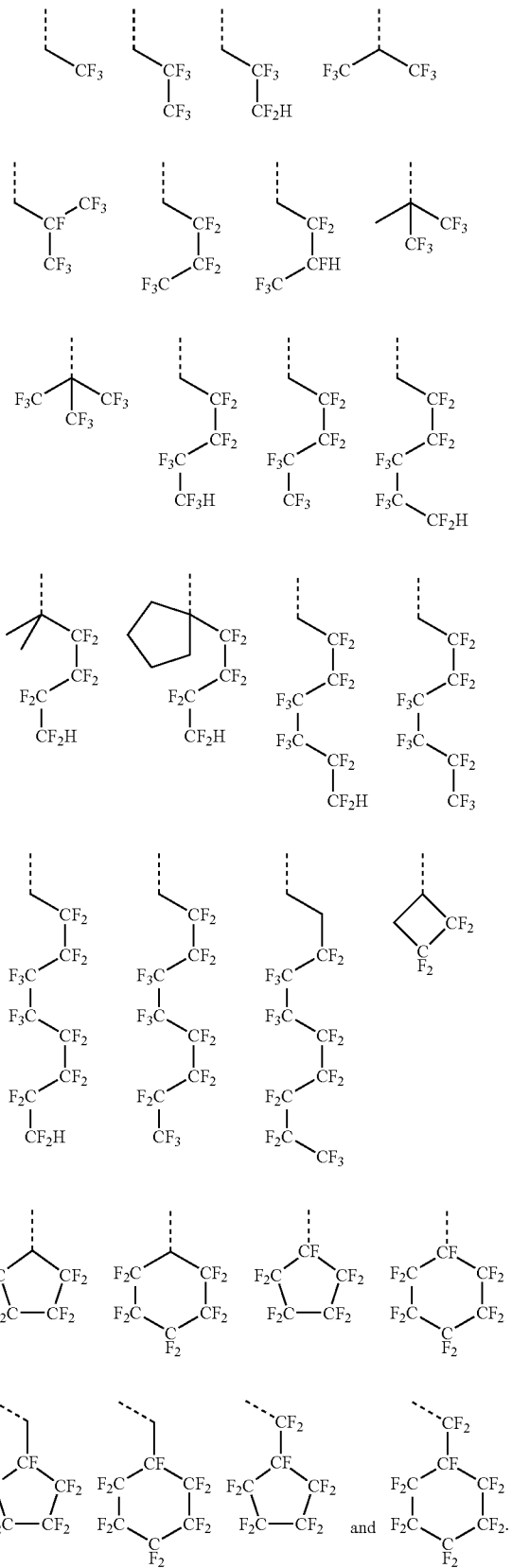

4. The lactone-containing compound of claim 1, having the general formula (3):

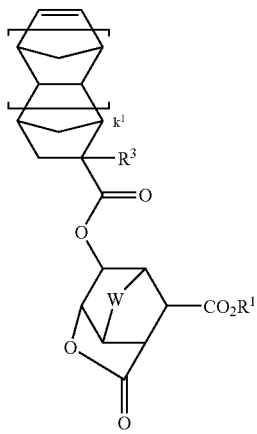
(3)

wherein $R^1$ and W are as defined above, $R^3$ is hydrogen, fluorine, methyl or trifluoromethyl, and $k^1$ is 0 or 1.

5. The lactone-containing compound of claim 4, wherein $R^1$ is one selected from the group consisting of the following formulae:

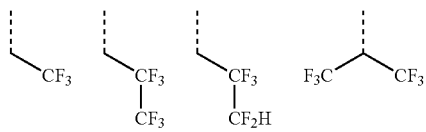

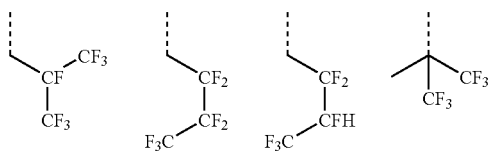

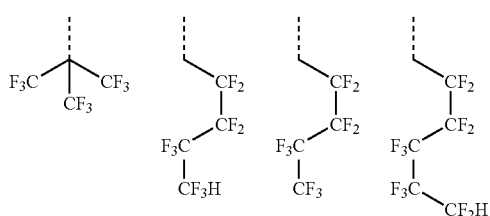

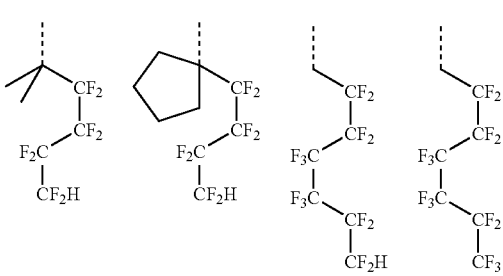

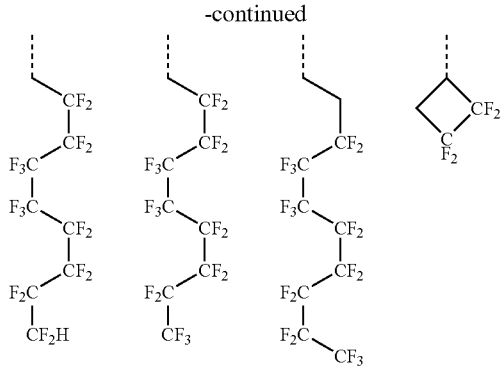

-continued

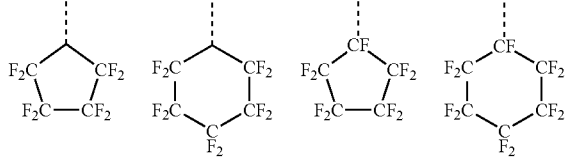

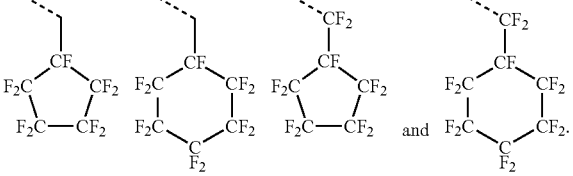

6. A polymer comprising recurring units derived from the lactone-containing compound of claim 1.

7. The polymer of claim 6, further comprising recurring units having at least one of the general formulae (4) to (7):

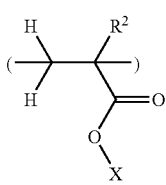
(4)

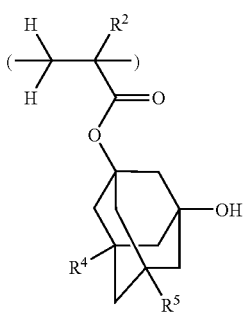
(5)

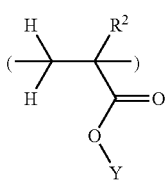
(6)

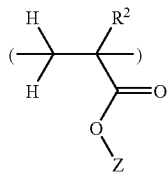
(7)

wherein $R^2$ is hydrogen, fluorine, methyl or trifluoromethyl, $R^4$ and $R^5$ are each independently hydrogen or hydroxyl, X is an acid labile group, Y is a substituent group having a lactone structure different from formula (1), and Z is hydrogen, a fluoroalkyl group of 1 to 15 carbon atoms or a fluoroalcohol-containing substituent group of 1 to 15 carbon atoms.

8. A resist composition comprising the polymer of claim 6 as a base resin.

9. A process for forming a pattern comprising the steps of applying the resist composition of claim 8 onto a substrate to form a coating, heat treating the coating, exposing the coating to high-energy radiation or electron beam through a photomask, optionally heat treating the exposed coating, and developing it with a developer.

10. The lactone-containing compound of claim 1, wherein $R^1$ is one selected from the group consisting of the following formulae:

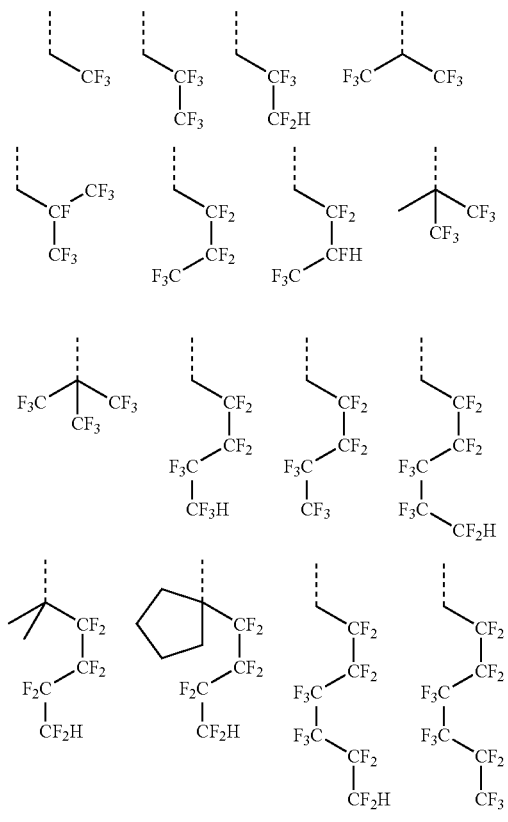

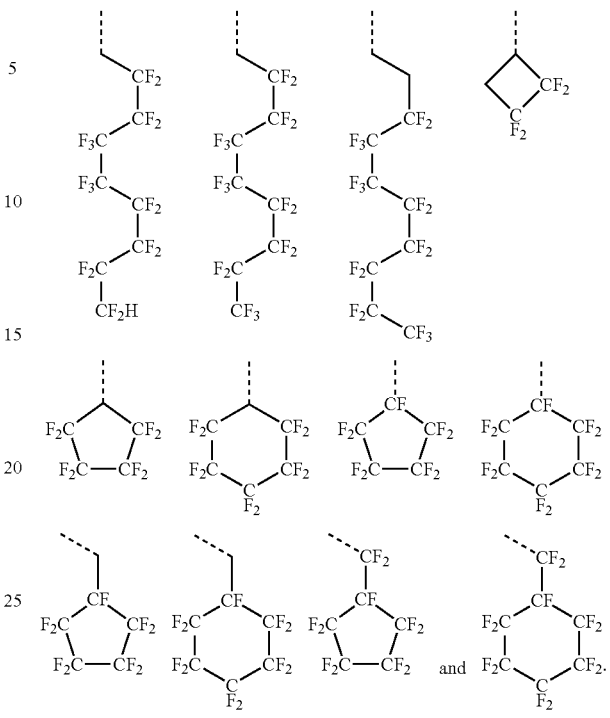

11. A polymer comprising recurring units having either one of the general formulae (1a) to (1c):

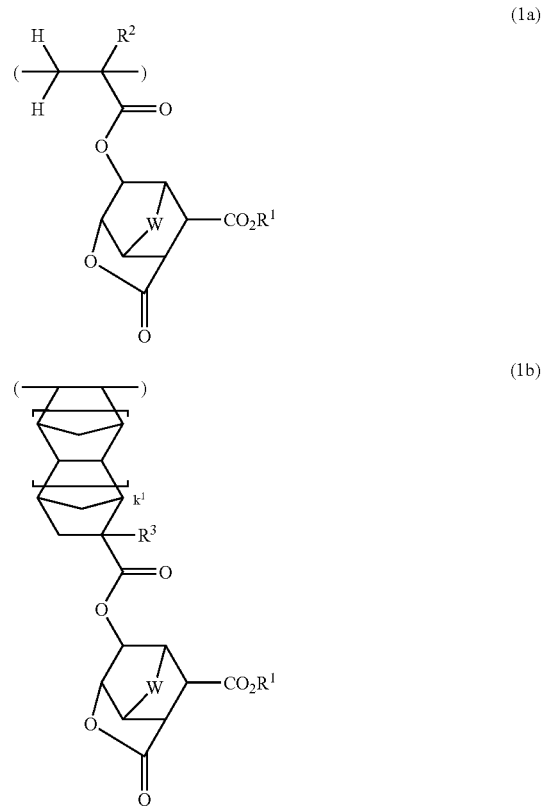

(1a)

(1b)

(1c)

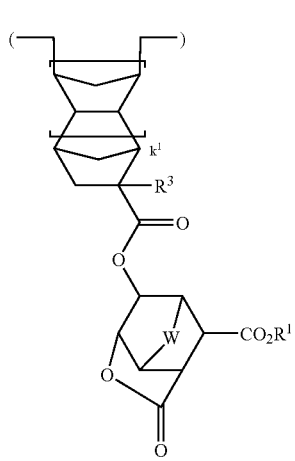

wherein $R^1$ is a straight, branched or cyclic monovalent hydrocarbon group of 2 to 10 carbon atoms in which some or all hydrogen atoms on constituent carbons are substituted by fluorine atoms, $R^2$ is hydrogen, fluorine, methyl or trifluoromethyl, $R^3$ is hydrogen, fluorine, methyl or trifluoromethyl, W is $CH_2$, an oxygen atom or a sulfur atom, and $k^1$ is 0 or 1.

12. The polymer of claim 11, wherein $R^1$ is one selected from the group consisting of the following formulae:

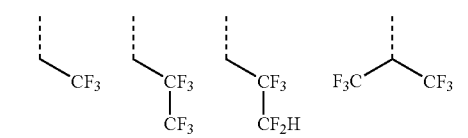

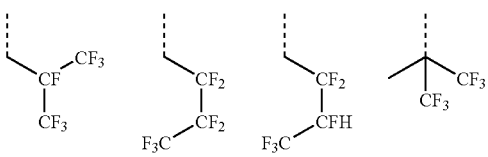

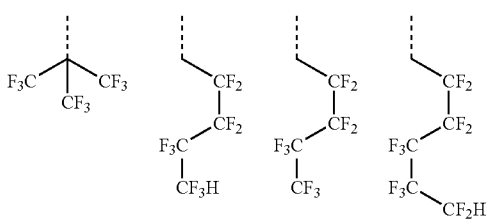

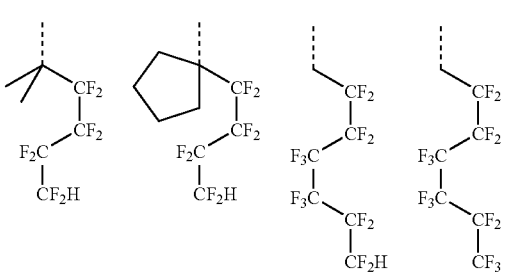

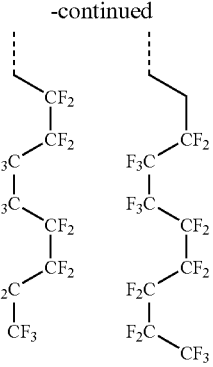

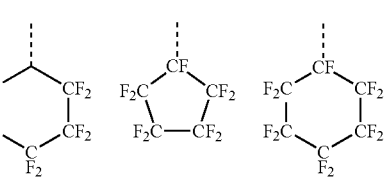

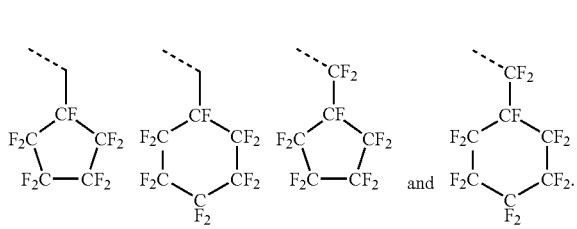

13. The polymer of claim 12, further comprising recurring units having at least one of the general formulae (4) to (7):

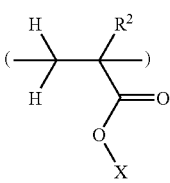
(4)

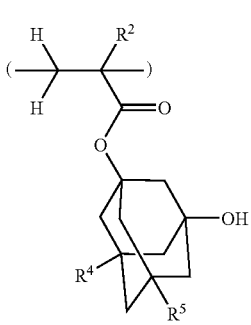
(5)

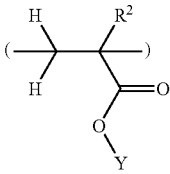
(6)

-continued

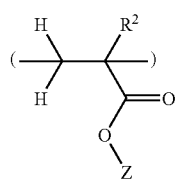

(7)

wherein $R^2$ is hydrogen, fluorine, methyl or trifluoromethyl, $R^4$ and $R^5$ are each independently hydrogen or hydroxyl, X is an acid labile group, Y is a substituent group having a lactone structure different from formula (1), and Z is hydrogen, a fluoroalkyl group of 1 to 15 carbon atoms or a fluoroalcohol-containing substituent group of 1 to 15 carbon atoms.

14. A resist composition comprising the polymer of claim 13 as a base resin.

15. A resist composition comprising the polymer of claim 12 as a base resin.

16. A lactone-containing compound selected from the group consisting of the following monomers:

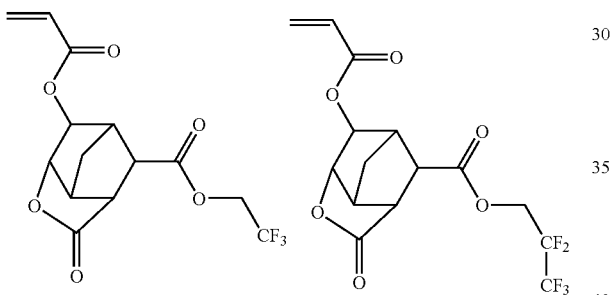

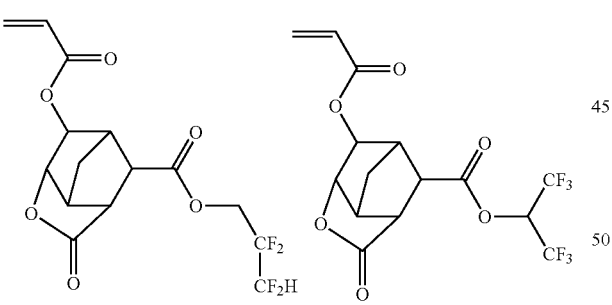

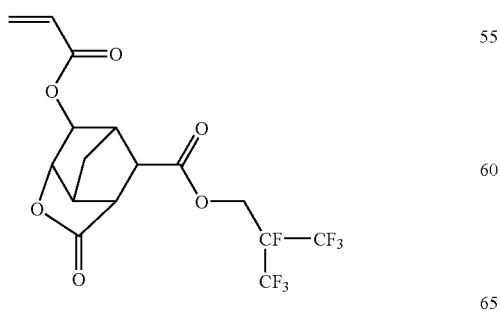

-continued

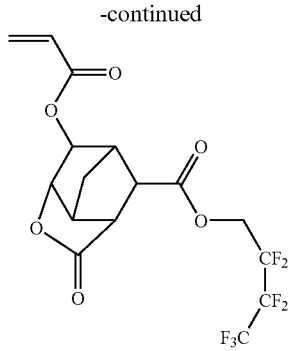

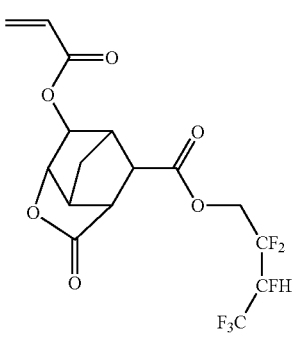

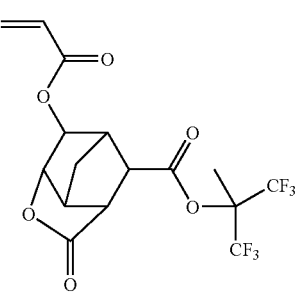

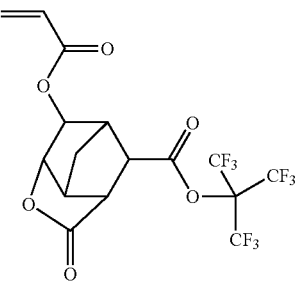

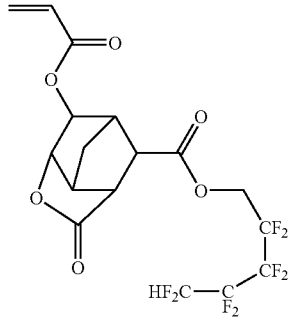

-continued
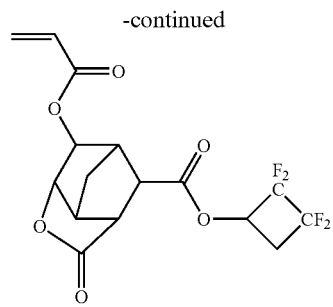
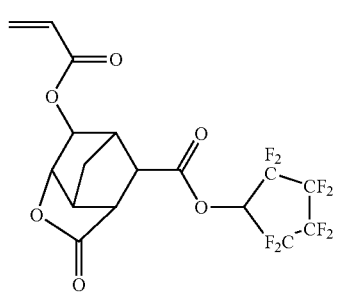
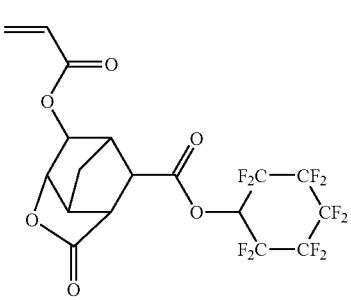
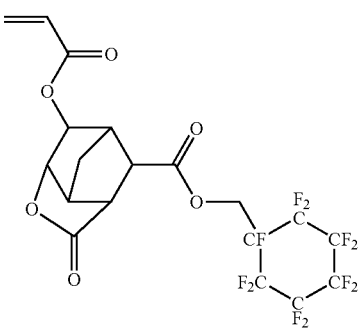
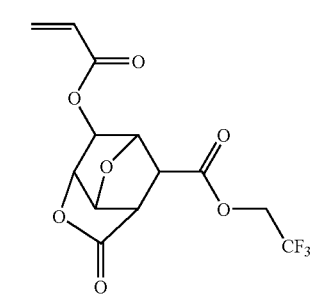
-continued
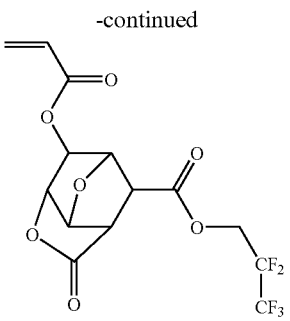
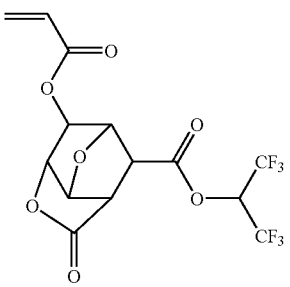
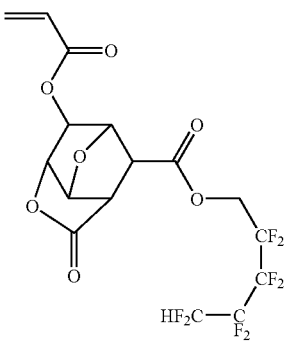
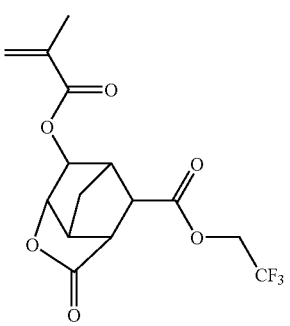
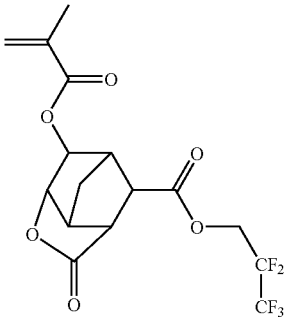

107
-continued
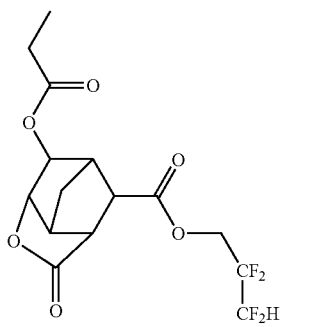
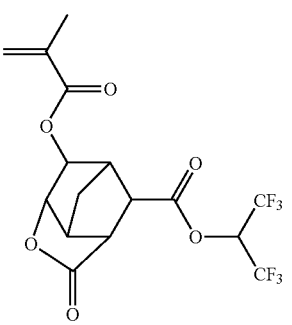
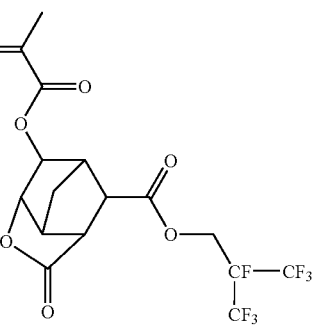
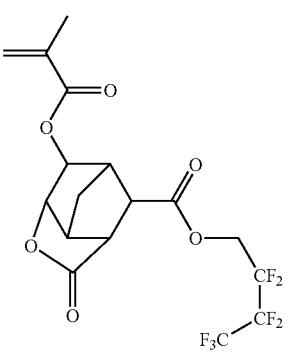
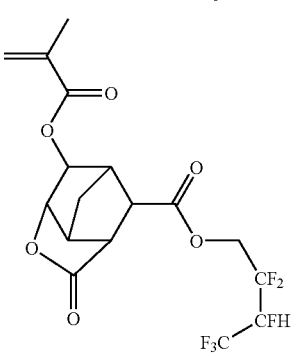
108
-continued
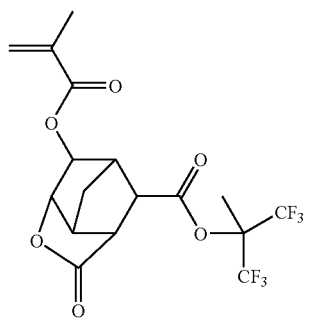
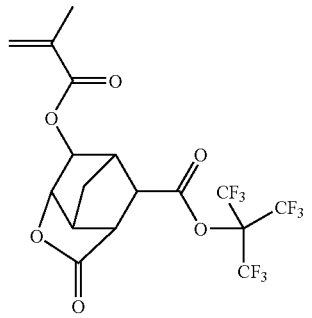
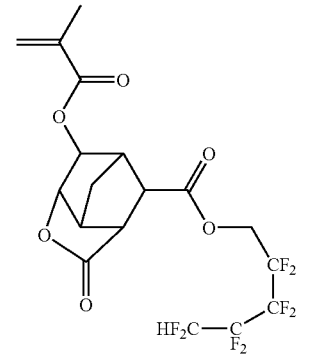
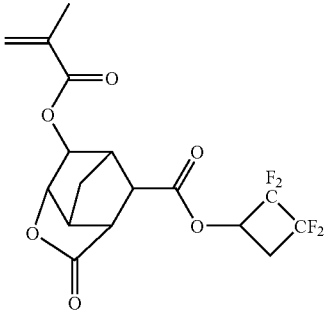
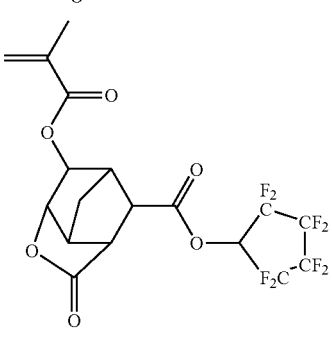

-continued
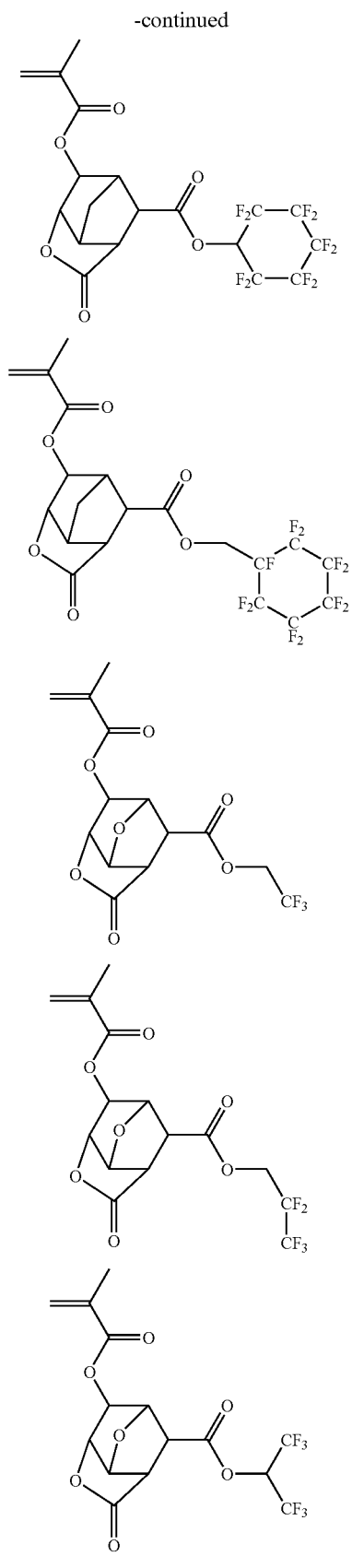
-continued
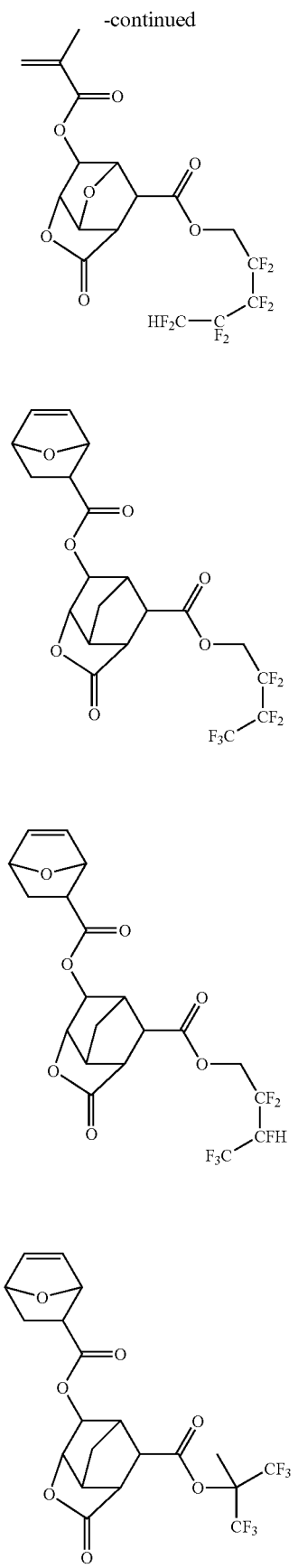

| 111 | 112 |
|---|---|
| 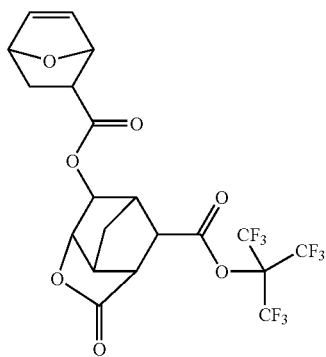 | 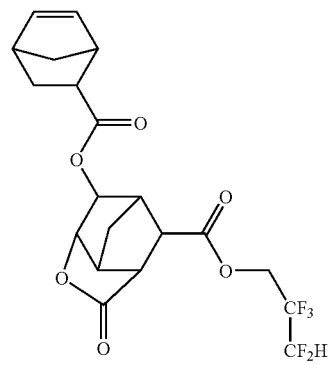 |
| 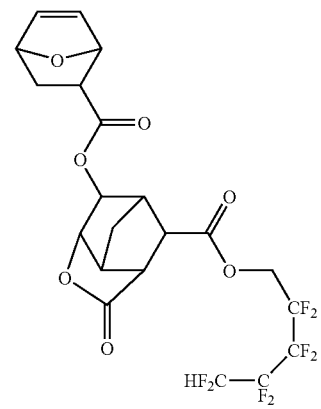 | 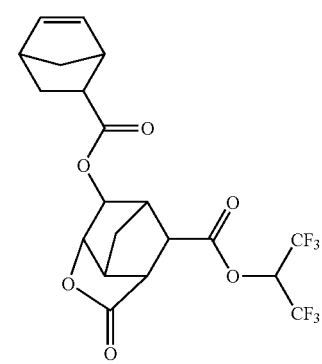 |
| 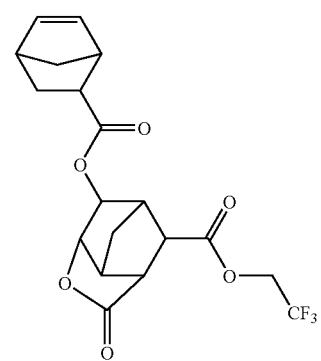 | 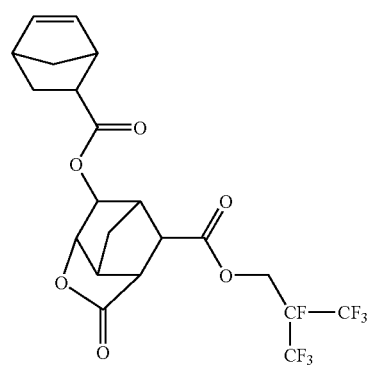 |
| 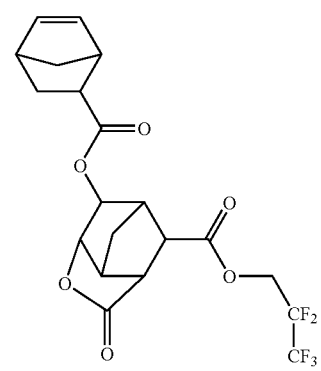 | 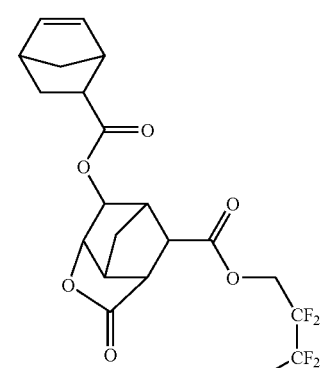 |

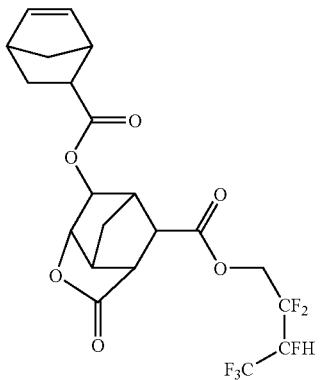
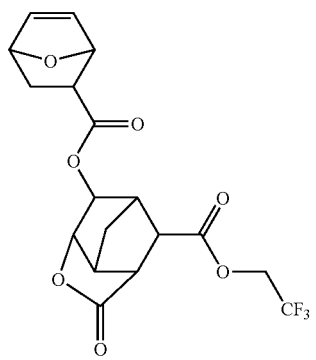
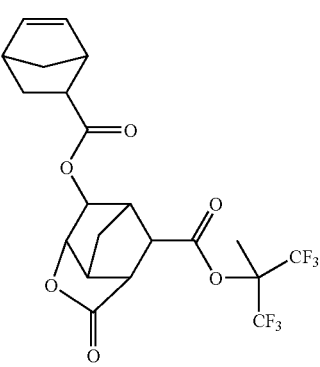
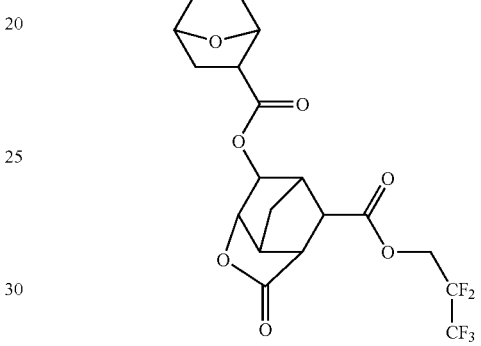
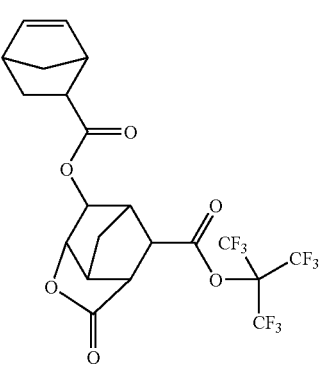
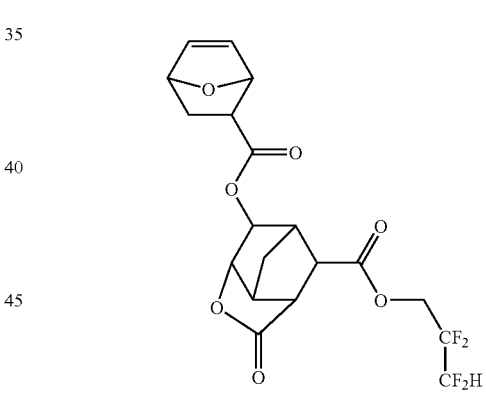
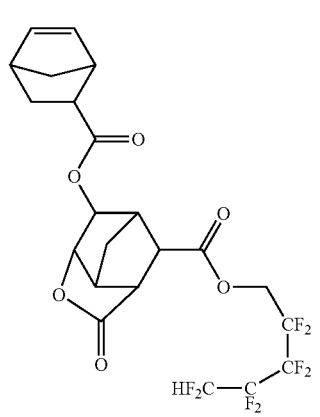

-continued
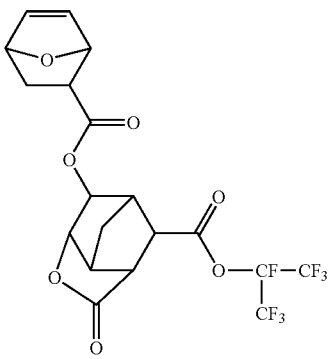
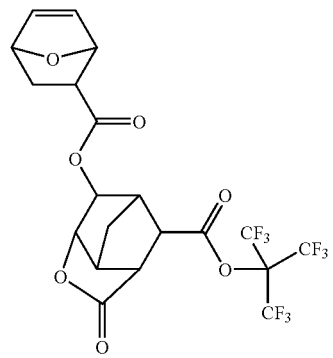
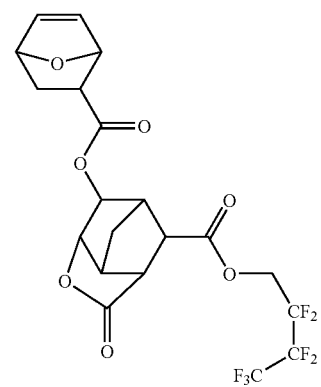
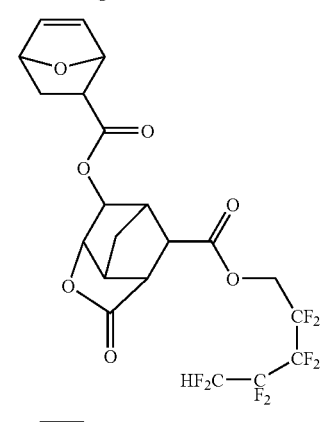
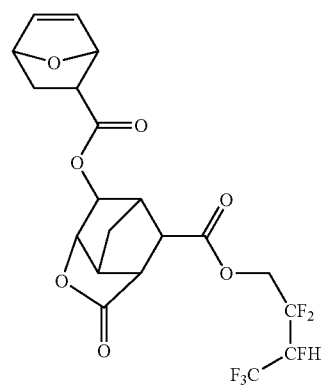
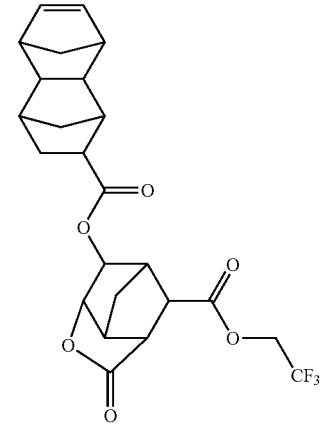
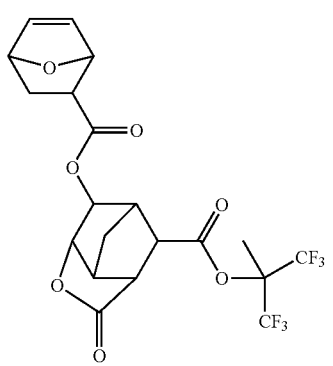
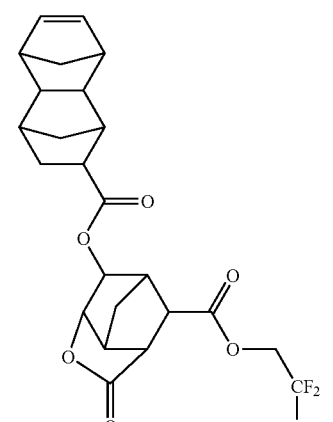

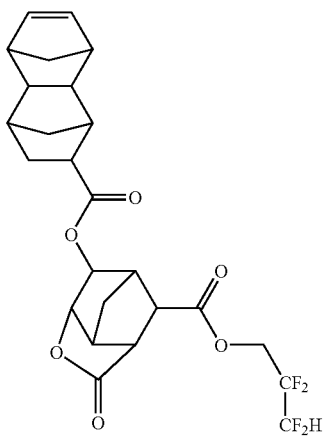
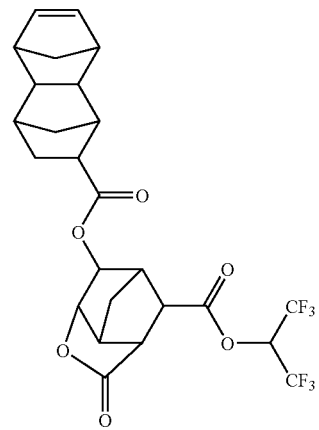
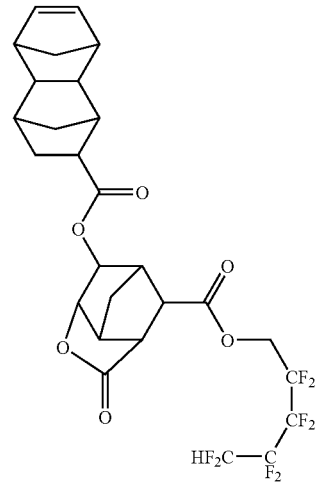
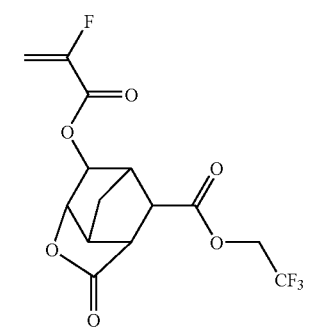
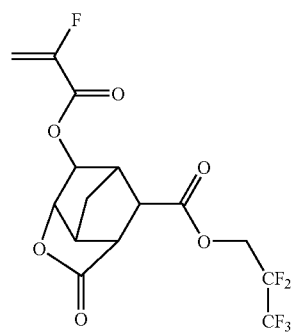
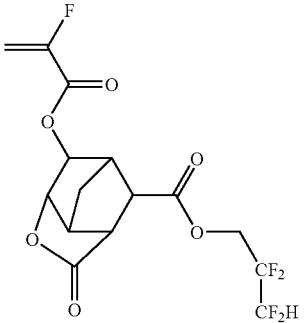
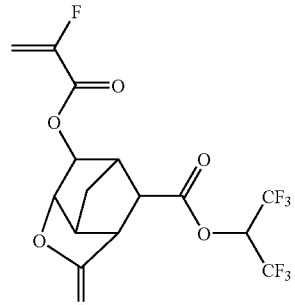
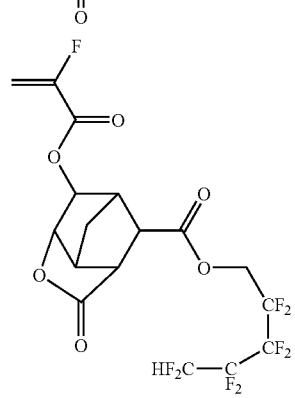

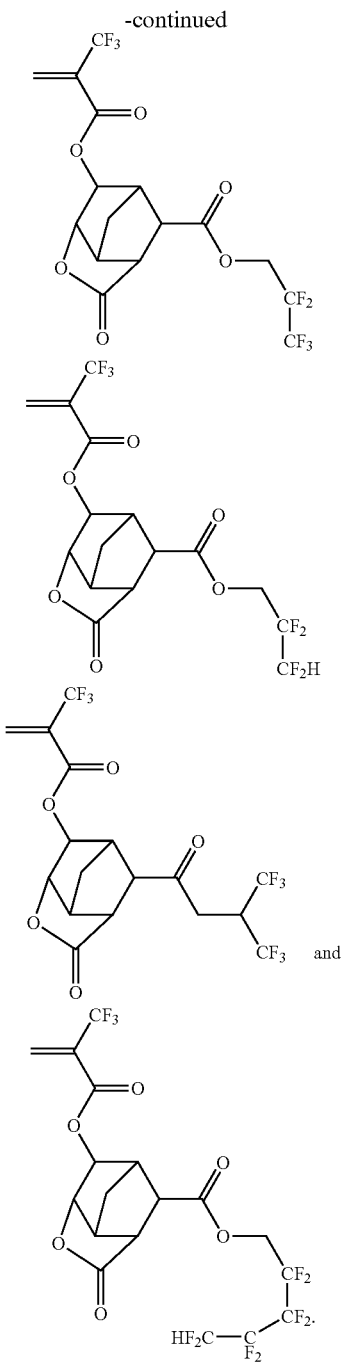

17. A polymer comprising recurring units derived from the lactone-containing compound of claim 16.

18. The polymer of claim 17, further comprising recurring units having at least one of the general formulas (4) to (7):

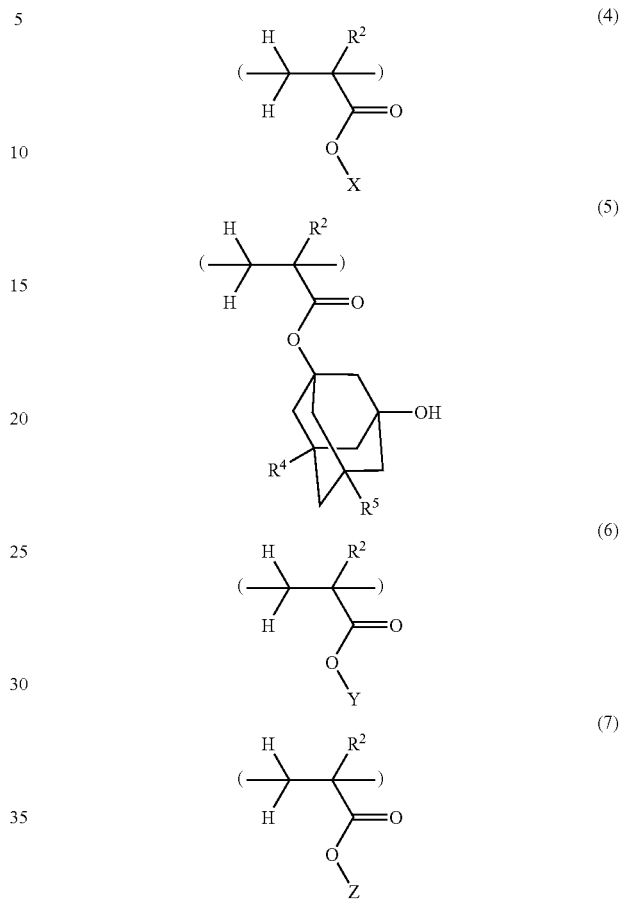

wherein $R^2$ is hydrogen, fluorine, methyl or trifluoromethyl, $R^4$ and $R^5$ are each independently hydrogen or hydroxyl, X is an acid labile group, Y is a substituent group having a lactone structure different from formula (1), and Z is hydrogen, a fluoroalkyl group of 1 to 15 carbon atoms or a fluoroalcohol-containing substituent group of 1 to 15 carbon atoms.

19. A resist composition comprising the polymer of claim 18 as a base resin.

20. A process for forming a pattern comprising the steps of applying the resist composition of claim 19 onto a substrate to form a coating, heat treating the coating, exposing the coating to high-energy radiation or electron beam through a photomask, optionally heat treating the exposed coating, and developing it with a developer.

* * * * *